US 7,785,840 B2

(12) United States Patent
Bathe et al.

(10) Patent No.: US 7,785,840 B2
(45) Date of Patent: Aug. 31, 2010

(54) METHOD OF PRODUCTION OF L-AMINO ACIDS

(75) Inventors: Brigitte Bathe, Salzkotten (DE); Wilfried Claes, Bielefeld (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 11/777,423

(22) Filed: Jul. 13, 2007

(65) Prior Publication Data

US 2008/0014618 A1 Jan. 17, 2008

Related U.S. Application Data

(60) Provisional application No. 60/830,331, filed on Jul. 13, 2006.

(30) Foreign Application Priority Data

Jul. 13, 2006 (DE) .................. 10 2006 032 634

(51) Int. Cl.
*C12P 19/34* (2006.01)
*C12N 15/09* (2006.01)
*C12N 1/20* (2006.01)
*C12N 15/00* (2006.01)
*C12N 15/77* (2006.01)

(52) U.S. Cl. .............. 435/91.1; 435/320.1; 435/252.32; 435/477; 435/487

(58) Field of Classification Search ................ 435/91.1, 435/320.1, 252.32, 487
See application file for complete search history.

(56) References Cited

U.S. PATENT DOCUMENTS

| | | | |
|---|---|---|---|
| 4,656,135 | A | 4/1987 | Tsuchida et al. |
| 4,822,738 | A | 4/1989 | Miwa et al. |
| 5,188,948 | A | 2/1993 | Katsurada et al. |
| 5,250,423 | A | 10/1993 | Murakami et al. |
| 5,250,434 | A | 10/1993 | Yamada et al. |
| 5,275,940 | A | 1/1994 | Kino et al. |
| 5,521,074 | A | 5/1996 | Katsumata et al. |
| 5,705,370 | A | 1/1998 | Tsuchida et al. |
| 5,770,409 | A | 6/1998 | Pfefferle et al. |
| 5,840,551 | A | 11/1998 | Werning et al. |
| 5,990,350 | A | 11/1999 | Stevens et al. |
| 6,004,773 | A | 12/1999 | Araki et al. |
| 6,090,597 | A | 7/2000 | Hirano et al. |
| 6,303,383 | B1 | 10/2001 | Nakamura et al. |
| 6,340,486 | B1 | 1/2002 | Binder et al. |
| 6,844,176 | B1 | 1/2005 | Bathe et al. |
| 6,861,246 | B2 | 3/2005 | Kreutzer et al. |
| 6,893,848 | B1 | 5/2005 | Yokoi et al. |
| 6,965,021 | B2 | 11/2005 | Hanke et al. |
| 6,995,002 | B2 | 2/2006 | Molenaar et al. |
| 7,094,106 | B2 | 8/2006 | Yamamoto et al. |
| 7,214,526 | B2 | 5/2007 | Bathe et al. |
| 2003/0152633 | A1 | 8/2003 | Kushiki et al. |
| 2005/0220933 | A1 | 10/2005 | Hong et al. |
| 2007/0082031 | A1 | 4/2007 | Lotter et al. |

FOREIGN PATENT DOCUMENTS

| | | |
|---|---|---|
| AU | 3181993 | 7/1993 |
| CA | 2059319 | 7/1992 |
| DE | 4100920 | 7/1992 |
| DE | 10339847 | 3/2005 |
| DE | 102006016158.0 | 4/2006 |
| DE | 102005045301 | 4/2007 |
| EP | 0 197 335 B1 | 2/1991 |
| EP | 0435132 | 7/1991 |
| EP | 0533039 | 3/1993 |
| EP | 0534865 | 3/1993 |
| EP | 0551614 | 7/1993 |
| EP | 0 358 940 B1 | 9/1995 |
| EP | 1239040 | 9/2002 |
| WO | WO 2005/021772 A1 | 3/2005 |
| WO | WO 2006/077004 A2 | 7/2006 |
| WO | WO 2006/100177 A1 | 9/2006 |

OTHER PUBLICATIONS

Eikmanns BJ, et al., Nucleotide sequence, expression and transcriptional analysis of the *Corynebacterium glutamicum* gltA gene encoding citrate synthase. Microbiology. Aug. 1994;140 ( Pt 8):1817-28.*
Ohnishi J, et al., Comparisons of potentials for L-lysine production among different *Corynebacterium glutamicum* strains.Biosci Biotechnol Biochem. Apr. 2006;70(4):1017-20.*
Radmacher E., The three tricarboxylate synthase activities of *Corynebacterium glutamicum* and increase of L-lysine synthesisAppl Microbiol Biotechnol. Sep. 2007;76(3):587-95. Epub Jul. 26, 2007.*
Voet, Biochemistry John Wiley and Sons, 1990, pp. 126-128.*
Kimchi-Sarfaty C et al., A "silent" polymorphism in the MDR1 gene changes substrate specificity.Science. Jan. 26, 2007;315(5811):525-8.*

(Continued)

*Primary Examiner*—Maria Leavitt
(74) *Attorney, Agent, or Firm*—Oblon, Spivak, McClelland, Maier & Neustadt, L.L.P.

(57) ABSTRACT

An isolated polynucleotide encodes a polypeptide comprising the amino acid sequence of SEQ ID NO: 2, with the L-aspartic acid at position 5 of the amino acid sequence replaced by another proteinogenic amino acid, and possesses citrate synthase activity. In addition, a vector comprises the polynucleotide and a bacterium comprises the vector. An isolated polynucleotide comprises a nucleotide sequence comprising, from position 1 to 39, the nucleotide sequence corresponding to position 1 to 39 of SEQ ID NO: 11, from position 40 to 105, a nucleotide sequence encoding the amino acid sequence of SEQ ID NO: 12, with each proteinogenic amino acid except L-aspartic acid being present at position 5. A method of producing an L-amino acids is also described.

7 Claims, 1 Drawing Sheet

OTHER PUBLICATIONS

Faridmoayer A, Scaman CH. Binding residues and catalytic domain of soluble *Saccharomyces cerevisiae* processing alpha-glucosidase I.Glycobiology. Dec. 2005;15(12):1341-8. Epub Jul. 13, 2005 1171.*

Rudinger, J., "Characteristics of the amino acids as components of a peptide hormone sequence",in Peptide Hormones, University Park Press: Baltimore, MD, pp. 1-7, 1976.*

Bork Power and Pitfalls in Sequence Analysis: The 70% Hurdle Genome Research 10:398-400 (2000).*

Bowie, j et al., Deciphering the message in protein sequences: tolerance to amino acid substitutions.Science. 1990 ;247:1306-10.*

Tobias Georgi, et al., "Lysine and glutamate production by *Corynebacterium glutamicum* on glucose, fructose and sucrose: Roles of malic enzyme and fructose-1,6-bisphosphatase", Metabolic Engineering, vol. 7, No. 4, XP-005052640, Jul. 2005, pp. 291-301.

Database Biosis [Online], AN PREV198886014353, Agricultural and Biological Chemistry, XP-002477332, 1988, 1 page.

Rittman et al, Arch Microbiol (2003) 180: 285-292.

Claes et al, Journal of Bacteriology (2002) 184(10): 2728-2739.

Handbook of *Cornebacterium glutamicum*, edited by Eggeling and Bott, Published 2005, CRC Press, Taylor & Francis Group, Boca Raton, FL.

QUIGEN Product Guide 2006, sections 8.1 + 8.2, Protein.

* cited by examiner

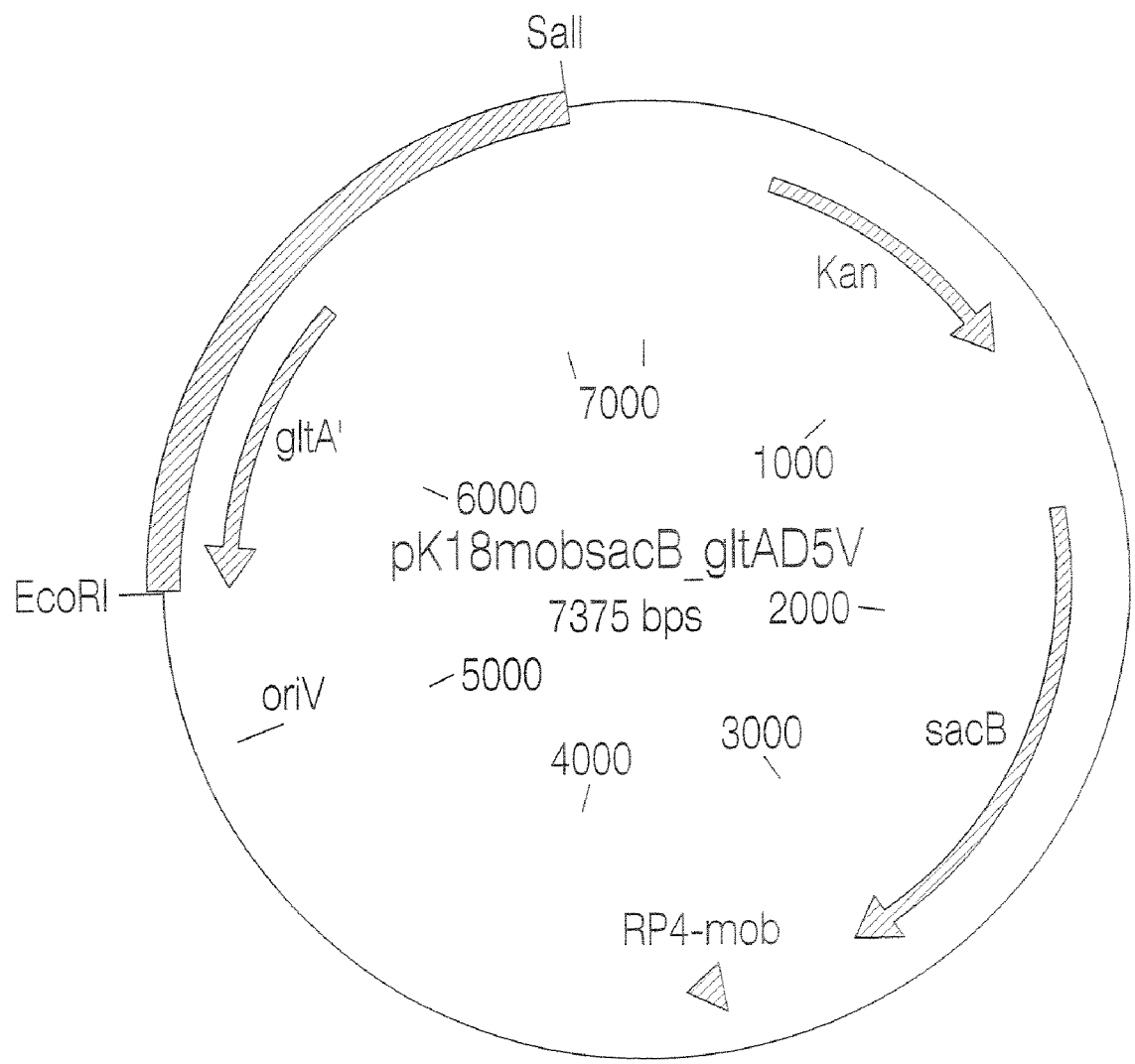

METHOD OF PRODUCTION OF L-AMINO ACIDS

BACKGROUND OF THE INVENTION

1. Field of the Invention

The invention relates to novel polynucleotides coding for a polypeptide with citrate synthase activity, bacteria containing the polynucleotides and polypeptides and methods of production of amino acids using these bacteria.

2. Discussion of the Background

All publications, patent applications, patents, and other references mentioned herein are incorporated by reference in their entirety. Further, the materials, methods, and examples are illustrative only and are not intended to be limiting, unless otherwise specified.

Amino acids are used in human medicine, in the pharmaceutical industry, in the food industry and quite particularly in animal nutrition.

Amino acids may be produced by fermentation of strains of coryneform bacteria, preferably *Corynebacterium glutamicum*. Owing to their great importance, work is constantly in progress for improving the production processes. Process improvements may relate to the fermentation technology, for example, stirring and supply of oxygen, or to the composition of the nutrient media, for example, the sugar concentration during fermentation, or processing to the product form by, for example, ion-exchange chromatography, or to the intrinsic performance characteristics of the microorganism itself.

Methods of mutagenesis, selection and mutant screening are employed for improving the performance characteristics of these microorganisms. In this way we obtain strains that are resistant to antimetabolites or are auxotrophic for metabolites of regulatory importance, and which produce amino acids. A known antimetabolite is the lysine analog S-(2-aminoethyl)-L-cysteine (AEC).

Methods of recombinant DNA technology have also been used for some years now for strain improvement of L-amino acid-producing strains of the genus *Corynebacterium*, preferably *Corynebacterium glutamicum*, by amplifying individual amino acid biosynthesis genes and investigating the effect on amino acid production.

Synoptic descriptions of the biology, genetics and biotechnology of *Corynebacterium glutamicum* are given in "Handbook of *Corynebacterium glutamicum*" (Eds.: L. Eggeling and M. Bott, CRC Press, Taylor & Francis, 2005), in the special issue of the Journal of Biotechnology (Chief Editor: A. Pühler) with the title "A new era in *Corynebacterium glutamicum* biotechnology" (Journal of Biotechnology 104/1-3, (2003)) and in the book by T. Scheper (Managing Editor) "Microbial Production of L-Amino Acids" (Advances in Biochemical Engineering/Biotechnology 79, Springer Verlag, Berlin, Germany, 2003).

The nucleotide sequence of the genome of *Corynebacterium glutamicum* is described in Ikeda and Nakagawa (Applied Microbiology and Biotechnology 62, 99-109 (2003)), in EP 1 108 790 and in Kalinowski et al. (Journal of Biotechnology 104/1-3, 2003)).

The nucleotide sequence of the genome of *Corynebacterium efficiens* is described in Nishio et al. (Genome Research, 13 (7), 1572-1579 (2003)).

The nucleotide sequences of the genome of *Corynebacterium glutamicum* and *Corynebacterium efficiens* are also available in the database of the National Center for Biotechnology Information (NCBI) of the National Library of Medicine (Bethesda, Md., USA), in the DNA Data Bank of Japan (DDBJ, Mishima, Japan) or in the nucleotide sequence database of the European Molecular Biology Laboratories (EMBL, Heidelberg, Germany and Cambridge, UK).

The wild-type sequence of the coding region of the gltA gene of *Corynebacterium glutamicum* is presented in SEQ ID NO: 1 in the specification of the present application. In addition, the sequences located upstream and downstream of the coding region are shown in SEQ ID NO: 3 and 25. The amino acid sequence of the encoded GltA polypeptide (citrate synthase) is accordingly given in SEQ ID NOs: 2, 4 and 26.

SUMMARY OF THE INVENTION

It was an object of the present invention to provide novel measures for the improved production of L-amino acids, preferably L-lysine, L-valine and L-isoleucine, and more preferably L-lysine.

This and other objects have been achieved by the present invention the first embodiment of which includes an isolated polynucleotide, encoding a polypeptide comprising the amino acid sequence of SEQ ID NO: 2, wherein the L-aspartic acid at position 5 of the amino acid sequence is replaced by another proteinogenic amino acid and wherein the polypeptide possesses citrate synthase activity.

The invention further provides a vector comprising the isolated polynucleotide and a bacterium that has been transformed with the vector.

The invention also provides a method of production of an L-amino acid.

BRIEF DESCRIPTION OF THE DRAWING

The FIGURE represents a map of the plasmid pK18mobsacB_gltAD5V.

DETAILED DESCRIPTION OF THE INVENTION

The invention relates to an isolated polynucleotide that codes for a polypeptide which comprises the amino acid sequence of SEQ ID NO: 2, wherein the L-aspartic acid at position 5 of the amino acid sequence is replaced by another proteinogenic amino acid, preferably L-valine, L-leucine and L-isoleucine, and more preferably L-valine, and wherein the polypeptide possesses citrate synthase activity (EC No. 4.1.3.7). Optionally, the polypeptide comprises at least one conservative amino acid substitution, with the citrate synthase activity of the polypeptide being essentially unchanged by the conservative amino acid substitutions.

Proteinogenic amino acids are understood as meaning the amino acids that occur in natural proteins, i.e. in proteins of microorganisms, plants, animals and humans. These include in particular L-amino acids, selected from the group L-aspartic acid, L-asparagine, L-threonine, L-serine, L-glutamic acid, L-glutamine, glycine, L-alanine, L-cysteine, L-valine, L-methionine, L-isoleucine, L-leucine, L-tyrosine, L-phenylalanine, L-histidine, L-lysine, L-tryptophan, L-proline and L-arginine.

The terms polypeptide and protein are used as synonyms.

The invention further relates to vectors and bacteria, preferably of the genus *Corynebacterium* and *Escherichia*, and more preferably of the species *Corynebacterium glutamicum* and *Escherichia coli*, which contain the stated polynucleotide or were produced using the stated polynucleotide.

The invention also relates finally to bacteria preferably of the genus *Corynebacterium* and *Escherichia*, and more preferably of the species *Corynebacterium glutamicum* and *Escherichia coli*, which have been transformed with the stated vector.

The term transformation comprises all methods for transferring polynucleotides, preferably DNA, into a desired bacterium. Among other things these include the use of isolated DNA in transformation, electrotransformation or electroporation, transfer by cellular contact as in conjugation or the transfer of DNA by particle bombardment.

A further aspect of the invention relates to a bacterium, that may be a recombinant bacterium, of the genus *Corynebacterium*, which comprises a polynucleotide that codes for a polypeptide with citrate synthase activity, which comprises the amino acid sequence of SEQ ID NO: 2, wherein each proteinogenic amino acid except L-aspartic acid, preferably L-valine, L-leucine and L-isoleucine, and preferably L-valine, is contained at position 5 of the amino acid sequence. Optionally, the polypeptide may contain one or more conservative amino acid substitution(s), with the citrate synthase activity of the polypeptide being essentially unchanged by the conservative amino acid substitutions.

A further aspect of the invention relates to a method of production of L-amino acids, preferably L-lysine, L-valine and L-isoleucine, and more preferably L-lysine, comprising the following steps:

a) fermentation of the recombinant bacteria of the genus *Corynebacterium* according to the invention in a suitable nutrient medium, and b) accumulation of the L-amino acid in the nutrient medium or in the cells of the bacteria.

"L-amino acids" means the proteinogenic amino acids.

If L-lysine or lysine is mentioned hereinafter, this is intended to mean not only the bases, but also the salts, for example L-lysine monohydrochloride or L-lysine sulfate.

With regard to the bacteria of the genus *Corynebacterium*, L-amino acid-excreting strains are preferred, based on the following species:

*Corynebacterium efficiens*, for example the strain DSM44549,

*Corynebacterium glutamicum*, for example the strain ATCC13032,

*Corynebacterium thermoaminogenes*, for example the strain FERM BP-1539, and

*Corynebacterium ammoniagenes*, for example the strain ATCC6871, the species *Corynebacterium glutamicum* being preferred.

Some representatives of the species *Corynebacterium glutamicum* are also known under different designations. Examples include:

*Corynebacterium acetoacidophilum* ATCC 13870,
*Corynebacterium lilium* DSM20137,
*Corynebacterium melassecola* ATCC 17965,
*Brevibacterium flavum* ATCC14067,
*Brevibacterium lactofermentum* ATCC 13869, and
*Brevibacterium divaricatum* ATCC14020.

Known representatives of amino acid-excreting strains of the genus *Corynebacterium* are, for example, the L-lysine producing strains:

*Corynebacterium glutamicum* DM58-1/pDM6 (=DSM4697) described in EP 0 358 940,

*Corynebacterium glutamicum* MH20-22B (=DSM16835) described in Menkel et al. (Applied and Environmental Microbiology 55(3), 684-688 (1989)),

*Corynebacterium glutamicum* AHP-3 (=FERM BP-7382) described in EP 1 108 790,

*Corynebacterium glutamicum* DSM16834 described in (PCT/EP2005/012417),

*Corynebacterium glutamicum* DSM17119 described in (PCT/EP2006/060851),

*Corynebacterium glutamicum* DSM17223 described in (PCT/EP2006/062010),

*Corynebacterium glutamicum* DSM16937 described in (PCT/EP2005/057216), and

*Corynebacterium thermoaminogenes* AJ12521 (=FERM BP-3304) described in U.S. Pat. No. 5,250,423;

or the L-valine producing strains:

*Brevibacterium lactofermentum* FERM BP-1763 described in U.S. Pat. No. 5,188,948,

*Brevibacterium lactofermentum* FERM BP-3007 described in U.S. Pat. No. 5,521,074,

*Corynebacterium glutamicum* FERM BP-3006 described in U.S. Pat. No. 5,521,074, and

*Corynebacterium glutamicum* FERM BP-1764 described in U.S. Pat. No. 5,188,948;

or the L-isoleucine producing strains:

*Brevibacterium flavum* FERM-BP 759 described in U.S. Pat. No. 4,656,135,

*Corynebacterium glutamicum* FERM-BP 757 described in U.S. Pat. No. 4,656,135,

*Brevibacterium flavum* FERM-BP 760 described in U.S. Pat. No. 4,656,135,

*Corynebacterium glutamicum* FERM-BP 758 described in U.S. Pat. No. 4,656,135,

*Brevibacterium flavum* FERM BP-2215 described in U.S. Pat. No. 5,705,370, and

*Brevibacterium flavum* FERM BP-2433 described in U.S. Pat. No. 5,705,370.

Information on the taxonomic classification of strains of this group of bacteria can be found inter alia in Seiler (Journal of General Microbiology 129, 1433-1477 (1983)), Kämpfer and Kroppenstedt (Canadian Journal of Microbiology 42, 989-1005 (1996)), Liebl et al. (International Journal of Systematic Bacteriology 41, 255-260 (1991)) and in U.S. Pat. No. 5,250,434.

Strains with the designation "ATCC" can be obtained from the American Type Culture Collection (Manassas, Va., USA). Strains with the designation "DSM" can be obtained from the Deutsche Sammlung von Mikroorganismen und Zellkulturen (DSMZ, Braunschweig, Germany). Strains with the designation "FERM" can be obtained from the National Institute of Advanced Industrial Science and Technology (AIST Tsukuba Central 6, 1-1-1 Higashi, Tsukuba Ibaraki, Japan). The strain *Corynebacterium thermoaminogenes* (FERM BP-1539) is described in U.S. Pat. No. 5,250,434.

For production of the polynucleotides, it is possible to use classical in-vivo mutagenesis techniques with cell populations of bacteria of the genus *Corynebacterium* using mutagenic substances such as N-methyl-N'-nitro-N-nitrosoguanidine (MNNG) or using ultraviolet light. Mutagenesis techniques are described for example in the Manual of Methods for General Bacteriology (Gerhard et al. (Eds.), American Society for Microbiology, Washington, D.C., USA, 1981) or in Tosaka et al. (Agricultural and Biological Chemistry 42(4), 745-752 (1978)) or in Konicek et al. (Folia Microbiologica 33, 337-343 (1988)).

From the mutagenized cell population, those mutants are taken and multiplied which require L-glutamic acid or citric acid in order to be able to grow on a minimal agar or whose growth on the minimal agar is improved by adding L-glutamic acid or citric acid. It is also possible, starting from mutants requiring L-glutamic acid or citric acid, to isolate so-called revertants, which do not require L-glutamic acid or citric acid for their growth. These L-glutamic acid-auxotrophic or citric acid-auxotrophic mutants or their respective revertants are then investigated. Technical details on the isolation of mutants with defective citrate synthase activity can be found for example in Shiio et al. (Agricultural and Biological Chemistry 46(1), 101-107 (1982)).

Next, DNA is prepared or isolated from the mutants and by means of, for example, the polymerase chain reaction (PCR) using primer pairs which allow the amplification of the gltA gene or gltA allele, the corresponding polynucleotide is synthesized and isolated.

For this, it is possible to select any primer pairs from the nucleotide sequence located upstream and downstream of the coding region and the nucleotide sequence that is complementary to it (see SEQ ID NOs: 3 and 25). A primer of a primer pair then comprises preferably at least 15, at least 18, at least 20, at least 21 or at least 24 consecutive nucleotides selected from the nucleotide sequence between position 1 and 1000 of SEQ ID NO: 25. The associated second primer of a primer pair comprises at least 15, at least 18, at least 20, at least 21 or at least 24 consecutive nucleotides selected from the complementary nucleotide sequence between position 3314 and 2312 of SEQ ID NO: 25.

A person skilled in the art will find instructions and information on PCR for example in the handbook "PCR Strategies" (Innis, Felfand and Sninsky, Academic Press, Inc., 1995), in the handbook by Diefenbach and Dveksler "PCR Primer—a laboratory manual" (Cold Spring Harbor Laboratory Press, 1995), in Gait's handbook "Oligonucleotide Synthesis: a Practical Approach" (IRL Press, Oxford, UK, 1984) and in Newton and Graham "PCR" (Spektrum Akademischer Verlag, Heidelberg, Germany, 1994).

Further instructions on PCR can be found for example in WO 06/100177 on pages 15 to 17.

In a further step, the nucleotide sequence of the polynucleotide is then determined. This can for example be determined by the chain-terminating technique of Sanger et al. (Proceedings of the National Academies of Sciences, USA, 74, 5463-5467 (1977)) with the modifications stated by Zimmermann et al. (Nucleic Acids Research 18, 1067 pp (1990)).

The polypeptide encoded by this nucleotide sequence can then be analyzed with respect to the amino acid sequence. For this, the nucleotide sequence is input in a program for translating a DNA sequence into an amino acid sequence. Suitable programs are for example the "Patentin" program, which is obtainable from patent offices, for example the US Patent Office (USPTO), or the "Translate Tool", which is available on the ExPASy Proteomics Server on the World Wide Web (Gasteiger et al., Nucleic Acids Research 31, 3784-3788 (2003)).

It is also possible for the polynucleotide, which is also designated hereinafter as gltA allele, to be produced by methods of in-vitro genetics.

Suitable methods for in-vitro mutagenesis including among others treatment with hydroxylamine according to Miller (Miller, J. H.: A Short Course in Bacterial Genetics. A Laboratory Manual and Handbook for *Escherichia coli* and Related Bacteria, Cold Spring Harbor Laboratory Press, Cold Spring Harbor, 1992) or the use of a polymerase chain reaction using a DNA polymerase, which has a high error rate. Such a DNA polymerase is for example the Mutazyme DNA Polymerase (GeneMorph PCR Mutagenesis Kit, No. 600550) of the company Stratagene (La Jolla, Calif., USA). It is also possible to use mutagenic oligonucleotides, as described by T. A. Brown (Gentechnologie für Einsteiger, Spektrum Akademischer Verlag, Heidelberg, 1993) and R. M. Horton (PCR-mediated recombination and mutagenesis, Molecular Biotechnology 3, 93-99 (1995)). The method using the "Quik Change Site-directed Mutagenesis Kit" of the company Stratagene (La Jolla, Calif., USA) described by Papworth et al. (Strategies 9(3), 3-4 (1996)) can also be used.

Methods for the determination of citrate synthase activity can be found in Eikmanns et al. (Microbiology 140, 1817-1828 (1994)) and in Shiio et al. (Agricultural and Biological Chemistry 46(1), 101-107 (1982)).

It is moreover possible to overexpress the citrate synthase allele according to the invention in *Corynebacterium glutamicum* or *Escherichia coli*, and it can then be prepared in purified or isolated form.

A polynucleotide with the nucleotide sequence shown in SEQ ID NO: 5 was isolated in this way. The polypeptide encoded by this polynucleotide is shown in SEQ ID NO: 6 and 8. It contains L-valine instead of L-aspartic acid at position 5 of the amino acid sequence.

It was found that when the strain ATCC13032 is provided, instead of the wild-type gltA gene, with the gltA allele according to the invention, which codes for the citrate synthase according to SEQ ID NO: 6 (ATCC13032::gltA D5V), in comparison with the wild-type strain ATCC13032, which contains the citrate synthase according to SEQ ID NO: 2, with enzyme activity reduced by approx. 40% up to a maximum of approx. 90%, preferably with enzyme activity reduced by approx. 70% up to a maximum of approx. 90%.

It is known that conservative amino acid substitutions only change the enzyme activity insignificantly. Accordingly, the invention also relates to polynucleotides that code for polypeptides with citrate synthase activity, which in addition to the amino acid substitutions at position 5 of the amino acid sequence contain one (1) or more conservative amino acid substitution(s), which does not alter the enzyme activity substantially. That is, it remains essentially unchanged. The term "not altered substantially," "essentially unchanged," or "substantially unchanged" means in this context that the citrate synthase activity of the polypeptide is altered by at most 20%, preferably at most 10% and more preferably at most 5% to at most 2% in comparison with the citrate synthase activity of the polypeptide according to SEQ ID NO: 10 or SEQ ID NO: 6, preferably SEQ ID NO: 6.

For an experimental test, the gltA gene of strain ATCC13032 is substituted for the gltA allele, which codes for a polypeptide containing the amino acid substitution at position 5 and at least one conservative amino acid substitution. Then the strain is cultivated, a cellular extract is produced and the citrate synthase activity is determined. As a reference, the citrate synthase activity in strain ATCC13032::gltA D5V is determined.

Instead of strain ATCC13032, it is also possible to use L-lysine-excreting strains of *Corynebacterium glutamicum* which comprises the coding region of the gltA gene of the wild type including the nucleotide sequences located upstream, corresponding to the nucleotide sequence between position 1 and 2064 of SEQ ID NO: 3, preferably SEQ ID NO: 3. Suitable strains are, for example, DSM16833 described in PCT/EP2005/012417, DSM13994 described in EP 1 239 040 A2 or DSM17576 described in DE 102005045301. In these strains, the appropriate mutation(s) can be inserted in the coding region of the gltA gene by, for example, allelic substitution.

It is also possible to purify the polypeptides and to conduct the comparative tests on the purified polypeptides.

The enzyme citrate synthase (EC No. 4.1.3.7) catalyzes the condensation reaction of oxaloacetate and acetyl-CoA, with formation of citric acid and coenzyme A (CoA) as reaction products. The enzyme is assigned the number EC 2.3.3.1 in the Kyoto Encyclopedia of Genes and Genomes (KEGG, Kanehisa Laboratory, Bioinformatics Center, Institute for Chemical Research, Kyoto University, Japan).

In the case of aromatic L-amino acids, we talk of conservative substitutions when L-phenylalanine, L-tryptophan and L-tyrosine are substituted for one another. In the case of hydrophobic L-amino acids, we talk of conservative substitutions when L-leucine, L-isoleucine and L-valine are substituted for one another. In the case of polar L-amino acids, we talk of conservative substitutions when L-glutamine and L-asparagine are substituted for one another. In the case of basic L-amino acids, we talk of conservative substitutions when L-arginine, L-lysine and L-histidine are substituted for one another. In the case of acidic L-amino acids, we talk of conservative substitutions when L-aspartic acid and L-glutamic acid are substituted for one another. In the case of L-amino acids containing hydroxyl groups, we talk of conservative substitutions when L-serine and L-threonine are substituted for one another.

Preferably the polypeptide contains at most two (2), at most three (3), at most four (4) or at most five (5) conservative amino acid substitutions in addition to the substitution at position 5 of SEQ ID NO: 2.

It is known that the terminal methionine may be removed during protein synthesis by enzymes that are intrinsic to the host, so-called aminopeptidases.

The isolated polynucleotides, which code for the citrate synthase variant, or portions thereof, can be used for producing recombinant strains of the genus *Corynebacterium*, preferably *Corynebacterium glutamicum*, which comprises the amino acid substitution at position 5 of the amino acid sequence of the citrate synthase polypeptide and which provide improved release of L-amino acids into the surrounding medium or accumulation of them inside the cell, compared with the starting or parent strain.

The initial strains preferably used are those which already possess the capacity to excrete at least 1 g/l, preferably at least 5 g/l, and more preferably at least 10 g/l of the desired L-amino acid into the surrounding nutrient medium.

A widely used method for incorporating mutations in genes of bacteria of the genus *Corynebacterium*, preferably of the species *Corynebacterium glutamicum*, is allelic substitution, which is also known as "gene replacement". In this technique, a DNA fragment that contains the mutation of interest is transferred into the desired strain and the mutation is incorporated in the chromosome of the desired strain by at least two recombination events or cross-over events or a gene sequence present in the strain in question is replaced by the mutated sequence.

In this method, the DNA fragment containing the mutation of interest may be located in a vector, preferably a plasmid, which preferably is not replicated by the strain that is to be provided with the mutation, or such replication is limited, i.e. occurs under selected culture conditions. A bacterium of the genus *Escherichia*, preferably of the species *Escherichia coli*, may be used as auxiliary or intermediate host, in which the vector can be replicated.

Examples of such plasmid vectors are the pK*mob and pK*mobsacB vectors, for example pK18mobsacB, described by Schäfer et al. (Gene 145, 69-73 (1994)), and the vectors described in WO 02/070685 and WO 03/014362. These vectors can replicate in *Escherichia coli* but not in *Corynebacterium*. Preferably, suitable vectors are those which contain a gene with conditionally negative dominant action for example the sacB gene (levansucrase gene) of for example *Bacillus* or the galK gene (galactose kinase gene) of for example *Escherichia coli*. "Gene with conditionally negative dominant action" means a gene which under certain conditions is disadvantageous, for example toxic to the host, but in other conditions does not have adverse effects on the host carrying the gene. These make it possible to select for recombination events in which the vector is eliminated from the chromosome.

Furthermore, Nakamura et al. (U.S. Pat. No. 6,303,383) described a temperature-sensitive plasmid for *Corynebacterium*, which can only replicate at temperatures below 31° C. It can also be used for the purposes of the invention.

The vector is then transferred into the *Corynebacterium* by conjugation, for example, by Schäfer's method (Journal of Bacteriology 172, 1663-1666 (1990)) or transformation, for example, by Dunican and Shivnan's method (Bio/Technology 7, 1067-1070 (1989)) or the method of Thierbach et al. (Applied Microbiology and Biotechnology 29, 356-362 (1988)). Optionally, the transfer of the DNA can also be achieved by ballistic methods (e.g. particle bombardment).

After homologous recombination by means of a first cross-over event producing integration and a suitable second cross-over event causing an excision in the target gene or in the target sequence, incorporation of the mutation is achieved and a recombinant bacterium is obtained. "Target gene" means the gene in which the desired substitution is to take place.

The strains obtained can be identified and characterized using, among others, the methods of Southern blotting hybridization, polymerase chain reaction and sequencing, the method of fluorescence resonance energy transfer (FRET) (Lay et al. Clinical Chemistry 43, 2262-2267 (1997)) or methods of enzymology.

This method was used by Schwarzer and Pühler (Bio/Technology 9, 84-87 (1991)) for incorporating a lysA allele carrying a deletion, and a lysA allele carrying an insertion, into the chromosome of *C. glutamicum* instead of the wild-type gene.

This method was used by Nakagawa et al. (EP 1108790) and Ohnishi et al. (Applied Microbiology and Biotechnology 58(2), 217-223 (2002)) for incorporating various mutations into the chromosome of *C. glutamicum* starting from the isolated alleles or polynucleotides. In this way, Nakagawa et al. succeeded in incorporating a mutation designated Val59Ala into the homoserine dehydrogenase gene (hom), a mutation designated Thr311Ile into the aspartate kinase gene (lysC or ask), a mutation designated Pro458Ser into the pyruvate carboxylase gene (pyc) and a mutation designated Ala213Thr into the glucose-6-phosphate-dehydrogenase gene (zwf) of *C. glutamicum* strains.

For inserting the mutation in the gltA gene into the chromosome by means of allelic substitution, it is possible to use a polynucleotide that codes for an amino acid sequence which has the amino acid substitution at position 5 of SEQ ID NO: 2, as shown in SEQ ID NO: 10, and possesses, upstream and downstream thereof, a nucleotide sequence with a length in each case of at least approx. 51 (cf. SEQ ID NO: 11 and 12) preferably in each case at least approx. 101 or 102 (cf. SEQ ID NO: 13 and 14), preferably in each case at least approx. 201 nucleobases (cf. SEQ ID NO: 15 and 16) and more preferably in each case at least approx. 500 or 498 nucleobases (cf. SEQ ID NO: 17 and 18) selected from SEQ ID NO: 9. The maximum length of the nucleotide sequence located upstream and downstream of the mutation is generally approx. 500, approx. 750, approx. 1000, approx. 1500, approx. 2000 to 2100 nucleobases. The nucleotide sequence located upstream of the mutation comprises, for example, the sequence between position 1 to 762 of SEQ ID NO: 9 or the sequence between position 1 to 1012 of SEQ ID NO: 25. The nucleotide sequence located downstream of the mutation comprises for example the sequence between position 766 to 2814 of SEQ ID NO: 9 or the sequence between position 1016 to 3314 of SEQ ID NO: 25. The total length of the polynucleotide used for the allelic substitution is accordingly at most approx. 1000, at most approx. 1500, at most approx. 2000, at most approx. 3000 or at most approx. 4000 to 4200 nucleobases.

Accordingly, the invention relates to a polynucleotide that comprises a nucleotide sequence which contains, from position 1 to 39, the nucleotide sequence corresponding to position 1 to 39 of SEQ ID NO: 11 and, from position 40 to 105, a nucleotide sequence that codes for the amino acid sequence according to SEQ ID NO: 12, having every proteinogenic amino acid except L-aspartic acid being contained at position 5.

In this context, the stated positions 1 to 39 of SEQ ID NO: 11 correspond to the stated positions 712 to 750 of SEQ ID NO: 9. The stated positions 40 to 105 of SEQ ID NO: 11 correspond to the stated positions 751 to 816 of SEQ ID NO: 9.

In one embodiment, the polynucleotide comprises the nucleotide sequence of SEQ ID NO: 11, with the codon corresponding to position 52 to 54 coding for every proteinogenic amino acid except L-aspartic acid.

In another embodiment the polynucleotide comprises the nucleotide sequence from position 712 to 816 of SEQ ID NO: 7.

Accordingly, the invention also relates to a polynucleotide that comprises a nucleotide sequence which comprises, from position 1 to 89, the nucleotide sequence corresponding to position 1 to 89 of SEQ ID NO: 13 and, from position 90 to 206, a nucleotide sequence which codes for the amino acid sequence according to SEQ ID NO: 14, having every proteinogenic amino acid except L-aspartic acid being contained at position 5.

In this context, the stated positions 1 to 89 of SEQ ID NO: 13 correspond to the stated positions 662 to 750 of SEQ ID NO: 9. The stated positions 90 to 206 of SEQ ID NO: 13 correspond to the stated positions 751 to 867 of SEQ ID NO: 9.

In one embodiment, the polynucleotide comprises the nucleotide sequence of SEQ ID NO: 13, with the codon corresponding to position 102 to 104 coding for every proteinogenic amino acid except L-aspartic acid.

In another embodiment, the polynucleotide comprises the nucleotide sequence from position 662 to 867 of SEQ ID NO: 7.

Accordingly, the invention also relates to a polynucleotide that comprises a nucleotide sequence which comprises, from position 1 to 189, the nucleotide sequence corresponding to position 1 to 189 of SEQ ID NO: 15 and, from position 190 to 405, a nucleotide sequence which codes for the amino acid sequence according to SEQ ID NO: 16, having every proteinogenic amino acid except L-aspartic acid being contained at position 5.

In this context, the stated positions 1 to 189 of SEQ ID NO: 15 correspond to the stated positions 562 to 750 of SEQ ID NO: 9. The stated positions 190 to 405 of SEQ ID NO: 15 correspond to the stated positions 751 to 966 of SEQ ID NO: 9.

In one embodiment, the polynucleotide comprises the nucleotide sequence of SEQ ID NO: 15, with the codon corresponding to position 202 to 204 coding for every proteinogenic amino acid except L-aspartic acid.

In another embodiment, the polynucleotide comprises the nucleotide sequence from position 562 to 966 of SEQ ID NO: 7.

Accordingly, the invention also relates to a polynucleotide that comprises a nucleotide sequence which comprises, from position 1 to 488, the nucleotide sequence corresponding to position 1 to 488 of SEQ ID NO: 17 and, from position 489 to 1001, a nucleotide sequence which codes for the amino acid sequence according to SEQ ID NO: 18, with every proteinogenic amino acid except L-aspartic acid being contained at position 5.

In this context, the stated positions 1 to 488 of SEQ ID NO: 17 correspond to the stated positions 263 to 750 of SEQ ID NO: 9. The stated positions 489 to 1001 of SEQ ID NO: 15 correspond to the stated positions 751 to 1263 of SEQ ID NO: 9.

In one embodiment, the polynucleotide comprises the nucleotide sequence of SEQ ID NO: 17, with the codon corresponding to position 501 to 503 coding for every proteinogenic amino acid except L-aspartic acid.

In another embodiment, the polynucleotide comprises the nucleotide sequence from position 263 to 1263 of SEQ ID NO: 7.

In another embodiment, the polynucleotide comprises the nucleotide sequence from position 9 to 1687 of SEQ ID NO: 31.

The invention also relates to vectors, preferably plasmids, comprising the stated polynucleotides.

The invention also relates to bacteria preferably of the genus *Escherichia*, more preferably of the species *Escherichia coli*, and *Corynebacterium*, more preferably of the species *Corynebacterium glutamicum*, comprising the stated vectors.

The invention also relates to strains of the genus *Corynebacterium*, preferably of the species *Corynebacterium glutamicum*, which have been produced using the polynucleotides or vectors comprising the polynucleotides.

It is also possible to insert the gltA allele at another site in the chromosome of *Corynebacterium glutamicum*. Possible examples are the sites or genes aecD, ccpA1, ccpA2, citA, citB, citE, fda, gluA, gluB, gluC, gluD, luxR, luxS, lysR1, lysR2, lysR3, menE, mqo, pck, pgi and poxB, as described in WO 03/04037. Other possibilities are, for example, intergenic regions, DNA of prophages, defective phages and phage components, as described in WO 04/069996.

The obtained recombinant strains display, relative to the initial strain or parent strain used, increased excretion or production of the desired amino acid in a fermentation process.

The L-lysine-excreting starting strains that can be used for the purposes of the invention possess, in addition to other properties, in particular a lysine-insensitive aspartate kinase.

"Lysine-insensitive aspartate kinase" means a polypeptide or protein with aspartate kinase activity (EC No. 2.7.2.4), which in comparison with the wild form, have lower sensitivity to inhibition by mixtures of lysine and threonine or mixtures of AEC (aminoethylcysteine) and threonine or lysine alone or AEC alone. Aspartate kinases of this kind are also called feedback-resistant or desensitized aspartate kinases. The nucleotide sequences coding for these desensitized aspartate kinases or aspartate kinase variants are also designated as $lysC^{FBR}$ alleles. Information on numerous $lysC^{FBR}$ alleles is available in public databases. The lysC-gene is also designated as the ask-gene by some authors.

The coding region of the wild-type lysC gene of *Corynebacterium glutamicum* corresponding to access number AX756575 of the NCBI database is shown in SEQ ID NO: 19 and the polypeptide encoded by this gene is shown in SEQ ID NO: 20. The nucleotide sequences located upstream of the 5' end and downstream of the 3' end of the coding region are also shown in SEQ ID NO: 21. SEQ ID NO: 20 corresponds to SEQ ID NO: 22.

The L-lysine-excreting bacteria preferably have a lysC allele, which codes for an aspartate kinase variant possessing the amino acid sequence of SEQ ID NO: 20, comprising one or more of the amino acid substitutions selected from the group:

a) LysC A279T (substitution of L-alanine at position 279 of the encoded aspartate kinase protein according to SEQ ID NO: 20 for L-threonine; see U.S. Pat. No. 5,688,671 and access numbers E06825, E06826, E08178 and 174588 to 174597), b) LysC A279V (substitution of L-alanine at position 279 of the encoded aspartate kinase protein according to SEQ ID NO: 20 for L-valine, see JP 6-261766 and access number E08179), c) LysC L297Q (substitution of L-leucine at position 297 of the encoded aspartate kinase protein according to SEQ ID NO: 20 for another proteinogenic amino acid, preferably L-glutamine; see DE 102006026328), d) LysC S301F (substitution of L-serine at position 301 of the encoded aspartate kinase protein according to SEQ ID NO: 20 for L-phenylalanine; see U.S. Pat. No. 6,844,176 and access number E08180), e) LysC S301Y (substitution of L-serine at position 301 of the encoded aspartate kinase protein according to SEQ ID NO: 20 for L-tyrosine, see Kalinowski et al. (Molecular and General Genetics 224, 317-324 (1990)) and access number X57226), f) LysC T308I (substitution of L-threonine at position 308 of the encoded aspartate kinase protein according to SEQ ID NO: 20 for L-isoleucine; see JP 6-261766 and access number E08181), g) LysC T311I (substitution of L-threonine at position 311 of the encoded aspartate kinase protein according to SEQ ID NO: 20 for L-isoleucine; see WO 00/63388 and U.S. Pat. No. 6,893,848), h) LysC S317A (substitution of L-serine at position 317 of the encoded aspartate kinase protein according to SEQ ID NO: 20 for L-alanine; see U.S. Pat. No. 5,688,671 and access number 174589), i) LysC R320G (substitution of L-arginine at position 320 of the encoded aspartate kinase protein according to SEQ ID NO: 20 for glycine; see Jetten et al. (Applied Microbiology and Biotechnology 43, 76-82 (995)) and access number L27125), j) LysC G345D (substitution of glycine at position 345 of the encoded aspartate kinase protein according to SEQ ID NO: 20 for L-aspartic acid; see Jetten et al. (Applied Microbiology and Biotechnology 43, 76-82 (995)) and access number L16848), k) LysC T380I (substitution of L-threonine at position 380 of the encoded aspartate kinase protein according to SEQ ID NO: 20 for L-isoleucine; see WO 01/49854 and access number AX192358), and l) LysC S381F (substitution of L-serine at position 381 of the encoded aspartate kinase protein according to SEQ ID NO: 20 for L-phenylalanine; see EP 0435132).

Strains comprise aspartate kinase variants comprising the amino acid substitution LysC T311I or at least one amino acid substitution selected from the group LysC A279T, LysC L297Q, LysC S317A, LysC T380I and LysC S381F.

Naturally it is also possible for insertion of the mutation in the gltA gene of the chromosome of a bacterium of the genus *Corynebacterium* to be carried out first, followed by insertion of one or more of the desired mutation(s) in the lysC gene of the strain in question.

In one embodiment, the described aspartate kinases are overexpressed in the *Corynebacterium* which comprises the amino acid substitution according to the invention in the gltA gene.

Overexpression means an increase in the intracellular concentration or activity of a ribonucleic acid, a protein or an enzyme compared with the initial strain (parent strain) or wild-type strain. Initial strain (parent strain) means the strain on which the measure leading to overexpression was carried out.

The increase in concentration or activity can be achieved, for example, by increasing the copy number of the corresponding polynucleotides chromosomally or extrachromosomally by at least one copy.

A widely used method of increasing the copy number comprises inserting the corresponding polynucleotide in a vector, preferably a plasmid, which is replicated by a coryneform bacterium. Suitable plasmid vectors are, for example, pZ1 (Menkel et al., Applied and Environmental Microbiology (1989) 64: 549-554) or the pSELF vectors described by Tauch et al. (Journal of Biotechnology 99, 79-91 (2002)). A review article on the subject of plasmids in *Corynebacterium glutamicum* can be found in Tauch et al. (Journal of Biotechnology 104, 27-40 (2003)).

Transposons, insertion elements (IS elements) or phages can also be used as vectors. Such genetic systems are stated for example in patent specifications U.S. Pat. No. 4,822,738, U.S. Pat. No. 5,804,414 and U.S. Pat. No. 5,804,414. Similarly, it is possible to use the IS element ISaB1 described in WO 92/02627 or the transposon Tn45 of plasmid pXZ10142 (cited in "Handbook of *Corynebacterium glutamicum*" (Publisher: L. Eggeling and M. Bott)).

Another widely used method for achieving overexpression is the technique of chromosomal gene amplification. In this method, at least one additional copy of the polynucleotide of interest is inserted in the chromosome of a coryneform bacterium. Such amplification techniques are described for example in WO 03/014330 or WO 03/040373.

Another method of achieving overexpression comprises operably linking the corresponding gene or allele with a promoter or an expression cassette. Suitable promoters for *Corynebacterium glutamicum* are described for example in FIG. 1 of the review article by Patek et al. (Journal of Biotechnology 104(1-3), 311-323 (2003)). The variants of the dapA promoter described by Vasicova et al. (Journal of Bacteriology 181, 6188-6191 (1999)), for example the promoter A25, can be used similarly. It is also possible to use the gap-promoter of *Corynebacterium glutamicum* (EP 06007373). Finally it is possible to use the sufficiently well-known promoters T3, T7, SP6, M13, lac, tac and trc described by Amann et al. (Gene 69(2), 301-315 (1988)) and Amann and Brosius (Gene 40(2-3), 183-190 (1985)). Such a Such a promoter can for example be inserted upstream of the gene in question, typically at a distance of about 1-500 nucleobases from the start codon.

As a result of the measures for overexpression, the activity or concentration of the corresponding polypeptide is increased by at least 10%, 25%, 50%, 75%, 100%, 150%, 200%, 300%, 400% or 500%, at most up to 1000% or 2000% relative to the activity or concentration of the polypeptide in the strain prior to the measure leading to overexpression.

In a further embodiment, the bacteria of the genus *Corynebacterium*, which preferably in addition comprises a polynucleotide that codes for a lysine-insensitive aspartate kinase variant, possess one or more of the characters selected from the group a) overexpressed polynucleotide (dapA gene), which codes for a dihydrodipicolinate synthase (DapA, EC No. 4.2.1.52), b) overexpressed polynucleotide (asd gene), which codes for an aspartate semialdehyde dehydrogenase (Asd, EC No. 1.2.1.11), c) overexpressed polynucleotide (lysA gene), which codes for a diaminopimelate decarboxylase (LysA, EC No. 4.1.1.20), d) overexpressed polynucleotide (aat gene), which codes for an aspartate aminotransferase (Aat, EC No. 2.6.1.1), e) overexpressed polynucleotide (lyse gene), which codes for a polypeptide with L-lysine exporting activity (LysE, Lysin Efflux Permease), f) switched-off or attenuated activity of malate dehydrogenase (Mdh, EC No. 1.1.1.37), g) switched-off or attenuated activity of malate-quinone oxidoreductase (Mqo, EC No. 1.1.99.16), h) overexpressed polynucleotide, which codes for a pyruvate carboxylase (Pyc, EC No. 6.4.1.1), and i) switched-off or attenuated activity of the E1p subunit of the pyruvate dehydrogenase complex (AceE, EC No. 1.2.4.1).

Characters a) to g) are preferred.

The known genes, for example, the wild-type genes, of *Escherichia coli* (Blattner et al., Science 277(5), 1453-1462 (1997)), *Bacillus subtilis* (Kunst et al., Nature 390 (6657), 249-256 (1997)), *Bacillus licheniformis* (Veith et al., Journal of Molecular Microbiology and Biotechnology 7 (4), 204-211 (2004)), *Mycobacterium tuberculosis* (Fleischmann et al., Journal of Bacteriology 1841, 5479-5490 (2004)), *Mycobacterium bovis* (Gamier et al., Proceedings of the National Academy of Sciences USA 100 (13), 7877-7882 (2003)), *Streptomyces coeliclor* (Redenbach et al., Molecular Microbiology 21 (1), 77-96 (1996)), *Lactobacillus acidophilus* (Altermann et al., Proceedings of the National Academy of Sciences USA 102 (11), 3906-3912 (2005)), *Lactobacillus johnsonii* (Pridmore et al., Proceedings of National Academy of Sciences USA 101 (8), 2512-2517 (2004)), *Bifidobacterium longum* (Schell et al., Proceedings of National Academy of Sciences USA 99 (22), 14422-14427 (2002)), and *Saccharomyces cerevisiae* can be used for overexpression of the listed genes or polynucleotides. The genomes of the wild-type forms of these bacteria are available in sequenced or annotated form. Preferably the endogenous genes or polynucleotides of the genus *Corynebacterium*, more preferably of the species *Corynebacterium glutamicum*, are used.

"Endogenous genes or polynucleotides" means the open reading frames (ORF), genes or alleles or their polynucleotides present in the population of a species.

The dapA gene of *Corynebacterium glutamicum* strain ATCC13032 is described for example in EP 0 197 335. The MC20 and MA16 mutations of the dapA promoter, as described in U.S. Pat. No. 6,861,246, can also be used, among others, for overexpression of the dapA gene of *Corynebacterium glutamicum*.

The asd gene of *Corynebacterium glutamicum* strain ATCC21529 is described for example in U.S. Pat. No. 6,927,046.

The lysA gene of *Corynebacterium glutamicum* ATCC13869 (*Brevibacterium lactofermentum*) is described for example in U.S. Pat. No. 6,090,597.

The aat gene of *Corynebacterium glutamicum* ATCC13032 is described for example in Kalinowski et al. (Journal of Biotechnology 104 (1-3), 5-25 (2003); see also access number NC_006958). There it is designated aspB gene. In U.S. Pat. No. 6,004,773 a gene coding for an aspartate aminotransferase is designated aspC. Marienhagen et al. (Journal of Bacteriology 187 (22), 7639-7646 (2005)) denote the aat gene as aspT gene.

The lysE gene of *Corynebacterium glutamicum* R127 is described for example in U.S. Pat. No. 6,858,406. Strain R127 is a restriction-defective mutant of ATCC13032 (Liebl et al., FEMS Microbiology Letters 65, 299-304 (1989)). The lysE gene of strain ATCC13032 used in U.S. Pat. No. 6,861,246 can be used similarly.

The pyc gene of *Corynebacterium glutamicum* of strain ATCC13032 is described for example in WO 99/18228 and WO 00/39305. Furthermore, alleles of the pyc gene can be used, such as are described in U.S. Pat. No. 6,965,021. The pyruvate carboxylases described in this patent specification possess one or more of the amino acid substitutions selected from the group: Pyc E153D (substitution of L-glutamic acid at position 153 for L-aspartic acid), Pyc A182S (substitution of L-alanine at position 182 for L-serine), Pyc A206S (substitution of L-alanine at position 206 for L-serine), Pyc H227R (substitution of L-histidine at position 227 for L-arginine), Pyc A455G (substitution of L-alanine at position 455 for glycine), and Pyc D1120E (substitution of L-aspartic acid at position 1120 for L-glutamic acid). Similarly, it is possible to use the pyc allele described in EP 1 108 790, which codes for a pyruvate carboxylase containing the amino acid substitution Pyc P458S (substitution of L-proline at position 458 for L-serine).

"Switched-off or attenuated activity" means reduction or switching-off of the intracellular activity or concentration of one or more enzymes or proteins in a microorganism, which is encoded by the corresponding polynucleotide or DNA.

For production of a strain in which the intracellular activity of a desired polypeptide is switched off, a deletion or insertion of at least one (1) nucleobase, preferably of one (1) or of two (2) nucleobases, is inserted in the coding region of the corresponding gene. It is also possible to delete at least one (1) or more codon(s) within the coding region. These measures lead to a shift of the reading frame (frame shift mutations) and therefore typically to the synthesis of a nonfunctional polypeptide. The introduction of a nonsense mutation by transversion or transition of at least one (1) nucleobase within the coding region has a similar effect. Owing to the stop codon that forms, there is premature termination of translation. The stated measures are preferably carried out in the region between the start codon and the penultimate coding codon, more preferably in the 5'-terminal portion of the coding region, which codes for the N-terminus of the polypeptide. If the total length of a polypeptide (measured as the number of chemically bound L-amino acids) is designated as 100%, then the portion of the amino acid sequence which, reckoned from the start amino acid L-formyl methionine, contains 80% of the subsequent L-amino acids, belongs to the N-terminus of the polypeptide.

Genetic measures for switching off malate-quinone oxidoreductase (Mqo) or reducing its expression are described for example in U.S. Pat. No. 7,094,106. U.S. Pat. No. 7,094,106 describes switching off the mqo gene by incorporating deletions or insertions of at least one base pair or substitutions generating a stop codon into the mqo gene, wherein reduction of expression was achieved by placing the expression of the mqo gene under the control of the *E. coli* trc promoter/LacI$^q$ repressor system.

Genetic measures for switching off malate dehydrogenase (Mdh) are described for example in WO 02/02778 (equivalent to U.S. Pat. No. 6,995,002). In WO 02/02778, the mdh gene was switched off by the insertion of a plasmid unable to replicate in *Corynebacterium glutamicum* comprising a central part of the coding region of the mdh gene into the host mdh gene by homologous recombination.

Genetic measures for switching off the E1p subunit (AceE) of the pyruvate dehydrogenase complex are described for example in EP 06119615 and in Schreiner et al. (Journal of Bacteriology 187(17), 6005-6018 (2005)). EP 06119615 and Schreiner et al. describe switching off the aceE gene by deleting a central part of the coding region of the aceE gene.

It is also possible, by suitable amino acid substitutions, to lower the catalytic property of the polypeptide in question.

In the case of malate-quinone oxidoreductase (Mqo) this can be achieved, as described in WO 06/077004, by preparing or using alleles of the mqo gene of SEQ ID NO: 23, which code for an Mqo variant that possesses the amino acid sequence of SEQ ID NO: 24 and contains one or more amino acid substitutions selected from the group a) substitution of the L-serine at position 111 for another proteinogenic amino acid, preferably L-phenylalanine or L-alanine, and b) substitution of the L-alanine at position 201 for another proteinogenic amino acid, preferably L-serine.

WO 06/077004 (equivalent to U.S. Pat. No. 7,214,526) describes an isolated coryneform bacterium mutant which comprises a gene encoding a polypeptide possessing malate quinone oxidoreductase enzyme activity, wherein the polypeptide comprises an amino acid sequence in which any proteinogenic amino acid except L-serine is present at position 111 or a comparable position.

Strains that comprise an mqo allele that codes for an Mqo variant which comprises the amino acid sequence of SEQ ID NO: 24, and contains L-phenylalanine at position 111, are preferred.

By the measures of switching-off or attenuation, the activity or concentration of the corresponding protein is generally lowered to 0 to 75%, 0 to 50%, 0 to 25%, 0 to 10% or 0 to 5% of the activity or concentration of the wild-type protein, or of the activity or concentration of the protein in the initial strain or parent strain.

The performance of the produced bacteria of the genus *Corynebacterium* or of the fermentation process using the produced bacteria with respect to one or more parameters selected from L-amino acid concentration (L-amino acid formed per volume), L-amino acid yield (L-amino acid formed per carbon source consumed), L-amino acid formation (L-amino acid formed per volume and time) and the specific L-amino acid formation (L-amino acid formed per cell dry mass or dry biomass and time or L-amino acid formed per cell protein and time) or other process variables and combinations thereof, is increased by at least 0.5%, at least 1%, at least 1.5% or at least 2% relative to the initial strain or parent strain or the fermentation process using them.

The produced bacteria of the genus *Corynebacterium* can be cultivated continuously, as described for example in PCT/EP2004/008882, or discontinuously in a batch process, a fed batch process or a repeated fed batch process, for the purpose of production of the desired L-amino acids. A summary of a general nature covering known culture methods is given in Chmiel's textbook (Bioprozesstechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)). PCT/EP2004/008882 (equivalent to WO 05/021772 and DE 10339847) describes a fermentation process comprising incubating and culturing in at least first nutrient medium a coryneform bacterium producing L-lysine, feeding continuously further nutrient media to the culture in one or several streams and removing at the same time culturing broth with a removal stream or streams corresponding to the feed streams, wherein over the entire period of time of feeding and removing concentration of the source of carbon is not more than 10 g/L and L-lysine is formed.

The culture medium or fermentation medium to be used matches the requirements of the particular strains. Descriptions of culture media for various microorganisms are given in "Manual of Methods for General Bacteriology" of the American Society for Bacteriology (Washington D.C., USA, 1981). The terms culture medium and fermentation medium or medium are interchangeable.

Sugars and carbohydrates, for example glucose, sucrose, lactose, fructose, maltose, molasses, sucrose-containing solutions from sugar beet or sugar cane production, starch, hydrolyzed starch and cellulose, oils and fats, for example soya oil, sunflower oil, peanut oil and coconut oil, fatty acids, for example palmitic acid, stearic acid and linoleic acid, alcohols, for example glycerol, methanol and ethanol and organic acids, for example acetic acid or lactic acid can be used as the carbon source. These materials can be used individually or as a mixture.

Organic nitrogen-containing compounds such as peptones, yeast extract, meat extract, malt extract, corn-steep liquor, soybean flour and urea or inorganic compounds such as ammonium sulfate, ammonium chloride, ammonium phosphate, ammonium carbonate and ammonium nitrate can be used as the nitrogen source. The nitrogen sources can be used individually or as a mixture.

Phosphoric acid, potassium dihydrogen phosphate or dipotassium hydrogen phosphate or the corresponding sodium-containing salts can be used as the phosphorus source.

The culture medium in addition contains salts, for example, in the form of chlorides or sulfates of metals such as sodium, potassium, magnesium, calcium and iron, for example magnesium sulfate or iron sulfate, which are necessary for growth. Finally, essential growth substances can be used, such as amino acids for example homoserine and vitamins for example thiamine, biotin or pantothenic acid, in addition to the aforementioned substances.

The aforementioned ingredients can be added to the culture as a single charge, or can be supplied in a suitable manner during cultivation.

Basic compounds such as sodium hydroxide, potassium hydroxide, ammonia or ammonia water, or acidic compounds such as phosphoric acid or sulfuric acid can be used in a suitable manner for pH control of the culture. The pH is generally adjusted to a value of 6.0 to 9.0, preferably 6.5 to 8. Antifoaming agents, for example polyglycol esters of fatty acids, can be used for controlling foaming. To maintain the stability of plasmids, suitable substances with selective action, for example antibiotics, can be added to the medium. To maintain aerobic conditions, oxygen or oxygen-containing gas mixtures, for example air, are fed into the culture. The use of liquids enriched with hydrogen peroxide is also possible. Optionally, the fermentation is carried out at excess pressure, for example at a pressure of 0.03 to 0.2 MPa. The temperature of the culture is normally in the range from 20° C. to 45° C. and preferably from 25° C. to 40° C. In batch processes, cultivation is continued until a maximum of the desired L-amino acid has formed at given conditions. This goal is normally reached within 10 hours to 160 hours. Longer cultivation times are possible with continuous processes. The activity of the bacteria leads to enrichment (accumulation) of the L-amino acid in the fermentation medium and/or in the bacterial cells.

Examples of suitable fermentation media are given inter alia in patent specifications U.S. Pat. No. 5,770,409, U.S. Pat. No. 5,840,551 and U.S. Pat. No. 5,990,350 or U.S. Pat. No. 5,275,940.

Methods for the determination of L-amino acids are known. The analysis can be carried out for example as described in Spackman et al. (Analytical Chemistry, 30, (1958), 1190) by anion-exchange chromatography followed by ninhydrin derivatization, or it can be carried out by reversed phase HPLC, as described by Lindroth et al. (Analytical Chemistry (1979) 51: 1167-1174).

Accordingly, the invention also relates to a method of production of an L-amino acid, wherein the following steps are carried out:

a) fermentation of the bacteria according to the invention in a suitable nutrient medium, b) accumulation of the L-amino acid in the nutrient medium or in the cells of said bacteria.

These steps may be followed by collecting of the L-amino acid that accumulated in the nutrient medium, in the fermentation broth or in the cells of the bacteria, in order to obtain a solid or a liquid product.

A fermentation broth means a fermentation medium or nutrient medium in which a microorganism has been cultivated for a certain time and at a certain temperature. The fermentation medium or the media used during fermentation contain(s) all substances or components for ensuring multiplication of the microorganism and formation of the desired amino acid.

At the end of fermentation, the resulting fermentation broth accordingly contains a) the biomass (cell mass) of the microorganism, formed as a result of multiplication of the cells of the microorganism, b) the desired L-amino acid that formed in the course of fermentation, such as L-lysine, L-valine or L-isoleucine, c) the organic by-products that formed in the course of fermentation, and d) the constituents of the fermentation medium or of the ingredients for example vitamins such as biotin, amino acids such as homoserine or salts such as magnesium sulfate, that were not consumed in the fermentation.

The organic by-products include substances which may be produced and may be excreted by the microorganisms used in the fermentation in addition to the particular desired organic compound. These also include sugars, for example trehalose.

In the case of the amino acids L-valine and L-isoleucine, isolation and purification, for example using one or more methods selected from the group comprising chromatographic techniques, crystallization techniques and the use of activated charcoal, is preferred, so that pure products are largely obtained, for example products with purity of $\geq$90 wt. % or $\geq$95 wt. %.

In the case of the amino acid L-lysine, essentially four different product forms are known.

One group of L-lysine-containing products comprises concentrated, aqueous, alkaline solutions of purified L-lysine (EP-B-0534865). Another group, as described for example in U.S. Pat. No. 6,340,486 and U.S. Pat. No. 6,465,025, comprises aqueous, acidic, biomass-containing concentrates of L-lysine-containing fermentation broths. Another group of solid products comprises powder or crystalline forms of purified or pure L-lysine, which may bey in the form of a salt, for example L-lysine monohydrochloride. Yet another group of solid product forms is described for example in EP-B-0533039. The product form described there contains, in addition to L-lysine, most of the ingredients employed during fermentation but not consumed, and possibly the biomass of the microorganism used at a proportion of >0%-100%.

In accordance with the various product forms, a great variety of methods is known for collecting, isolating or purifying the L-lysine from the fermentation broth, in order to produce an L-lysine-containing product or purified L-lysine.

Solid, pure L-lysine may be produced using methods of ion-exchange chromatography possibly with the use of activated charcoal and crystallization techniques. In this way we obtain the corresponding base or a corresponding salt, for example the monohydrochloride (Lys-HCl) or lysine sulfate ($Lys_2$-$H_2SO_4$).

A method of production of aqueous, basic L-lysine-containing solutions from fermentation broths is described in EP-B-0534865. In the method described there, the biomass is separated from the fermentation broth and discarded. A pH between 9 and 11 is established by means of a base, for example, sodium, potassium or ammonium hydroxide. The mineral constituents (inorganic salts) are separated from the broth after concentration and cooling, and either used as fertilizers or discarded.

In the case of methods for production of lysine using the bacteria, methods are preferred in which products are obtained that contain the constituents of the fermentation broth. These are used in particular as animal feed additives.

Depending on what is required, the biomass can be removed from the fermentation broth completely or partially by separation techniques such as centrifugation, filtration, decanting or a combination thereof, or it can be left in it completely. Optionally, the biomass or the fermentation broth containing the biomass is inactivated during a suitable process step, for example, by thermal treatment (heating) or by adding acid.

In one embodiment, the biomass is removed completely or almost completely, so that the finished product has a biomass content of zero (0%) or max. 30%, max. 20%, max. 10%, max. 5%, max. 1% or max. 0.1%. In another embodiment, the biomass is not removed or only a small proportion is removed, so that the finished product contains all the biomass (100%) or more than 70%, 80%, 90%, 95%, 99% or 99.9% biomass. In a method according to the invention, the biomass is accordingly removed in proportions from $\geq$0% to $\leq$100%.

Finally, the fermentation broth obtained after the fermentation can be adjusted to an acid pH with an inorganic acid such as hydrochloric acid, sulfuric acid or phosphoric acid or organic acid such as propionic acid, before or after complete or partial removal of the biomass (GB 1,439,728 or EP 1 331 220). It is also possible to acidify the fermentation broth still containing all the biomass. Finally, the broth can also be stabilized by adding sodium bisulfite ($NaHSO_3$, GB 1,439, 728) or another salt for example ammonium, alkali or alkaline-earth salt of sulfurous acid.

In separating the biomass, any organic or inorganic solids contained in the fermentation broth are removed partially or completely. The organic by-products dissolved in the fermentation broth and the dissolved, unconsumed constituents of the fermentation medium (ingredients) remain in the product at least partially (>0%), preferably to at least 25%, preferably to at least 50% and more preferably to at least 75%. Optionally, these also remain in the product completely (100%) or almost completely, i.e. >95% or >98% or over 99%. If a product in this sense contains at least a proportion of the constituents of the fermentation broth, it is also described with the term "product based on fermentation broth".

Then the broth is dewatered or thickened or concentrated using known methods, e.g. by means of a rotary evaporator, thin-film evaporator, falling-film evaporator, by reverse osmosis or by nanofiltration. This concentrated fermentation broth can then be processed by techniques of freeze drying, spray drying, spray granulation or by other methods, for example the circulating fluidized bed as described in PCT/EP2004/006655, to pourable products and preferably to a fine powder or preferably coarse granules. If required, a desired product can be isolated from the granules thus obtained by sieving or dust separation.

It is also possible for the fermentation broth to be dried directly, i.e. without previous concentration, by spray drying or spray granulation.

"Pourable" means powders which, from a series of glass discharge vessels with outlet openings of different sizes, are discharged freely from the vessel with the 5 mm (millimeter) opening (Klein: Seifen, Öle, Fette, Wachse 94, 12 1968)).

"Fine" means a powder having mainly (>50%) a grain size of 20 to 200 μm diameter. "Coarse" means a product having mainly (>50%) a grain size from 200 to 2000 μm diameter.

Grain size can be determined using methods of laser diffraction spectrometry. The relevant methods are described in the textbook on "Particle Size Measurement in Laboratory Practice" by R. H. Müller and R. Schuhmann, Wissenschaftliche Verlagsgesellschaft Stuttgart (1996) or in the textbook "Introduction to Particle Technology" by M. Rhodes, Publ. Wiley & Sons (1998).

The pourable, fine powder can be converted by suitable compaction or granulation techniques to a coarse, storable and largely dust-free product with good pourability.

The term "dust-free" means that the product only contains a small proportion (<5%) of particles with grain size under 100 μm diameter.

"Storable", in the sense of this invention, means a product that can be stored in cool, dry conditions for at least one (1) year or longer, preferably at least 1.5 years or longer, more preferably two (2) years or longer, without any substantial loss (max. 5%) of the particular amino acid.

The invention further relates to a method of manufacturing an L-lysine comprising product, which is described in broad outline in DE 102006016158, and in which the fermentation broth obtained using the microorganisms according to the invention, from which the biomass has been optionally separated completely or partially, is further processed, by carrying out a process that comprises at least the following steps:

a) the pH is lowered to 4.0-5.2, preferably 4.9-5.1, by adding sulfuric acid, and a sulfate/L-lysine molar ratio of 0.85-1.2, preferably 0.9-1.0, more preferably >0.9 to <0.95, is established in the broth, if necessary by adding one or more additional sulfate-containing compound(s) and b) the mixture thus obtained is concentrated by dewatering, and optionally granulated, optionally with one or both of the following measures being carried out before step a):

c) measurement of the sulfate/L-lysine molar ratio for determining the required amount of sulfate-containing compound(s)

d) addition of a sulfate-containing compound selected from the group comprising ammonium sulfate, ammonium hydrogensulfate and sulfuric acid in suitable proportions.

Optionally, also prior to step b), a salt of sulfurous acid, preferably an alkali metal hydrogensulfite, and more preferably sodium hydrogensulfite, at a concentration of 0.01-0.5 wt. %, preferably 0.1-0.3 wt. %, more preferably 0.1-0.2 wt. % relative to the fermentation broth is used.

DE 102006016158 (equivalent to US2007082031 and WO 07/042363) describes relatively light and thermally stable granulated fermentation-broth-based animal feed additives having a high content of L-lysine and low-loss methods for production the additives from broths obtained by fermentation.

As preferred sulfate-containing compounds in the sense of the aforementioned process steps we may mention in particular ammonium sulfate and/or ammonium hydrogensulfate or corresponding mixtures of ammonia and sulfuric acid and sulfuric acid itself.

The sulfate/L-lysine molar ratio V is calculated from the formula: $V=2\times[SO_4^{2-}]/[L\text{-lysine}]$. This formula takes account of the fact that the $SO_4^{2-}$ anion, or sulfuric acid, is divalent. A ratio $V=1$ means that the $Lys_2\text{-}H_2SO_4$ is of stoichiometric composition, whereas at a ratio of $V=0.9$ there is a 10% sulfate deficit and at a ratio of $V=1.1$ there is a 10% sulfate excess.

During granulating or compacting the usual organic or inorganic auxiliaries, or carriers such as starch, gelatin, cellulose derivatives or similar substances, as are usually employed in the processing of foodstuffs or animal feed as binders, gelling agents or thickeners, or other substances for example silicic acids, silicates (EP0743016A) or stearates may be used.

Treatment the surface of the obtained granules with oils, as described in WO 04/054381 may be used. The oils used can be mineral oils, vegetable oils or mixtures of vegetable oils. Examples of such oils are soya oil, olive oil, soya oil/lecithin mixtures. Similarly, silicone oils, polyethylene glycols or hydroxyethyl cellulose are also suitable. Treatment of the surfaces with the aforesaid oils gives increased abrasion resistance of the product and a reduction in the proportion of dust. The content of oil in the product is 0.02-2.0 wt. %, preferably 0.02-1.0 wt. %, and more preferably 0.2-1.0 wt. % relative to the total amount of the feed additive.

Products are preferred having a proportion of ≧97 wt. % of a grain size from 100 to 1800 μm or a proportion of ≧95 wt. % of a grain size from 300 to 1800 μm diameter. The proportion of dust, i.e. particles with a grain size<100 μm, is preferably >0 to 1 wt. %, max. 0.5 wt. % being more preferred.

Alternatively, the product can also be coated with an organic or inorganic carrier that is known and usual in animal feed processing, for example silicic acids, silicates, grits, bran, meal or flour, starch, sugars or other substances and/or mixed and stabilized with usual thickeners or binders. Examples of applications and the methods employed are described in the literature (Die Mühle+Mischfuttertechnik 132 (1995) 49, page 817).

Finally, using coating processes with film-forming agents such as metal carbonates, silicic acids, silicates, alginates, stearates, starches, gums and cellulose ethers, as described in DE-C-4100920, the product can be brought to a state in which it is stable against digestion in animal stomachs preferably the stomach of ruminants. DE4100920 (equivalent to U.S. Pat. No. 5,279,832 and EP 0495349) describes an active-substance preparation for oral administration, preferably for ruminants, comprising an active-substance core comprising at least one biologically active substance and a coating around this core which delays the release of the core after oral administration due to its geometrical shape as well as a method of preparing an accordingly shaped core pellet by coating.

For establishing a desired L-lysine concentration in the product, depending on requirements, the L-lysine can be added during the process in the form of a concentrate or optionally a substantially pure substance or salt thereof in liquid or solid form. These can be added individually or as mixtures to the fermentation broth obtained or concentrated, or alternatively during the drying or granulation process.

The invention relates further to a method of production of a solid lysine-containing product, as described in broad outline in US 20050220933, and which comprises the processing of the fermentation broth obtained using the microorganisms according to the invention, in the following steps:

a) filtration of the fermentation broth, preferably with a membrane filter, so that a biomass-containing sludge and a filtrate are obtained, b) concentration of the filtrate, preferably so that a solids content of 48-52 wt. % is obtained, c) granulation of the concentrate obtained in step b), preferably at a temperature from 50° C. to 62° C., and d) coating of the granules obtained in c) with one or more coating agent(s)

For the coating in step d), it is preferable to use coating agents that are selected from the group comprising d1) the biomass obtained in step a)

d2) a compound containing L-lysine, preferably selected from the group comprising L-lysine hydrochloride or L-lysine sulfate, d3) an essentially L-lysine-free material with L-lysine content<1 wt. %, preferably <0.5 wt. %, preferably selected from the group consisting of starch, carrageenan, agar, silicic acids, silicates, grits, bran and meal, and d4) a water-repellent substance, preferably selected from the group consisting of oils, polyethylene glycols and liquid paraffins.

The content of L-lysine is adjusted to a desired value by the measures corresponding to steps d1) to d4), preferably d1) to d3).

In the production of L-lysine-containing products, the ratio of the ions is preferably adjusted so that the molar ionic ratio according to the following formula $$2\times[SO_4^{2-}]+[Cl^-]-[NH_4^+]-[Na^-]-[K^+]-2\times[Mg^{2+}]- 2\times[Ca^{2+}]/[L\text{-Lys}] \text{ is } 0.68\text{-}0.95,$$

preferably 0.68-0.90, as described by Kushiki et al. in US 20030152633.

In the case of lysine, the solid product based on fermentation broth produced in this way has a lysine content (lysine base) from 10 wt. % to 70 wt. % or 20 wt. % to 70 wt. %, preferably 30 wt. % to 70 wt. % and more preferably from 40 wt. % to 70 wt. % based on the dry mass of the product. Maximum contents of lysine base of 71 wt. %, 72 wt. %, 73 wt. % are also possible. The water content of the L-lysine-containing, solid product is up to 5 wt. %, preferably up to 4 wt. %, and more preferably less than 3 wt. %. Having generally described this invention, a further understanding can be obtained by reference to certain specific examples which are provided herein for purposes of illustration only, and are not intended to be limiting unless otherwise specified.

EXAMPLES

Example 1

Sequencing of the gltA Gene of the Strain DM678

The strain *Corynebacterium glutamicum* DM678 (U.S. Pat. No. 6,861,246) is a lysine-producing strain developed by mutagenesis and screening. It is auxotrophic for L-threonine and L-methionine-sensitive. The strain was deposited at the Deutsche Sammlung für Mikroorganismen und Zellkulturen (DSMZ, Braunschweig, Germany) as DSM12866.

The method of Eikmanns et al. (Microbiology 140: 1817-1828 (1994)) was used to isolate chromosomal DNA from the strain DM678. The polymerase chain reaction was used to amplify a DNA segment which harbors the gltA gene. The following oligonucleotides were used as primers for this:

```
gltA_XL-A1 (SEQ ID NO: 27):
5' tgagttctattggcgtgacc 3' gltA_XL-E1 (SEQ ID NO: 28):
5' ttcgccaacgatgatgtcag 3'
```

The depicted primers were synthesized by MWG Biotech (Ebersberg, Germany). They make it possible to amplify a DNA segment which was about 1.8 kb long and harbors the gltA gene. The primer gltA_XL-A1 binds to the region corresponding to position 490 to 509 of the strand complementary to SEQ ID NO: 3 (and SEQ ID NO: 7). The primer gltA_XL-E1 binds to the region corresponding to position 2266 to 2247 of the strand shown in SEQ ID NO: 3 (and SEQ ID NO: 7).

The PCR reaction was carried out using the Phusion high fidelity DNA polymerase (New England Biolabs, Frankfurt, Germany). The reaction mixture was made up as specified by the manufacturer and contained 10 µl of the 5× Phusion HF buffer supplied, deoxynucleoside triphosphates each in a concentration of 200 µM, primers in a concentration of 0.5 µM, approximately 50 ng of template DNA and 2 units of Phusion polymerase in a total volume of 50 µl. The volume was adjusted to 50 µl by adding $H_2O$.

The PCR mixture was first subjected to an initial denaturation at 98° C. for 30 seconds. This was followed by a denaturation step at 98° C. for 20 seconds, repeated 35×, a step for binding the primers to the introduced DNA at 60° C. for 20 seconds and the extension step to extend the primers at 72° C. for 60 seconds. After the final extension step at 72° C. for 5 minutes, the PCR mixture was subjected to an agarose gel electrophoresis (0.85% agarose). A DNA fragment about 1.8 kb long was identified, isolated from the gel and purified using the QIAquick gel extraction kit from Qiagen (Hilden, Germany).

The nucleotide sequence of the amplified DNA fragment or PCR product was determined by Agowa (Berlin, Germany).

The nucleotide sequence of the coding region of the gltA allele from the strain DM678 contains thymine as nucleobase at position 14. The wild-type gene (see SEQ ID NO: 1) contains adenine as nucleobase at this position. This adenine-thymine transversion leads to an amino acid exchange from aspartate to valine at position 5 of the resulting amino acid sequence. This mutation is referred to hereinafter as gltAD5V. The allele gltAD5V is depicted in SEQ ID NO: 5, and the amino acid sequence of the protein which was revealed with the aid of the Patentin program is depicted in SEQ ID NO: 6.

Example 2

Construction of the Exchange Vector pK18mobsacB_gltAD5V

The polymerase chain reaction was used to amplify a DNA fragment which harbors part of the upstream region of the gltA gene and part of the coding region which contains the gltAD5V mutation. The chromosomal DNA obtained in example 1 from DM678 was used as template. The following oligonucleotides were selected as primers for the PCR:

```
gltA_1.p (SEQ ID NO: 29):
5' CCGTCGACAATAGCCTGAA 3' gltA_2.p (SEQ ID NO: 30):
5' CC-GAATTC-TTCGAGCATCTCCAGAAC 3'
```

They were synthesized by MWG Biotech (Ebersberg, Germany) and make it possible to amplify a DNA segment about 1.7 kb long comprising 832 bp of the upstream region and nucleotides 1-855 bp of the coding region of the gltA gene from DM678.

The primer gltA__1.p binds to the region corresponding to position 169 to 187 of the strand complementary to SEQ ID NO: 25. Nucleotides 9 to 26 of the primer gltA__2.p bind to the region corresponding to position 1855 to 1838 of the strand shown in SEQ ID NO: 25. In addition, the primer gltA__1.p contains the native cleavage site of the restriction enzyme SalI, and the primer gltA__2.p contains the sequence of the cleavage site of the restriction enzyme EcoRI, which are each marked by underlining in the nucleotide sequence depicted above.

The PCR reaction was carried out using the Phusion high fidelity DNA polymerase (New England Biolabs, Frankfurt, Germany). The reaction mixture had the composition described above. The PCR was carried out as described above. The nucleotide sequence of the amplicon about 1.7 kb long is depicted in SEQ ID NO: 31.

The amplicon was treated with the restriction endonucleases SalI and EcoRI and identified by electrophoresis in a 0.8% agarose gel. It was subsequently isolated from the gel and purified using the QIAquick gel extraction kit from Qiagen.

The DNA fragment purified in this way contains the described gltAD5V mutation and has ends compatible with DNA cut with SalI and EcoRI (respectively gltAD5V fragment and gltA' in the FIGURE). It was subsequently cloned into the mobilizable vector pK18mobsacB described by Schäfer et al. (Gene, 145, 69-73 (1994)) in order to make an allelic or mutation substitution possible. For this purpose, pK18mobsacB was digested with the restriction enzymes EcoRI and SalI, and the ends were dephosphorylated with alkaline phosphatase (alkaline phosphatase, Boehringer Mannheim, Germany). The vector prepared in this way was mixed with the gltAD5V fragment, and the mixture was treated with the ready-to-go T4 DNA ligase kit (Amersham-Pharmacia, Freiburg, Germany).

Subsequently, the *E. coli* strain S17-1 (Simon et al., Bio/Technologie 1: 784-791, 1993) was transformed with the ligation mixture (Hanahan, In. DNA cloning. A practical approach. Vol. 1. ILR-Press, Cold Spring Harbor, N.Y., 1989). Selection of plasmid-harboring cells took place by plating out the transformation mixture on LB agar (Sambrook et al., Molecular Cloning: a laboratory manual. 2nd Ed. Cold Spring Harbor, N.Y., 1989) which had been supplemented with 25 mg/l kanamycin.

Plasmid DNA was isolated from a transformant using the QIAprep spin miniprep kit from Qiagen and checked by restriction cleavage with the enzymes SalI and EcoRI and subsequent agarose gel electrophoresis. The plasmid was called pK18mobsacB_gltAD5V and is depicted in the FIGURE. The abbreviations and designations used have the following meaning. The stated numbers of base pairs are approximations obtained within the scope of the reproducibility of measurements.

| | |
|---|---|
| Kan: | kanamycin-resistance gene |
| SalI: | cleavage site of the restriction enzyme SalI |
| EcoRI: | cleavage site of the restriction enzyme EcoRI |
| gltA': | cloned DNA fragment containing the gltAD5V mutation |
| sacB: | sacB gene |
| RP4-mob: | mob region with the origin of replication for transfer (oriT) |
| oriV: | origin of replication V |

Example 3

Incorporation of the gltAD5V Mutation into the Strain *Corynebacterium glutamicum* DM1797

The intention was to introduce the gltAD5V mutation into the strain *Corynebacterium glutamicum* DM1797. The strain DM1797 was an aminoethylcysteine-resistant mutant of *Corynebacterium glutamicum* ATCC13032 and described in PCT/EP/2005/012417. It was deposited under the number DSM16833 at the Deutsche Sammlung für Mikroorganismen und Zellkulturen (DSMZ, Braunschweig, Germany).

The vector pK18mobsacB_gltAD5V described in example 2 was transferred by conjugation according to the protocol of Schäfer et al. (Journal of Microbiology 172: 1663-1666 (1990)) into the *C. glutamicum* strain DM1797. The vector was incapable of independent replication in DM1797 and was retained in the cell only if it was integrated into the chromosome as the result of a recombination event. Selection of transconjugants, i.e. of clones having integrated pK18mobsacB_gltAD5V, took place by plating out the conjugation mixture on LB agar which had been supplemented with 25 mg/l kanamycin and 50 mg/l of nalidixic acid. Kanamycin-resistant transconjugants were subsequently streaked onto LB agar plates supplemented with kanamycin (25 mg/l) and incubated at 33° C. for 24 hours. Mutants in which, as a result of a second recombination event, excision of the plasmid had taken place were selected by culturing the clones nonselectively in LB liquid medium for 30 hours, then streaking onto LB agar, which had been supplemented with 10% sucrose, and incubating at 33° C. for 24 hours.

The plasmid pK18mobsacB_gltAD5V contains, just like the initial plasmid pK18mobsacB, besides the kanamycin-resistance gene a copy of the sacB gene which codes for the levan sucrase from *Bacillus subtilis*. The sucrose-inducible expression of the sacB gene leads to the formation of levan sucrase which catalyzes the synthesis of the product levan which is toxic for *C. glutamicum*. Thus, the only clones to grow on sucrose-supplemented LB agar were those in which the integrated pK18mobsacB_gltAD5V has been excised as the result of a second recombination event. Depending on the position of the second recombination event in relation to the site of mutation, the excision is associated with allelic substitution or incorporation of the mutation instead, or the original copy remains in the host's chromosome.

A clone in which the desired exchange, i.e. the incorporation of the gltAD5V mutation, had taken place was then sought. For this purpose, the sequence of the gltA gene was determined for 10 clones with the phenotype "growth in the presence of sucrose" and "non-growth in the presence of kanamycin". In this way, a clone harboring the gltAD5V mutation was identified. This strain was designated *C. glutamicum* DM1797_gltAD5V.

Example 4

Production of L-lysine

The strain DM1797_gltAD5V obtained in example 3 and the initial strain DM1797 were cultured in a nutrient medium suitable for producing lysine, and the lysine content in the culture supernatant was determined.

For this purpose, the clones were initially grown on brain-heart agar plates (Merck, Darmstadt, Germany) at 33° C. for 24 hours. These agar plate cultures were each used for inoculation of a preculture (10 ml of medium in a 100 ml Erlenmeyer flask). The medium MM was used as medium for the precultures. The precultures were incubated at 33° C. and 240 rpm on a shaker for 24 hours. Each of these precultures was used to inoculate a main culture, so that the initial OD (660 nm) of the main culture was 0.1 OD. The medium MM was likewise used for the main cultures.

| Medium MM | |
|---|---|
| CSL | 5 g/l |
| MOPS | 20 g/l |
| Glucose (autoclaved separately) | 50 g/l |

Salts:

| | |
|---|---|
| $(NH_4)_2SO_4)$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterilized by filtration) | 0.3 mg/l |
| Thiamine * HCl (sterilized by filtration) | 0.2 mg/l |
| $CaCO_3$ | 25 g/l |

CSL (corn steep liquor), MOPS (morpholinopropanesulfonic acid) and the salt solution were adjusted to pH 7 with aqueous ammonia and autoclaved. The sterile substrate and vitamin solutions, and the dry autoclaved $CaCO_3$, were then added.

Culturing took place in volumes of 10 ml which were present in 100 ml Erlenmeyer flasks with baffles. The temperature was at 33° C., the number of revolutions was 250 rpm and the humidity was 80%.

After 48 hours, the optical density (OD) was determined at a measurement wavelength of 660 nm using a Biomek 1000 (Beckmann Instruments GmbH, Munich). The amount of lysine formed was determined using an amino acid analyzer from Eppendorf-BioTronik (Hamburg, Germany) by ion-exchange chromatography and post-column derivatization with ninhydrin detection.

TABLE 1

| Strain | OD (660) | Lysine HCl (g/l) |
|---|---|---|
| DM1797 | 11.9 | 4.8 |
| DM1797_gltAD5V | 11.2 | 5.3 |

Example 5

Incorporation of the gltAD5V Mutation into the Strain *Brevibacterium lactofermentum* FERM BP-1763

It was intended to introduce the gltAD5V mutation into the strain *Brevibacterium lactofermentum* FERM BP-1763. The strain FERM BP-1763 is a mycophenolic acid-resistant valine producer (U.S. Pat. No. 5,188,948). It is auxotrophic for L-isoleucine and L-methionine.

The vector pK18mobsacB_gltAD5V described in example 2 was transferred by conjugation according to the protocol of Schäfer et al. (Journal of Microbiology 172: 1663-1666 (1990)) into the strain FERM-BP-1763. The vector was incapable of independent replication in FERM BP-1763 and was retained in the cell only if it was integrated into the chromosome as the result of a recombination event. Selection of transconjugants, i.e. of clones having integrated pK18mobsacB_gltAD5V, took place by plating out the conjugation mixture on LB agar which had been supplemented with 25 mg/l kanamycin and 50 mg/l of nalidixic acid. Kanamycin-resistant transconjugants were subsequently streaked onto LB agar plates supplemented with kanamycin (25 mg/l) and incubated at 33° C. for 24 hours. Mutants in which, as a result of a second recombination event, excision of the plasmid had taken place were selected by culturing the clones nonselectively in LB liquid medium for 30 hours, then streaking onto LB agar, which had been supplemented with 10% sucrose, and incubating at 33° C. for 24 hours.

The plasmid pK18mobsacB_gltAD5V contained, just like the initial plasmid pK18mobsacB, besides the kanamycin-resistance gene a copy of the sacB gene which coded for the levan sucrase from *Bacillus subtilis*. The sucrose-inducible expression of the sacB gene led to the formation of levan sucrase which catalyzes the synthesis of the product levan which was toxic for *C. glutamicum*. Thus, the only clones to grow on sucrose-supplemented LB agar were those in which the integrated pK18mobsacB_gltAD5V has been excised as the result of a second recombination event. Depending on the position of the second recombination event in relation to the site of mutation, the excision was associated with allelic substitution or incorporation of the mutation instead, or the original copy remains in the host's chromosome.

A clone in which the desired exchange, i.e. the incorporation of the gltAD5V mutation, had taken place was then sought. For this purpose, the sequence of the gltA gene was determined for 10 clones with the phenotype "growth in the presence of sucrose" and "non-growth in the presence of kanamycin". In this way, a clone harboring the gltAD5V mutation was identified. This strain was designated *C. glutamicum* FERM BP-1763_gltAD5V.

Example 6

Production of L-valine

The strain FERM BP-1763_gltAD5V obtained in example 5 and the initial strain FERM BP-1763 were cultured in a nutrient medium suitable for producing valine, and the valine content in the culture supernatant was determined.

For this purpose, the clones were initially grown on brain-heart agar plates (Merck, Darmstadt, Germany) at 33° C. for 24 hours. These agar plate cultures were each used for inoculation of a preculture (10 ml of medium in a 100 ml Erlenmeyer flask).

The medium CgIII (2.5 g/l NaCl, 10 g/l Bacto peptone, 10 g/l Bacto yeast extract, pH 7.4, 20 g/l glucose (autoclaved separately) was used for the precultures. The precultures were incubated at 33° C. and 240 rpm on a shaker for 24 hours. Each of these precultures was used to inoculate a main culture, so that the initial OD (660 nm) of the main culture was 0.1 OD. The medium MM was likewise used for the main cultures.

| Medium MM | |
|---|---|
| CSL | 5 g/l |
| MOPS | 20 g/l |
| Glucose (autoclaved separately) | 50 g/l |

Salts:

| | |
|---|---|
| (NH$_4$)$_2$SO$_4$) | 25 g/l |
| KH$_2$PO$_4$ | 0.1 g/l |
| MgSO$_4$ * 7 H$_2$O | 1.0 g/l |
| CaCl$_2$ * 2 H$_2$O | 10 mg/l |
| FeSO$_4$ * 7 H$_2$O | 10 mg/l |
| MnSO$_4$ * H$_2$O | 5.0 mg/l |
| Isoleucine (sterilized by filtration) | 0.1 g/l |
| Methionine (sterilized by filtration) | 0.1 g/l |
| Leucine (sterilized by filtration) | 0.1 g/l |
| Thiamine * HCl (sterilized by filtration) | 0.2 mg/l |
| CaCO$_3$ | 25 g/l |

CSL (corn steep liquor), MOPS (morpholinopropanesulfonic acid) and the salt solution were adjusted to pH 7 with aqueous ammonia and autoclaved. The sterile substrate and vitamin solutions, and the dry autoclaved CaCO$_3$, were then added.

Culturing took place in volumes of 10 ml which were present in 100 ml Erlenmeyer flasks with baffles. The temperature was at 33° C., the number of revolutions was 250 rpm and the humidity was 80%.

After 48 hours, the optical density (OD) was determined at a measurement wavelength of 660 nm using the Biomek 1000 (Beckmann Instruments GmbH, Munich). The amount of valine formed was determined using an amino acid analyzer from Eppendorf-BioTronik (Hamburg, Germany) by ion-exchange chromatography and post-column derivatization with ninhydrin detection.

TABLE 2

| Strain | OD (660) | Valine (g/l) |
|---|---|---|
| FERM BP-1763 | 8.4 | 11.9 |
| FERM BP-1763_gltAD5V | 7.8 | 12.6 |

German patent application 102006032634.2, filed Jul. 13, 2006, and U.S. provisional application 60/830,331, filed Jul. 13, 2006, are incorporated herein by reference.

Numerous modification and variations on the present invention are possible in light of the above teachings. It is therefore to be understood that within the scope of the appended claims, the invention may be practiced otherwise than as specifically described herein.

The invention claimed is:

1. An isolated polynucleotide, encoding a polypeptide comprising the amino acid sequence of SEQ ID NO: 2, wherein L-aspartic acid at position 5 of the amino acid sequence is replaced by L-valine, and wherein the polypeptide possesses a citrate synthase activity.

2. The isolated polynucleotide of claim 1, wherein the isolated polynucleotide comprises the nucleotide sequence of SEQ ID NO: 5.

3. A vector comprising the polynucleotide as claimed in claim 1.

4. A bacterium that has been transformed with the vector as claimed in claim 3, wherein the bacterium is *Corynebacterium glutamicum*.

5. A bacterium of *Corynebacterium glutamicum*, which comprises the polynucleotide as claimed in claim 1.

6. A recombinant bacterium of *Corynebacterium glutamicum* comprising a polynucleotide that codes for a polypeptide possessing a citrate synthase activity, wherein the polypeptide comprises the amino acid sequence of SEQ ID NO: 2 in which L-aspartic acid at position 5 is substituted with L-valine.

7. The recombinant bacterium as claimed in claim 6, wherein the polynucleotide comprises the nucleotide sequence of SEQ ID NO: 5.

* * * * *

SEQUENCE LISTING

```
<160> NUMBER OF SEQ ID NOS: 32

<210> SEQ ID NO 1
<211> LENGTH: 1314
<212> TYPE: DNA
<213> ORGANISM: Corynebacterium glutamicum
<220> FEATURE:
<221> NAME/KEY: CDS
<222> LOCATION: (1)..(1311)
<223> OTHER INFORMATION: gltA-Wildtype-Gene
<220> FEATURE:
<221> NAME/KEY: misc_feature
<222> LOCATION: (13)..(15)

<400> SEQUENCE: 1 atg ttt gaa agg gat atc gtg gct act gat aac aac aag gct gtc ctg      48
Met Phe Glu Arg Asp Ile Val Ala Thr Asp Asn Asn Lys Ala Val Leu
1               5                   10                  15 cac tac ccc ggt ggc gag ttc gaa atg gac atc atc gag gct tct gag      96
His Tyr Pro Gly Gly Glu Phe Glu Met Asp Ile Ile Glu Ala Ser Glu
                20                  25                  30 ggt aac aac ggt gtt gtc ctg ggc aag atg ctg tct gag act gga ctg     144
Gly Asn Asn Gly Val Val Leu Gly Lys Met Leu Ser Glu Thr Gly Leu
            35                  40                  45 atc act ttt gac cca ggt tat gtg agc act ggc tcc acc gag tcg aag     192
Ile Thr Phe Asp Pro Gly Tyr Val Ser Thr Gly Ser Thr Glu Ser Lys
        50                  55                  60 atc acc tac atc gat ggc gat gcg gga atc ctg cgt tac cgc ggc tat     240
Ile Thr Tyr Ile Asp Gly Asp Ala Gly Ile Leu Arg Tyr Arg Gly Tyr
65                  70                  75                  80 gac atc gct gat ctg gct gag aat gcc acc ttc aac gag gtt tct tac     288
Asp Ile Ala Asp Leu Ala Glu Asn Ala Thr Phe Asn Glu Val Ser Tyr
                85                  90                  95 cta ctt atc aac ggt gag cta cca acc cca gat gag ctt cac aag ttt     336
Leu Leu Ile Asn Gly Glu Leu Pro Thr Pro Asp Glu Leu His Lys Phe
                100                 105                 110 aac gac gag att cgc cac cac acc ctt ctg gac gag gac ttc aag tcc     384
Asn Asp Glu Ile Arg His His Thr Leu Leu Asp Glu Asp Phe Lys Ser
```

```
                115                 120                 125
cag ttc aac gtg ttc cca cgc gac gct cac cca atg gca acc ttg gct         432
Gln Phe Asn Val Phe Pro Arg Asp Ala His Pro Met Ala Thr Leu Ala
    130                 135                 140 tcc tcg gtt aac att ttg tct acc tac tac cag gac cag ctg aac cca         480
Ser Ser Val Asn Ile Leu Ser Thr Tyr Tyr Gln Asp Gln Leu Asn Pro
145                 150                 155                 160 ctc gat gag gca cag ctt gat aag gca acc gtt cgc ctc atg gca aag         528
Leu Asp Glu Ala Gln Leu Asp Lys Ala Thr Val Arg Leu Met Ala Lys
                165                 170                 175 gtt cca atg ctg gct gcg tac gca cac cgc gca cgc aag ggt gct cct         576
Val Pro Met Leu Ala Ala Tyr Ala His Arg Ala Arg Lys Gly Ala Pro
            180                 185                 190 tac atg tac cca gac aac tcc ctc aat gcg cgt gag aac ttc ctg cgc         624
Tyr Met Tyr Pro Asp Asn Ser Leu Asn Ala Arg Glu Asn Phe Leu Arg
        195                 200                 205 atg atg ttc ggt tac cca acc gag cca tac gag atc gac cca atc atg         672
Met Met Phe Gly Tyr Pro Thr Glu Pro Tyr Glu Ile Asp Pro Ile Met
    210                 215                 220 gtc aag gct ctg gac aag ctc ctc atc ctg cac gct gac cac gag cag         720
Val Lys Ala Leu Asp Lys Leu Leu Ile Leu His Ala Asp His Glu Gln
225                 230                 235                 240 aac tgc tcc acc tcc acc gtt cgt atg atc ggt tcc gca cag gcc aac         768
Asn Cys Ser Thr Ser Thr Val Arg Met Ile Gly Ser Ala Gln Ala Asn
                245                 250                 255 atg ttt gtc tcc atc gct ggt ggc atc aac gct ctg tcc ggc cca ctg         816
Met Phe Val Ser Ile Ala Gly Gly Ile Asn Ala Leu Ser Gly Pro Leu
            260                 265                 270 cac ggt ggc gca aac cag gct gtt ctg gag atg ctc gaa gac atc aag         864
His Gly Gly Ala Asn Gln Ala Val Leu Glu Met Leu Glu Asp Ile Lys
        275                 280                 285 agc aac cac ggt ggc gac gca acc gag ttc atg aac aag gtc aag aac         912
Ser Asn His Gly Gly Asp Ala Thr Glu Phe Met Asn Lys Val Lys Asn
    290                 295                 300 aag gaa gac ggc gtc cgc ctc atg ggc ttc gga cac cgc gtt tac aag         960
Lys Glu Asp Gly Val Arg Leu Met Gly Phe Gly His Arg Val Tyr Lys
305                 310                 315                 320 aac tac gat cca cgt gca gca atc gtc aag gag acc gca cac gag atc        1008
Asn Tyr Asp Pro Arg Ala Ala Ile Val Lys Glu Thr Ala His Glu Ile
                325                 330                 335 ctc gag cac ctc ggt ggc gac gat ctt ctg gat ctg gca atc aag ctg        1056
Leu Glu His Leu Gly Gly Asp Asp Leu Leu Asp Leu Ala Ile Lys Leu
            340                 345                 350 gaa gaa att gca ctg gct gat gat tac ttc atc tcc cgc aag ctc tac        1104
Glu Glu Ile Ala Leu Ala Asp Asp Tyr Phe Ile Ser Arg Lys Leu Tyr
        355                 360                 365 ccg aac gta gac ttc tac acc ggc ctg atc tac cgc gca atg ggc ttc        1152
Pro Asn Val Asp Phe Tyr Thr Gly Leu Ile Tyr Arg Ala Met Gly Phe
    370                 375                 380 cca act gac ttc ttc acc gta ttg ttc gca atc ggt cgt ctg cca gga        1200
Pro Thr Asp Phe Phe Thr Val Leu Phe Ala Ile Gly Arg Leu Pro Gly
385                 390                 395                 400 tgg atc gct cac tac cgc gag cag ctc ggt gca gca ggc aac aag atc        1248
Trp Ile Ala His Tyr Arg Glu Gln Leu Gly Ala Ala Gly Asn Lys Ile
                405                 410                 415 aac cgc cca cgc cag gtc tac acc ggc aac gaa tcc cgc aag ttg gtt        1296
Asn Arg Pro Arg Gln Val Tyr Thr Gly Asn Glu Ser Arg Lys Leu Val
            420                 425                 430 cct cgc gag gag cgc taa                                                1314
```

Pro Arg Glu Glu Arg
        435

<210> SEQ ID NO 2
<211> LENGTH: 437
<212> TYPE: PRT
<213> ORGANISM: Corynebacterium glutamicum

<400> SEQUENCE: 2

Met Phe Glu Arg Asp Ile Val Ala Thr Asp Asn Asn Lys Ala Val Leu
1               5                   10                  15

His Tyr Pro Gly Gly Glu Phe Glu Met Asp Ile Ile Glu Ala Ser Glu
            20                  25                  30

Gly Asn Asn Gly Val Val Leu Gly Lys Met Leu Ser Glu Thr Gly Leu
        35                  40                  45

Ile Thr Phe Asp Pro Gly Tyr Val Ser Thr Gly Ser Thr Glu Ser Lys
    50                  55                  60

Ile Thr Tyr Ile Asp Gly Asp Ala Gly Ile Leu Arg Tyr Arg Gly Tyr
65                  70                  75                  80

Asp Ile Ala Asp Leu Ala Glu Asn Ala Thr Phe Asn Glu Val Ser Tyr
                85                  90                  95

Leu Leu Ile Asn Gly Glu Leu Pro Thr Pro Asp Glu Leu His Lys Phe
            100                 105                 110

Asn Asp Glu Ile Arg His His Thr Leu Leu Asp Glu Asp Phe Lys Ser
        115                 120                 125

Gln Phe Asn Val Phe Pro Arg Asp Ala His Pro Met Ala Thr Leu Ala
    130                 135                 140

Ser Ser Val Asn Ile Leu Ser Thr Tyr Tyr Gln Asp Gln Leu Asn Pro
145                 150                 155                 160

Leu Asp Glu Ala Gln Leu Asp Lys Ala Thr Val Arg Leu Met Ala Lys
                165                 170                 175

Val Pro Met Leu Ala Ala Tyr Ala His Arg Ala Arg Lys Gly Ala Pro
            180                 185                 190

Tyr Met Tyr Pro Asp Asn Ser Leu Asn Ala Arg Glu Asn Phe Leu Arg
        195                 200                 205

Met Met Phe Gly Tyr Pro Thr Glu Pro Tyr Glu Ile Asp Pro Ile Met
    210                 215                 220

Val Lys Ala Leu Asp Lys Leu Leu Ile Leu His Ala Asp His Glu Gln
225                 230                 235                 240

Asn Cys Ser Thr Ser Thr Val Arg Met Ile Gly Ser Ala Gln Ala Asn
                245                 250                 255

Met Phe Val Ser Ile Ala Gly Gly Ile Asn Ala Leu Ser Gly Pro Leu
            260                 265                 270

His Gly Gly Ala Asn Gln Ala Val Leu Glu Met Leu Glu Asp Ile Lys
        275                 280                 285

Ser Asn His Gly Gly Asp Ala Thr Glu Phe Met Asn Lys Val Lys Asn
    290                 295                 300

Lys Glu Asp Gly Val Arg Leu Met Gly Phe Gly His Arg Val Tyr Lys
305                 310                 315                 320

Asn Tyr Asp Pro Arg Ala Ala Ile Val Lys Glu Thr Ala His Glu Ile
                325                 330                 335

Leu Glu His Leu Gly Gly Asp Asp Leu Leu Asp Leu Ala Ile Lys Leu
            340                 345                 350

Glu Glu Ile Ala Leu Ala Asp Asp Tyr Phe Ile Ser Arg Lys Leu Tyr
        355                 360                 365

```
Pro Asn Val Asp Phe Tyr Thr Gly Leu Ile Tyr Arg Ala Met Gly Phe
    370                 375                 380

Pro Thr Asp Phe Phe Thr Val Leu Phe Ala Ile Gly Arg Leu Pro Gly
385                 390                 395                 400

Trp Ile Ala His Tyr Arg Glu Gln Leu Gly Ala Ala Gly Asn Lys Ile
                405                 410                 415

Asn Arg Pro Arg Gln Val Tyr Thr Gly Asn Glu Ser Arg Lys Leu Val
            420                 425                 430

Pro Arg Glu Glu Arg
        435

<210> SEQ ID NO 3
<211> LENGTH: 2814
<212> TYPE: DNA
<213> ORGANISM: Corynebacterium glutamicum
<220> FEATURE:
<221> NAME/KEY: misc_feature
<222> LOCATION: (1)..(750)
<223> OTHER INFORMATION: sequence upatream of the coding region
<220> FEATURE:
<221> NAME/KEY: CDS
<222> LOCATION: (751)..(2061)
<223> OTHER INFORMATION: gltA-Wild-Type-Gene
<220> FEATURE:
<221> NAME/KEY: misc_feature
<222> LOCATION: (763)..(765)
<220> FEATURE:
<221> NAME/KEY: misc_feature
<222> LOCATION: (2062)..(2814)
<223> OTHER INFORMATION: sequence downstream of the coding region

<400> SEQUENCE: 3
```

| | | |
|---|---|---|
| agggcagggt ggggaagtcg gtcatgtctt cgggcaactt tctgcgcttg gaagtaaaag | 60 |
| ggccagggat cgttaacgat ctgacccaac aactataacc ctgaagctgt cagttcctag | 120 |
| caccctagat tcttcacgca gtctcccaaa cgatgaaaaa cgcccaaaac tggcgacacc | 180 |
| gaactattga aaacgcgggg attagttgac cagccaccaa tttgggggta gctcaaagtt | 240 |
| ttgcaaagtt ttcaatttct aggttgttaa tatcccctga ggttgcgtta tagggtggcg | 300 |
| aattgcatgg ggaaagctac tcggcaccca tccttgtcgc gtgcatcaca aactttgcta | 360 |
| aactgtgcac cagtccactt attgtgggat ttttaatgcc ttaaaggcca gcattttcac | 420 |
| cctctagcgg ggttgaatgc tggccttgag ggtgcagaac taaatagcag cacatcggca | 480 |
| caattgatct gagttctatt ggcgtgaccg tggctactga ttacggtggc tgtgggtggt | 540 |
| cgggaatgat gtaaccaacg tgattgtggg ggaattggct ctcacttcgg atatggctaa | 600 |
| accgcattta tcggtatagc gtgttaaccg gaccagattg ggaaagaaat gtgtcgagta | 660 |
| acaaaaactg acatgcgctt ggcgcatccc agttggtaag aataaacggg actacttccg | 720 |
| taatccggaa gagtttttttt ccgaacaaat atg ttt gaa agg gat atc gtg gct | 774 |
|                                                Met Phe Glu Arg Asp Ile Val Ala<br>                                                 1              5 | |
| act gat aac aac aag gct gtc ctg cac tac ccc ggt ggc gag ttc gaa<br>Thr Asp Asn Asn Lys Ala Val Leu His Tyr Pro Gly Gly Glu Phe Glu<br>   10                   15                  20 | 822 |
| atg gac atc atc gag gct tct gag ggt aac aac ggt gtt gtc ctg ggc<br>Met Asp Ile Ile Glu Ala Ser Glu Gly Asn Asn Gly Val Val Leu Gly<br>25                   30                  35                  40 | 870 |
| aag atg ctg tct gag act gga ctg atc act ttt gac cca ggt tat gtg<br>Lys Met Leu Ser Glu Thr Gly Leu Ile Thr Phe Asp Pro Gly Tyr Val<br>             45                  50                  55 | 918 |

```
agc act ggc tcc acc gag tcg aag atc acc tac atc gat ggc gat gcg      966
Ser Thr Gly Ser Thr Glu Ser Lys Ile Thr Tyr Ile Asp Gly Asp Ala
        60                  65                  70 gga atc ctg cgt tac cgc ggc tat gac atc gct gat ctg gct gag aat     1014
Gly Ile Leu Arg Tyr Arg Gly Tyr Asp Ile Ala Asp Leu Ala Glu Asn
    75                  80                  85 gcc acc ttc aac gag gtt tct tac cta ctt atc aac ggt gag cta cca     1062
Ala Thr Phe Asn Glu Val Ser Tyr Leu Leu Ile Asn Gly Glu Leu Pro
90                  95                  100 acc cca gat gag ctt cac aag ttt aac gac gag att cgc cac cac acc     1110
Thr Pro Asp Glu Leu His Lys Phe Asn Asp Glu Ile Arg His His Thr
105                 110                 115                 120 ctt ctg gac gag gac ttc aag tcc cag ttc aac gtg ttc cca cgc gac     1158
Leu Leu Asp Glu Asp Phe Lys Ser Gln Phe Asn Val Phe Pro Arg Asp
                125                 130                 135 gct cac cca atg gca acc ttg gct tcc tcg gtt aac att ttg tct acc     1206
Ala His Pro Met Ala Thr Leu Ala Ser Ser Val Asn Ile Leu Ser Thr
            140                 145                 150 tac tac cag gac cag ctg aac cca ctc gat gag gca cag ctt gat aag     1254
Tyr Tyr Gln Asp Gln Leu Asn Pro Leu Asp Glu Ala Gln Leu Asp Lys
        155                 160                 165 gca acc gtt cgc ctc atg gca aag gtt cca atg ctg gct gcg tac gca     1302
Ala Thr Val Arg Leu Met Ala Lys Val Pro Met Leu Ala Ala Tyr Ala
    170                 175                 180 cac cgc gca cgc aag ggt gct cct tac atg tac cca gac aac tcc ctc     1350
His Arg Ala Arg Lys Gly Ala Pro Tyr Met Tyr Pro Asp Asn Ser Leu
185                 190                 195                 200 aat gcg cgt gag aac ttc ctg cgc atg atg ttc ggt tac cca acc gag     1398
Asn Ala Arg Glu Asn Phe Leu Arg Met Met Phe Gly Tyr Pro Thr Glu
                205                 210                 215 cca tac gag atc gac cca atc atg gtc aag gct ctg gac aag ctg ctc     1446
Pro Tyr Glu Ile Asp Pro Ile Met Val Lys Ala Leu Asp Lys Leu Leu
            220                 225                 230 atc ctg cac gct gac cac gag cag aac tgc tcc acc tcc acc gtt cgt     1494
Ile Leu His Ala Asp His Glu Gln Asn Cys Ser Thr Ser Thr Val Arg
        235                 240                 245 atg atc ggt tcc gca cag gcc aac atg ttt gtc tcc atc gct ggt ggc     1542
Met Ile Gly Ser Ala Gln Ala Asn Met Phe Val Ser Ile Ala Gly Gly
    250                 255                 260 atc aac gct ctg tcc ggc cca ctg cac ggt ggc gca aac cag gct gtt     1590
Ile Asn Ala Leu Ser Gly Pro Leu His Gly Gly Ala Asn Gln Ala Val
265                 270                 275                 280 ctg gag atg ctc gaa gac atc aag agc aac cac ggt ggc gac gca acc     1638
Leu Glu Met Leu Glu Asp Ile Lys Ser Asn His Gly Gly Asp Ala Thr
                285                 290                 295 gag ttc atg aac aag gtc aag aac aag gaa gac ggc gtc cgc ctc atg     1686
Glu Phe Met Asn Lys Val Lys Asn Lys Glu Asp Gly Val Arg Leu Met
            300                 305                 310 ggc ttc gga cac cgc gtt tac aag aac tac gat cca cgt gca gca atc     1734
Gly Phe Gly His Arg Val Tyr Lys Asn Tyr Asp Pro Arg Ala Ala Ile
        315                 320                 325 gtc aag gag acc gca cac gag atc ctc gag cac ctc ggt ggc gac gat     1782
Val Lys Glu Thr Ala His Glu Ile Leu Glu His Leu Gly Gly Asp Asp
    330                 335                 340 ctt ctg gat ctg gca atc aag ctg gaa gaa att gca ctg gct gat gat     1830
Leu Leu Asp Leu Ala Ile Lys Leu Glu Glu Ile Ala Leu Ala Asp Asp
345                 350                 355                 360 tac ttc atc tcc cgc aag ctc tac ccg aac gta gac ttc tac acc ggc     1878
Tyr Phe Ile Ser Arg Lys Leu Tyr Pro Asn Val Asp Phe Tyr Thr Gly
                365                 370                 375
```

-continued

```
ctg atc tac cgc gca atg ggc ttc cca act gac ttc ttc acc gta ttg      1926
Leu Ile Tyr Arg Ala Met Gly Phe Pro Thr Asp Phe Phe Thr Val Leu
        380                 385                 390 ttc gca atc ggt cgt ctg cca gga tgg atc gct cac tac cgc gag cag      1974
Phe Ala Ile Gly Arg Leu Pro Gly Trp Ile Ala His Tyr Arg Glu Gln
    395                 400                 405 ctc ggt gca gca ggc aac aag atc aac cgc cca cgc cag gtc tac acc      2022
Leu Gly Ala Ala Gly Asn Lys Ile Asn Arg Pro Arg Gln Val Tyr Thr
410                 415                 420 ggc aac gaa tcc cgc aag ttg gtt cct cgc gag gag cgc taaatttagc       2071
Gly Asn Glu Ser Arg Lys Leu Val Pro Arg Glu Glu Arg
425                 430                 435 ggatgattct cgttcaactt cggccgaagc cacttcgtct gtcataatga cagggatggt    2131
ttcggccgtt tttgcatgaa accaaaaaat acgattttca aggagcatgt acagcacatg    2191
gaaaagccac agattgagct accggtcggt ccagcaccgg aagatctcgt aatctctgac    2251
atcatcgttg gcgaaggagc agaagcccgc ccaggtggag aagttgaggt ccactatgtg    2311
ggcgttgact ttgaaaccgg cgaggagttt gactcttcct gggatcgtgg acagaccagc    2371
cagttcccac tcaacggcct cattgcaggt tggcaagagg gaattccagg catgaaggtc    2431
ggcggacgtc gtcagctgac cattccgcca gaggctgctt acggccctga gggttccggc    2491
cacccactgt ctggccgtac cctggtgttc atcatcgatt tgatcagcgc ataatttct     2551
ttactgcgct aaacgctcaa atcgtgtgaa gcgactgtcg cgtcccgccc tctccggatt    2611
gttatccaat tcggagaggg cgttgctgat tgtgccgaga atttcttcaa caaagtgctc    2671
ggtttcggcg acgatcccgt cgataagccc ttggcttaaa agtgcgtgcg cctgcacgcc    2731
ttgtcgctct atgatttccg cggcgtggtt ggtgtcgcgg aagaggatgg ccgaggcgcc    2791
ctctggtggc aatgcggaca gcc                                            2814
```

<210> SEQ ID NO 4
<211> LENGTH: 437
<212> TYPE: PRT
<213> ORGANISM: Corynebacterium glutamicum

<400> SEQUENCE: 4

```
Met Phe Glu Arg Asp Ile Val Ala Thr Asp Asn Asn Lys Ala Val Leu
1               5                   10                  15

His Tyr Pro Gly Gly Glu Phe Glu Met Asp Ile Glu Ala Ser Glu
            20                  25                  30

Gly Asn Asn Gly Val Val Leu Gly Lys Met Leu Ser Glu Thr Gly Leu
        35                  40                  45

Ile Thr Phe Asp Pro Gly Tyr Val Ser Thr Gly Ser Thr Glu Ser Lys
    50                  55                  60

Ile Thr Tyr Ile Asp Gly Asp Ala Gly Ile Leu Arg Tyr Arg Gly Tyr
65                  70                  75                  80

Asp Ile Ala Asp Leu Ala Glu Asn Ala Thr Phe Asn Glu Val Ser Tyr
                85                  90                  95

Leu Leu Ile Asn Gly Glu Leu Pro Thr Pro Asp Glu Leu His Lys Phe
            100                 105                 110

Asn Asp Glu Ile Arg His His Thr Leu Leu Asp Glu Asp Phe Lys Ser
        115                 120                 125

Gln Phe Asn Val Phe Pro Arg Asp Ala His Pro Met Ala Thr Leu Ala
    130                 135                 140

Ser Ser Val Asn Ile Leu Ser Thr Tyr Tyr Gln Asp Gln Leu Asn Pro
```

-continued

```
                145                 150                 155                 160
Leu Asp Glu Ala Gln Leu Asp Lys Ala Thr Val Arg Leu Met Ala Lys
            165                 170                 175
Val Pro Met Leu Ala Ala Tyr Ala His Arg Ala Arg Lys Gly Ala Pro
        180                 185                 190
Tyr Met Tyr Pro Asp Asn Ser Leu Asn Ala Arg Glu Asn Phe Leu Arg
            195                 200                 205
Met Met Phe Gly Tyr Pro Thr Glu Pro Tyr Glu Ile Asp Pro Ile Met
        210                 215                 220
Val Lys Ala Leu Asp Lys Leu Ile Leu His Ala Asp His Glu Gln
225                 230                 235                 240
Asn Cys Ser Thr Ser Thr Val Arg Met Ile Gly Ser Ala Gln Ala Asn
                245                 250                 255
Met Phe Val Ser Ile Ala Gly Gly Ile Asn Ala Leu Ser Gly Pro Leu
            260                 265                 270
His Gly Gly Ala Asn Gln Ala Val Leu Glu Met Leu Glu Asp Ile Lys
        275                 280                 285
Ser Asn His Gly Gly Asp Ala Thr Glu Phe Met Asn Lys Val Lys Asn
290                 295                 300
Lys Glu Asp Gly Val Arg Leu Met Gly Phe Gly His Arg Val Tyr Lys
305                 310                 315                 320
Asn Tyr Asp Pro Arg Ala Ala Ile Val Lys Glu Thr Ala His Glu Ile
                325                 330                 335
Leu Glu His Leu Gly Gly Asp Asp Leu Leu Asp Leu Ala Ile Lys Leu
            340                 345                 350
Glu Glu Ile Ala Leu Ala Asp Asp Tyr Phe Ile Ser Arg Lys Leu Tyr
        355                 360                 365
Pro Asn Val Asp Phe Tyr Thr Gly Leu Ile Tyr Arg Ala Met Gly Phe
    370                 375                 380
Pro Thr Asp Phe Phe Thr Val Leu Phe Ala Ile Gly Arg Leu Pro Gly
385                 390                 395                 400
Trp Ile Ala His Tyr Arg Glu Gln Leu Gly Ala Ala Gly Asn Lys Ile
                405                 410                 415
Asn Arg Pro Arg Gln Val Tyr Thr Gly Asn Glu Ser Arg Lys Leu Val
            420                 425                 430
Pro Arg Glu Glu Arg
        435

<210> SEQ ID NO 5
<211> LENGTH: 1314
<212> TYPE: DNA
<213> ORGANISM: Corynebacterium glutamicum
<220> FEATURE:
<221> NAME/KEY: CDS
<222> LOCATION: (1)..(1311)
<223> OTHER INFORMATION: gltA-Allele
<220> FEATURE:
<221> NAME/KEY: misc_feature
<222> LOCATION: (13)..(15)
<220> FEATURE:
<221> NAME/KEY: mutation
<222> LOCATION: (14)..(14)
<223> OTHER INFORMATION: Transversion A > T

<400> SEQUENCE: 5 atg ttt gaa agg gtt atc gtg gct act gat aac aac aag gct gtc ctg      48
Met Phe Glu Arg Val Ile Val Ala Thr Asp Asn Asn Lys Ala Val Leu
1               5                   10                  15
```

```
cac tac ccc ggt ggc gag ttc gaa atg gac atc atc gag gct tct gag        96
His Tyr Pro Gly Gly Glu Phe Glu Met Asp Ile Ile Glu Ala Ser Glu
             20                  25                  30 ggt aac aac ggt gtt gtc ctg ggc aag atg ctg tct gag act gga ctg       144
Gly Asn Asn Gly Val Val Leu Gly Lys Met Leu Ser Glu Thr Gly Leu
         35                  40                  45 atc act ttt gac cca ggt tat gtg agc act ggc tcc acc gag tcg aag       192
Ile Thr Phe Asp Pro Gly Tyr Val Ser Thr Gly Ser Thr Glu Ser Lys
 50                  55                  60 atc acc tac atc gat ggc gat gcg gga atc ctg cgt tac cgc ggc tat       240
Ile Thr Tyr Ile Asp Gly Asp Ala Gly Ile Leu Arg Tyr Arg Gly Tyr
 65                  70                  75                  80 gac atc gct gat ctg gct gag aat gcc acc ttc aac gag gtt tct tac       288
Asp Ile Ala Asp Leu Ala Glu Asn Ala Thr Phe Asn Glu Val Ser Tyr
                 85                  90                  95 cta ctt atc aac ggt gag cta cca acc cca gat gag ctt cac aag ttt       336
Leu Leu Ile Asn Gly Glu Leu Pro Thr Pro Asp Glu Leu His Lys Phe
            100                 105                 110 aac gac gag att cgc cac cac acc ctt ctg gac gag gac ttc aag tcc       384
Asn Asp Glu Ile Arg His His Thr Leu Leu Asp Glu Asp Phe Lys Ser
        115                 120                 125 cag ttc aac gtg ttc cca cgc gac gct cac cca atg gca acc ttg gct       432
Gln Phe Asn Val Phe Pro Arg Asp Ala His Pro Met Ala Thr Leu Ala
130                 135                 140 tcc tcg gtt aac att ttg tct acc tac tac cag gac cag ctg aac cca       480
Ser Ser Val Asn Ile Leu Ser Thr Tyr Tyr Gln Asp Gln Leu Asn Pro
145                 150                 155                 160 ctc gat gag gca cag ctt gat aag gca acc gtt cgc ctc atg gca aag       528
Leu Asp Glu Ala Gln Leu Asp Lys Ala Thr Val Arg Leu Met Ala Lys
                165                 170                 175 gtt cca atg ctg gct gcg tac gca cac cgc gca cgc aag ggt gct cct       576
Val Pro Met Leu Ala Ala Tyr Ala His Arg Ala Arg Lys Gly Ala Pro
            180                 185                 190 tac atg tac cca gac aac tcc ctc aat gcg cgt gag aac ttc ctg cgc       624
Tyr Met Tyr Pro Asp Asn Ser Leu Asn Ala Arg Glu Asn Phe Leu Arg
        195                 200                 205 atg atg ttc ggt tac cca acc gag cca tac gag atc gac cca atc atg       672
Met Met Phe Gly Tyr Pro Thr Glu Pro Tyr Glu Ile Asp Pro Ile Met
    210                 215                 220 gtc aag gct ctg gac aag ctg ctc atc ctg cac gct gac cac gag cag       720
Val Lys Ala Leu Asp Lys Leu Leu Ile Leu His Ala Asp His Glu Gln
225                 230                 235                 240 aac tgc tcc acc tcc acc gtt cgt atg atc ggt tcc gca cag gcc aac       768
Asn Cys Ser Thr Ser Thr Val Arg Met Ile Gly Ser Ala Gln Ala Asn
                245                 250                 255 atg ttt gtc tcc atc gct ggt ggc atc aac gct ctg tcc ggc cca ctg       816
Met Phe Val Ser Ile Ala Gly Gly Ile Asn Ala Leu Ser Gly Pro Leu
            260                 265                 270 cac ggt ggc gca aac cag gct gtt ctg gag atg ctc gaa gac atc aag       864
His Gly Gly Ala Asn Gln Ala Val Leu Glu Met Leu Glu Asp Ile Lys
        275                 280                 285 agc aac cac ggt ggc gac gca acc gag ttc atg aac aag gtc aag aac       912
Ser Asn His Gly Gly Asp Ala Thr Glu Phe Met Asn Lys Val Lys Asn
    290                 295                 300 aag gaa gac ggc gtc cgc ctc atg ggc ttc gga cac cgc gtt tac aag       960
Lys Glu Asp Gly Val Arg Leu Met Gly Phe Gly His Arg Val Tyr Lys
305                 310                 315                 320 aac tac gat cca cgt gca gca atc gtc aag gag acc gca cac gag atc      1008
Asn Tyr Asp Pro Arg Ala Ala Ile Val Lys Glu Thr Ala His Glu Ile
                325                 330                 335
```

```
ctc gag cac ctc ggt ggc gac gat ctt ctg gat ctg gca atc aag ctg    1056
Leu Glu His Leu Gly Gly Asp Asp Leu Leu Asp Leu Ala Ile Lys Leu
        340                 345                 350 gaa gaa att gca ctg gct gat gat tac ttc atc tcc cgc aag ctc tac    1104
Glu Glu Ile Ala Leu Ala Asp Asp Tyr Phe Ile Ser Arg Lys Leu Tyr
            355                 360                 365 ccg aac gta gac ttc tac acc ggc ctg atc tac cgc gca atg ggc ttc    1152
Pro Asn Val Asp Phe Tyr Thr Gly Leu Ile Tyr Arg Ala Met Gly Phe
    370                 375                 380 cca act gac ttc ttc acc gta ttg ttc gca atc ggt cgt ctg cca gga    1200
Pro Thr Asp Phe Phe Thr Val Leu Phe Ala Ile Gly Arg Leu Pro Gly
385                 390                 395                 400 tgg atc gct cac tac cgc gag cag ctc ggt gca gca ggc aac aag atc    1248
Trp Ile Ala His Tyr Arg Glu Gln Leu Gly Ala Ala Gly Asn Lys Ile
            405                 410                 415 aac cgc cca cgc cag gtc tac acc ggc aac gaa tcc cgc aag ttg gtt    1296
Asn Arg Pro Arg Gln Val Tyr Thr Gly Asn Glu Ser Arg Lys Leu Val
        420                 425                 430 cct cgc gag gag cgc taa                                             1314
Pro Arg Glu Glu Arg
        435

<210> SEQ ID NO 6
<211> LENGTH: 437
<212> TYPE: PRT
<213> ORGANISM: Corynebacterium glutamicum

<400> SEQUENCE: 6

Met Phe Glu Arg Val Ile Val Ala Thr Asp Asn Asn Lys Ala Val Leu
1               5                   10                  15

His Tyr Pro Gly Gly Glu Phe Glu Met Asp Ile Ile Glu Ala Ser Glu
            20                  25                  30

Gly Asn Asn Gly Val Val Leu Gly Lys Met Leu Ser Glu Thr Gly Leu
        35                  40                  45

Ile Thr Phe Asp Pro Gly Tyr Val Ser Thr Gly Ser Thr Glu Ser Lys
    50                  55                  60

Ile Thr Tyr Ile Asp Gly Asp Ala Gly Ile Leu Arg Tyr Arg Gly Tyr
65                  70                  75                  80

Asp Ile Ala Asp Leu Ala Glu Asn Ala Thr Phe Asn Glu Val Ser Tyr
                85                  90                  95

Leu Leu Ile Asn Gly Glu Leu Pro Thr Pro Asp Glu Leu His Lys Phe
            100                 105                 110

Asn Asp Glu Ile Arg His His Thr Leu Leu Asp Glu Asp Phe Lys Ser
        115                 120                 125

Gln Phe Asn Val Phe Pro Arg Asp Ala His Pro Met Ala Thr Leu Ala
    130                 135                 140

Ser Ser Val Asn Ile Leu Ser Thr Tyr Tyr Gln Asp Gln Leu Asn Pro
145                 150                 155                 160

Leu Asp Glu Ala Gln Leu Asp Lys Ala Thr Val Arg Leu Met Ala Lys
                165                 170                 175

Val Pro Met Leu Ala Ala Tyr Ala His Arg Ala Arg Lys Gly Ala Pro
            180                 185                 190

Tyr Met Tyr Pro Asp Asn Ser Leu Asn Ala Arg Glu Asn Phe Leu Arg
        195                 200                 205

Met Met Phe Gly Tyr Pro Thr Glu Pro Tyr Glu Ile Asp Pro Ile Met
    210                 215                 220
```

Val Lys Ala Leu Asp Lys Leu Leu Ile Leu His Ala Asp His Glu Gln
225                 230                 235                 240

Asn Cys Ser Thr Ser Thr Val Arg Met Ile Gly Ser Ala Gln Ala Asn
                245                 250                 255

Met Phe Val Ser Ile Ala Gly Gly Ile Asn Ala Leu Ser Gly Pro Leu
            260                 265                 270

His Gly Gly Ala Asn Gln Ala Val Leu Glu Met Leu Glu Asp Ile Lys
        275                 280                 285

Ser Asn His Gly Gly Asp Ala Thr Glu Phe Met Asn Lys Val Lys Asn
    290                 295                 300

Lys Glu Asp Gly Val Arg Leu Met Gly Phe Gly His Arg Val Tyr Lys
305                 310                 315                 320

Asn Tyr Asp Pro Arg Ala Ala Ile Val Lys Glu Thr Ala His Glu Ile
                325                 330                 335

Leu Glu His Leu Gly Gly Asp Asp Leu Leu Asp Leu Ala Ile Lys Leu
            340                 345                 350

Glu Glu Ile Ala Leu Ala Asp Asp Tyr Phe Ile Ser Arg Lys Leu Tyr
        355                 360                 365

Pro Asn Val Asp Phe Tyr Thr Gly Leu Ile Tyr Arg Ala Met Gly Phe
    370                 375                 380

Pro Thr Asp Phe Phe Thr Val Leu Phe Ala Ile Gly Arg Leu Pro Gly
385                 390                 395                 400

Trp Ile Ala His Tyr Arg Glu Gln Leu Gly Ala Ala Gly Asn Lys Ile
                405                 410                 415

Asn Arg Pro Arg Gln Val Tyr Thr Gly Asn Glu Ser Arg Lys Leu Val
            420                 425                 430

Pro Arg Glu Glu Arg
        435

<210> SEQ ID NO 7
<211> LENGTH: 2814
<212> TYPE: DNA
<213> ORGANISM: Corynebacterium glutamicum
<220> FEATURE:
<221> NAME/KEY: misc_feature
<222> LOCATION: (1)..(750)
<223> OTHER INFORMATION: sequence upstream of the coding region
<220> FEATURE:
<221> NAME/KEY: CDS
<222> LOCATION: (751)..(2061)
<223> OTHER INFORMATION: gltA-Allele
<220> FEATURE:
<221> NAME/KEY: misc_feature
<222> LOCATION: (763)..(765)
<220> FEATURE:
<221> NAME/KEY: mutation
<222> LOCATION: (764)..(764)
<223> OTHER INFORMATION: Transversion A > T
<220> FEATURE:
<221> NAME/KEY: misc_feature
<222> LOCATION: (2062)..(2814)
<223> OTHER INFORMATION: sequence downstream of the coding region

<400> SEQUENCE: 7
agggcagggt ggggaagtcg gtcatgtctt cgggcaactt tctgcgcttg gaagtaaaag      60
ggccagggat cgttaacgat ctgacccaac aactataacc ctgaagctgt cagttcctag     120
caccctagat tcttcacgca gtctcccaaa cgatgaaaaa cgcccaaaac tggcgacacc     180
gaactattga aaacgcgggg attagttgac cagccaccaa tttgggggta gctcaaagtt     240
ttgcaaagtt ttcaatttct aggttgttaa tatccccctga ggttgcgtta tagggtggcg     300

-continued

```
aattgcatgg ggaaagctac tcggcaccca tccttgtcgc gtgcatcaca aactttgcta    360
aactgtgcac cagtccactt attgtgggat ttttaatgcc ttaaaggcca gcattttcac    420
cctctagcgg ggttgaatgc tggccttgag ggtgcagaac taaatagcag cacatcggca    480
caattgatct gagttctatt ggcgtgaccg tggctactga ttacggtggc tgtgggtggt    540
cgggaatgat gtaaccaacg tgattgtggg ggaattggct ctcacttcgg atatggctaa    600
accgcattta tcgtatagc gtgttaaccg gaccagattg ggaaagaaat gtgtcgagta    660
acaaaaactg acatgcgctt ggcgcatccc agttggtaag aataaacggg actacttccg    720
taatccggaa gagttttttt ccgaacaaat atg ttt gaa agg gtt atc gtg gct    774
                                   Met Phe Glu Arg Val Ile Val Ala
                                     1               5 act gat aac aac aag gct gtc ctg cac tac ccc ggt ggc gag ttc gaa    822
Thr Asp Asn Asn Lys Ala Val Leu His Tyr Pro Gly Gly Glu Phe Glu
 10              15                  20 atg gac atc atc gag gct tct gag ggt aac aac ggt gtt gtc ctg ggc    870
Met Asp Ile Ile Glu Ala Ser Glu Gly Asn Asn Gly Val Val Leu Gly
25              30                  35                  40 aag atg ctg tct gag act gga ctg atc act ttt gac cca ggt tat gtg    918
Lys Met Leu Ser Glu Thr Gly Leu Ile Thr Phe Asp Pro Gly Tyr Val
                45                  50                  55 agc act ggc tcc acc gag tcg aag atc acc tac atc gat ggc gat gcg    966
Ser Thr Gly Ser Thr Glu Ser Lys Ile Thr Tyr Ile Asp Gly Asp Ala
            60                  65                  70 gga atc ctg cgt tac cgc ggc tat gac atc gct gat ctg gct gag aat    1014
Gly Ile Leu Arg Tyr Arg Gly Tyr Asp Ile Ala Asp Leu Ala Glu Asn
                75                  80                  85 gcc acc ttc aac gag gtt tct tac cta ctt atc aac ggt gag cta cca    1062
Ala Thr Phe Asn Glu Val Ser Tyr Leu Leu Ile Asn Gly Glu Leu Pro
 90                  95                  100 acc cca gat gag ctt cac aag ttt aac gac gag att cgc cac cac acc    1110
Thr Pro Asp Glu Leu His Lys Phe Asn Asp Glu Ile Arg His His Thr
105                 110                 115                 120 ctt ctg gac gag gac ttc aag tcc cag ttc aac gtg ttc cca cgc gac    1158
Leu Leu Asp Glu Asp Phe Lys Ser Gln Phe Asn Val Phe Pro Arg Asp
                125                 130                 135 gct cac cca atg gca acc ttg gct tcc tcg gtt aac att ttg tct acc    1206
Ala His Pro Met Ala Thr Leu Ala Ser Ser Val Asn Ile Leu Ser Thr
            140                 145                 150 tac tac cag gac cag ctg aac cca ctc gat gag gca cag ctt gat aag    1254
Tyr Tyr Gln Asp Gln Leu Asn Pro Leu Asp Glu Ala Gln Leu Asp Lys
                155                 160                 165 gca acc gtt cgc ctc atg gca aag gtt cca atg ctg gct gcg tac gca    1302
Ala Thr Val Arg Leu Met Ala Lys Val Pro Met Leu Ala Ala Tyr Ala
170                 175                 180 cac cgc gca cgc aag ggt gct cct tac atg tac cca gac aac tcc ctc    1350
His Arg Ala Arg Lys Gly Ala Pro Tyr Met Tyr Pro Asp Asn Ser Leu
185                 190                 195                 200 aat gcg cgt gag aac ttc ctg cgc atg atg ttc ggt tac cca acc gag    1398
Asn Ala Arg Glu Asn Phe Leu Arg Met Met Phe Gly Tyr Pro Thr Glu
                205                 210                 215 cca tac gag atc gac cca atc atg gtc aag gct ctg gac aag ctg ctc    1446
Pro Tyr Glu Ile Asp Pro Ile Met Val Lys Ala Leu Asp Lys Leu Leu
            220                 225                 230 atc ctg cac gct gac cac gag cag aac tgc tcc acc tcc acc gtt cgt    1494
Ile Leu His Ala Asp His Glu Gln Asn Cys Ser Thr Ser Thr Val Arg
                235                 240                 245 atg atc ggt tcc gca cag gcc aac atg ttt gtc tcc atc gct ggt ggc    1542
```

```
                Met Ile Gly Ser Ala Gln Ala Asn Met Phe Val Ser Ile Ala Gly Gly
                    250                 255                 260 atc aac gct ctg tcc ggc cca ctg cac ggt ggc gca aac cag gct gtt         1590
Ile Asn Ala Leu Ser Gly Pro Leu His Gly Gly Ala Asn Gln Ala Val
265                 270                 275                 280 ctg gag atg ctc gaa gac atc aag agc aac cac ggt ggc gac gca acc         1638
Leu Glu Met Leu Glu Asp Ile Lys Ser Asn His Gly Gly Asp Ala Thr
                285                 290                 295 gag ttc atg aac aag gtc aag aac aag gaa gac ggc gtc cgc ctc atg         1686
Glu Phe Met Asn Lys Val Lys Asn Lys Glu Asp Gly Val Arg Leu Met
            300                 305                 310 ggc ttc gga cac cgc gtt tac aag aac tac gat cca cgt gca gca atc         1734
Gly Phe Gly His Arg Val Tyr Lys Asn Tyr Asp Pro Arg Ala Ala Ile
        315                 320                 325 gtc aag gag acc gca cac gag atc ctc gag cac ctc ggt ggc gac gat         1782
Val Lys Glu Thr Ala His Glu Ile Leu Glu His Leu Gly Gly Asp Asp
    330                 335                 340 ctt ctg gat ctg gca atc aag ctg gaa gaa att gca ctg gct gat gat         1830
Leu Leu Asp Leu Ala Ile Lys Leu Glu Glu Ile Ala Leu Ala Asp Asp
345                 350                 355                 360 tac ttc atc tcc cgc aag ctc tac ccg aac gta gac ttc tac acc ggc         1878
Tyr Phe Ile Ser Arg Lys Leu Tyr Pro Asn Val Asp Phe Tyr Thr Gly
                365                 370                 375 ctg atc tac cgc gca atg ggc ttc cca act gac ttc ttc acc gta ttg         1926
Leu Ile Tyr Arg Ala Met Gly Phe Pro Thr Asp Phe Phe Thr Val Leu
            380                 385                 390 ttc gca atc ggt cgt ctg cca gga tgg atc gct cac tac cgc gag cag         1974
Phe Ala Ile Gly Arg Leu Pro Gly Trp Ile Ala His Tyr Arg Glu Gln
        395                 400                 405 ctc ggt gca gca ggc aac aag atc aac cgc cca cgc cag gtc tac acc         2022
Leu Gly Ala Ala Gly Asn Lys Ile Asn Arg Pro Arg Gln Val Tyr Thr
    410                 415                 420 ggc aac gaa tcc cgc aag ttg gtt cct cgc gag gag cgc taaatttagc         2071
Gly Asn Glu Ser Arg Lys Leu Val Pro Arg Glu Glu Arg
425                 430                 435 ggatgattct cgttcaactt cggccgaagc cacttcgtct gtcataatga cagggatggt      2131
ttcggccgtt tttgcatgaa accaaaaaat acgattttca aggagcatgt acagcacatg      2191
gaaaagccac agattgagct accggtcggt ccagcaccgg aagatctcgt aatctctgac      2251
atcatcgttg gcgaaggagc agaagcccgc ccaggtggag aagttgaggt ccactatgtg      2311
ggcgttgact ttgaaaccgg cgaggagttt gactcttcct gggatcgtgg acagaccagc      2371
cagttcccac tcaacggcct cattgcaggt tggcaagagg gaattccagg catgaaggtc      2431
ggcggacgtc gtcagctgac cattccgcca gaggctgctt acggccctga gggttccggc      2491
cacccactgt ctggccgtac cctggtgttc atcatcgatt tgatcagcgc ataattttct      2551
ttactgcgct aaacgctcaa atcgtgtgaa gcgactgtcg cgtcccgccc tctccggatt      2611
gttatccaat tcggagaggg cgttgctgat tgtgccgaga atttcttcaa caaagtgctc      2671
ggtttcggcg acgatcccgt cgataagccc ttggcttaaa agtgcgtgcg cctgcacgcc      2731
ttgtcgctct atgatttccg cggcgtggtt ggtgtcgcgg aagaggatgg ccgaggcgcc      2791
ctctggtggc aatgcggaca gcc                                              2814

<210> SEQ ID NO 8
<211> LENGTH: 437
<212> TYPE: PRT
<213> ORGANISM: Corynebacterium glutamicum
```

<400> SEQUENCE: 8

```
Met Phe Glu Arg Val Ile Val Ala Thr Asp Asn Asn Lys Ala Val Leu
1               5                   10                  15

His Tyr Pro Gly Gly Glu Phe Glu Met Asp Ile Ile Glu Ala Ser Glu
            20                  25                  30

Gly Asn Asn Gly Val Val Leu Gly Lys Met Leu Ser Glu Thr Gly Leu
            35                  40                  45

Ile Thr Phe Asp Pro Gly Tyr Val Ser Thr Gly Ser Thr Glu Ser Lys
50                  55                  60

Ile Thr Tyr Ile Asp Gly Asp Ala Gly Ile Leu Arg Tyr Arg Gly Tyr
65                  70                  75                  80

Asp Ile Ala Asp Leu Ala Glu Asn Ala Thr Phe Asn Glu Val Ser Tyr
                85                  90                  95

Leu Leu Ile Asn Gly Glu Leu Pro Thr Pro Asp Glu Leu His Lys Phe
            100                 105                 110

Asn Asp Glu Ile Arg His His Thr Leu Leu Asp Glu Asp Phe Lys Ser
            115                 120                 125

Gln Phe Asn Val Phe Pro Arg Asp Ala His Pro Met Ala Thr Leu Ala
130                 135                 140

Ser Ser Val Asn Ile Leu Ser Thr Tyr Tyr Gln Asp Gln Leu Asn Pro
145                 150                 155                 160

Leu Asp Glu Ala Gln Leu Asp Lys Ala Thr Val Arg Leu Met Ala Lys
                165                 170                 175

Val Pro Met Leu Ala Ala Tyr Ala His Arg Ala Arg Lys Gly Ala Pro
            180                 185                 190

Tyr Met Tyr Pro Asp Asn Ser Leu Asn Ala Arg Glu Asn Phe Leu Arg
            195                 200                 205

Met Met Phe Gly Tyr Pro Thr Glu Pro Tyr Glu Ile Asp Pro Ile Met
210                 215                 220

Val Lys Ala Leu Asp Lys Leu Leu Ile Leu His Ala Asp His Glu Gln
225                 230                 235                 240

Asn Cys Ser Thr Ser Thr Val Arg Met Ile Gly Ser Ala Gln Ala Asn
                245                 250                 255

Met Phe Val Ser Ile Ala Gly Ile Asn Ala Leu Ser Gly Pro Leu
            260                 265                 270

His Gly Gly Ala Asn Gln Ala Val Leu Glu Met Leu Glu Asp Ile Lys
            275                 280                 285

Ser Asn His Gly Gly Asp Ala Thr Glu Phe Met Asn Lys Val Lys Asn
290                 295                 300

Lys Glu Asp Gly Val Arg Leu Met Gly Phe Gly His Arg Val Tyr Lys
305                 310                 315                 320

Asn Tyr Asp Pro Arg Ala Ala Ile Val Lys Glu Thr Ala His Glu Ile
                325                 330                 335

Leu Glu His Leu Gly Gly Asp Asp Leu Leu Asp Leu Ala Ile Lys Leu
            340                 345                 350

Glu Glu Ile Ala Leu Ala Asp Asp Tyr Phe Ile Ser Arg Lys Leu Tyr
            355                 360                 365

Pro Asn Val Asp Phe Tyr Thr Gly Leu Ile Tyr Arg Ala Met Gly Phe
370                 375                 380

Pro Thr Asp Phe Phe Thr Val Leu Phe Ala Ile Gly Arg Leu Pro Gly
385                 390                 395                 400

Trp Ile Ala His Tyr Arg Glu Gln Leu Gly Ala Ala Gly Asn Lys Ile
                405                 410                 415
```

Asn Arg Pro Arg Gln Val Tyr Thr Gly Asn Glu Ser Arg Lys Leu Val
    420                 425                 430
Pro Arg Glu Glu Arg
        435

<210> SEQ ID NO 9
<211> LENGTH: 2814
<212> TYPE: DNA
<213> ORGANISM: Corynebacterium glutamicum
<220> FEATURE:
<221> NAME/KEY: misc_feature
<222> LOCATION: (1)..(750)
<223> OTHER INFORMATION: sequence upstream of the coding region
<220> FEATURE:
<221> NAME/KEY: CDS
<222> LOCATION: (751)..(2061)
<223> OTHER INFORMATION: gltA-Allele
<220> FEATURE:
<221> NAME/KEY: misc_feature
<222> LOCATION: (763)..(765)
<223> OTHER INFORMATION: n is a, c, g, or t
<220> FEATURE:
<221> NAME/KEY: misc_feature
<222> LOCATION: (2062)..(2814)
<223> OTHER INFORMATION: sequence downstream of the coding region

<400> SEQUENCE: 9

```
agggcagggt ggggaagtcg gtcatgtctt cgggcaactt tctgcgcttg gaagtaaaag    60
ggccagggat cgttaacgat ctgacccaac aactataacc ctgaagctgt cagttcctag   120
caccctagat tcttcacgca gtctcccaaa cgatgaaaaa cgcccaaaac tggcgacacc   180
gaactattga aaacgcgggg attagttgac cagccaccaa tttgggggta gctcaaagtt   240
ttgcaaagtt ttcaatttct aggttgttaa tatcccctga ggttgcgtta tagggtggcg   300
aattgcatgg ggaaagctac tcggcaccca tccttgtcgc gtgcatcaca aactttgcta   360
aactgtgcac cagtccactt attgtgggat ttttaatgcc ttaaaggcca gcattttcac   420
cctctagcgg ggttgaatgc tggccttgag ggtgcagaac taaatagcag cacatcggca   480
caattgatct gagttctatt ggcgtgaccg tggctactga ttcggtggc tgtgggtggt    540 cgggaatgat gtaaccaacg tgattgtggg ggaattggct ctcacttcgg atatggctaa   600
accgcattta tcggtatagc gtgttaaccg gaccagattg ggaaagaaat gtgtcgagta   660
acaaaaactg acatgcgctt ggcgcatccc agttggtaag aataaacggg actacttccg   720
taatccggaa gagttttttt ccgaacaaat atg ttt gaa agg nnn atc gtg gct    774
                                  Met Phe Glu Arg Xaa Ile Val Ala
                                   1               5
```

```
act gat aac aac aag gct gtc ctg cac tac ccc ggt ggc gag ttc gaa    822
Thr Asp Asn Asn Lys Ala Val Leu His Tyr Pro Gly Gly Glu Phe Glu
    10                  15                  20
```

```
atg gac atc atc gag gct tct gag ggt aac aac ggt gtt gtc ctg ggc    870
Met Asp Ile Ile Glu Ala Ser Glu Gly Asn Asn Gly Val Val Leu Gly
 25                  30                  35                  40
```

```
aag atg ctg tct gag act gga ctg atc act ttt gac cca ggt tat gtg    918
Lys Met Leu Ser Glu Thr Gly Leu Ile Thr Phe Asp Pro Gly Tyr Val
                     45                  50                  55
```

```
agc act ggc tcc acc gag tcg aag atc acc tac atc gat ggc gat gcg    966
Ser Thr Gly Ser Thr Glu Ser Lys Ile Thr Tyr Ile Asp Gly Asp Ala
             60                  65                  70
```

```
gga atc ctg cgt tac cgc ggc tat gac atc gct gat ctg gct gag aat   1014
Gly Ile Leu Arg Tyr Arg Gly Tyr Asp Ile Ala Asp Leu Ala Glu Asn
         75                  80                  85
```

```
gcc acc ttc aac gag gtt tct tac cta ctt atc aac ggt gag cta cca    1062
Ala Thr Phe Asn Glu Val Ser Tyr Leu Leu Ile Asn Gly Glu Leu Pro
    90              95                 100 acc cca gat gag ctt cac aag ttt aac gac gag att cgc cac cac acc    1110
Thr Pro Asp Glu Leu His Lys Phe Asn Asp Glu Ile Arg His His Thr
105             110                 115                 120 ctt ctg gac gag gac ttc aag tcc cag ttc aac gtg ttc cca cgc gac    1158
Leu Leu Asp Glu Asp Phe Lys Ser Gln Phe Asn Val Phe Pro Arg Asp
                125                 130                 135 gct cac cca atg gca acc ttg gct tcc tcg gtt aac att ttg tct acc    1206
Ala His Pro Met Ala Thr Leu Ala Ser Ser Val Asn Ile Leu Ser Thr
            140                 145                 150 tac tac cag gac cag ctg aac cca ctc gat gag gca cag ctt gat aag    1254
Tyr Tyr Gln Asp Gln Leu Asn Pro Leu Asp Glu Ala Gln Leu Asp Lys
                155                 160                 165 gca acc gtt cgc ctc atg gca aag gtt cca atg ctg gcg tac gca        1302
Ala Thr Val Arg Leu Met Ala Lys Val Pro Met Leu Ala Ala Tyr Ala
170                 175                 180 cac cgc gca cgc aag ggt gct cct tac atg tac cca gac aac tcc ctc    1350
His Arg Ala Arg Lys Gly Ala Pro Tyr Met Tyr Pro Asp Asn Ser Leu
185                 190                 195                 200 aat gcg cgt gag aac ttc ctg cgc atg atg ttc ggt tac cca acc gag    1398
Asn Ala Arg Glu Asn Phe Leu Arg Met Met Phe Gly Tyr Pro Thr Glu
                205                 210                 215 cca tac gag atc gac cca atc atg gtc aag gct ctg gac aag ctg ctc    1446
Pro Tyr Glu Ile Asp Pro Ile Met Val Lys Ala Leu Asp Lys Leu Leu
                220                 225                 230 atc ctg cac gct gac cac gag cag aac tgc tcc acc tcc acc gtt cgt    1494
Ile Leu His Ala Asp His Glu Gln Asn Cys Ser Thr Ser Thr Val Arg
            235                 240                 245 atg atc ggt tcc gca cag gcc aac atg ttt gtc tcc atc gct ggt ggc    1542
Met Ile Gly Ser Ala Gln Ala Asn Met Phe Val Ser Ile Ala Gly Gly
250                 255                 260 atc aac gct ctg tcc ggc cca ctg cac ggt ggc gca aac cag gct gtt    1590
Ile Asn Ala Leu Ser Gly Pro Leu His Gly Gly Ala Asn Gln Ala Val
265                 270                 275                 280 ctg gag atg ctc gaa gac atc aag agc aac cac ggt ggc gac gca acc    1638
Leu Glu Met Leu Glu Asp Ile Lys Ser Asn His Gly Gly Asp Ala Thr
                285                 290                 295 gag ttc atg aac aag gtc aag aac aag gaa gac ggc gtc cgc ctc atg    1686
Glu Phe Met Asn Lys Val Lys Asn Lys Glu Asp Gly Val Arg Leu Met
                300                 305                 310 ggc ttc gga cac cgc gtt tac aag aac tac gat cca cgt gca gca atc    1734
Gly Phe Gly His Arg Val Tyr Lys Asn Tyr Asp Pro Arg Ala Ala Ile
            315                 320                 325 gtc aag gag acc gca cac gag atc ctc gag cac ctc ggt ggc gac gat    1782
Val Lys Glu Thr Ala His Glu Ile Leu Glu His Leu Gly Gly Asp Asp
330                 335                 340 ctt ctg gat ctg gca atc aag ctg gaa gaa att gca ctg gct gat gat    1830
Leu Leu Asp Leu Ala Ile Lys Leu Glu Glu Ile Ala Leu Ala Asp Asp
345                 350                 355                 360 tac ttc atc tcc cgc aag ctc tac ccg aac gta gac ttc tac acc ggc    1878
Tyr Phe Ile Ser Arg Lys Leu Tyr Pro Asn Val Asp Phe Tyr Thr Gly
                365                 370                 375 ctg atc tac cgc gca atg ggc ttc cca act gac ttc ttc acc gta ttg    1926
Leu Ile Tyr Arg Ala Met Gly Phe Pro Thr Asp Phe Phe Thr Val Leu
            380                 385                 390 ttc gca atc ggt cgt ctg cca gga tgg atc gct cac tac cgc gag cag    1974
Phe Ala Ile Gly Arg Leu Pro Gly Trp Ile Ala His Tyr Arg Glu Gln
395                 400                 405
```

-continued

```
ctc ggt gca gca ggc aac aag atc aac cgc cca cgc cag gtc tac acc    2022
Leu Gly Ala Ala Gly Asn Lys Ile Asn Arg Pro Arg Gln Val Tyr Thr
    410                 415                 420 ggc aac gaa tcc cgc aag ttg gtt cct cgc gag gag cgc taaatttagc    2071
Gly Asn Glu Ser Arg Lys Leu Val Pro Arg Glu Glu Arg
425                 430                 435 ggatgattct cgttcaactt cggccgaagc cacttcgtct gtcataatga cagggatggt    2131
ttcggccgtt tttgcatgaa accaaaaaat acgattttca aggagcatgt acagcacatg    2191
gaaaagccac agattgagct accggtcggt ccagcaccgg aagatctcgt aatctctgac    2251
atcatcgttg gcgaaggagc agaagcccgc ccaggtggag aagttgaggt ccactatgtg    2311
ggcgttgact ttgaaaccgg cgaggagttt gactcttcct gggatcgtgg acagaccagc    2371
cagttcccac tcaacggcct cattgcaggt tggcaagagg gaattccagg catgaaggtc    2431
ggcggacgtc gtcagctgac cattccgcca gaggctgctt acggccctga gggttccggc    2491
cacccactgt ctggccgtac cctggtgttc atcatcgatt tgatcagcgc ataatttttct    2551 ttactgcgct aaacgctcaa atcgtgtgaa gcgactgtcg cgtcccgccc tctccggatt    2611
gttatccaat tcggagaggg cgttgctgat tgtgccgaga atttcttcaa caaagtgctc    2671
ggtttcggcg acgatcccgt cgataagccc ttggcttaaa agtgcgtgcg cctgcacgcc    2731
ttgtcgctct atgatttccg cggcgtggtt ggtgtcgcgg aagaggatgg ccgaggcgcc    2791
ctctggtggc aatgcggaca gcc    2814
```

<210> SEQ ID NO 10
<211> LENGTH: 437
<212> TYPE: PRT
<213> ORGANISM: Corynebacterium glutamicum
<220> FEATURE:
<221> NAME/KEY: misc_feature
<222> LOCATION: (5)..(5)
<223> OTHER INFORMATION: The 'Xaa' at location 5 stands for Lys, Asn,
    Arg, Ser, Thr, Ile, Met, Glu, Asp, Gly, Ala, Val, Gln, His, Pro,
    Leu, Tyr, Trp, Cys, or Phe.

<400> SEQUENCE: 10

```
Met Phe Glu Arg Xaa Ile Val Ala Thr Asp Asn Asn Lys Ala Val Leu
1               5                   10                  15

His Tyr Pro Gly Gly Glu Phe Glu Met Asp Ile Ile Glu Ala Ser Glu
            20                  25                  30

Gly Asn Asn Gly Val Val Leu Gly Lys Met Leu Ser Glu Thr Gly Leu
        35                  40                  45

Ile Thr Phe Asp Pro Gly Tyr Val Ser Thr Gly Ser Thr Glu Ser Lys
    50                  55                  60

Ile Thr Tyr Ile Asp Gly Asp Ala Gly Ile Leu Arg Tyr Arg Gly Tyr
65                  70                  75                  80

Asp Ile Ala Asp Leu Ala Glu Asn Ala Thr Phe Asn Glu Val Ser Tyr
                85                  90                  95

Leu Leu Ile Asn Gly Glu Leu Pro Thr Pro Asp Glu Leu His Lys Phe
            100                 105                 110

Asn Asp Glu Ile Arg His His Thr Leu Leu Asp Glu Asp Phe Lys Ser
        115                 120                 125

Gln Phe Asn Val Phe Pro Arg Asp Ala His Pro Met Ala Thr Leu Ala
    130                 135                 140

Ser Ser Val Asn Ile Leu Ser Thr Tyr Tyr Gln Asp Gln Leu Asn Pro
145                 150                 155                 160
```

```
Leu Asp Glu Ala Gln Leu Asp Lys Ala Thr Val Arg Leu Met Ala Lys
                165                 170                 175

Val Pro Met Leu Ala Ala Tyr Ala His Arg Ala Arg Lys Gly Ala Pro
            180                 185                 190

Tyr Met Tyr Pro Asp Asn Ser Leu Asn Ala Arg Glu Asn Phe Leu Arg
        195                 200                 205

Met Met Phe Gly Tyr Pro Thr Glu Pro Tyr Glu Ile Asp Pro Ile Met
    210                 215                 220

Val Lys Ala Leu Asp Lys Leu Leu Ile Leu His Ala Asp His Glu Gln
225                 230                 235                 240

Asn Cys Ser Thr Ser Thr Val Arg Met Ile Gly Ser Ala Gln Ala Asn
                245                 250                 255

Met Phe Val Ser Ile Ala Gly Ile Asn Ala Leu Ser Gly Pro Leu
            260                 265                 270

His Gly Gly Ala Asn Gln Ala Val Leu Glu Met Leu Glu Asp Ile Lys
        275                 280                 285

Ser Asn His Gly Gly Asp Ala Thr Glu Phe Met Asn Lys Val Lys Asn
    290                 295                 300

Lys Glu Asp Gly Val Arg Leu Met Gly Phe Gly His Arg Val Tyr Lys
305                 310                 315                 320

Asn Tyr Asp Pro Arg Ala Ala Ile Val Lys Glu Thr Ala His Glu Ile
                325                 330                 335

Leu Glu His Leu Gly Gly Asp Asp Leu Leu Asp Leu Ala Ile Lys Leu
            340                 345                 350

Glu Glu Ile Ala Leu Ala Asp Asp Tyr Phe Ile Ser Arg Lys Leu Tyr
        355                 360                 365

Pro Asn Val Asp Phe Tyr Thr Gly Leu Ile Tyr Arg Ala Met Gly Phe
    370                 375                 380

Pro Thr Asp Phe Phe Thr Val Leu Phe Ala Ile Gly Arg Leu Pro Gly
385                 390                 395                 400

Trp Ile Ala His Tyr Arg Glu Gln Leu Gly Ala Ala Gly Asn Lys Ile
                405                 410                 415

Asn Arg Pro Arg Gln Val Tyr Thr Gly Asn Glu Ser Arg Lys Leu Val
            420                 425                 430

Pro Arg Glu Glu Arg
        435

<210> SEQ ID NO 11
<211> LENGTH: 105
<212> TYPE: DNA
<213> ORGANISM: Corynebacterium glutamicum
<220> FEATURE:
<221> NAME/KEY: CDS
<222> LOCATION: (40)..(105)
<220> FEATURE:
<221> NAME/KEY: misc_feature
<222> LOCATION: (52)..(54)
<223> OTHER INFORMATION: n is a, c, g, or t

<400> SEQUENCE: 11
ctacttccgt aatccggaag agttttttc cgaacaaat atg ttt gaa agg nnn        54
                                            Met Phe Glu Arg Xaa
                                             1               5 atc gtg gct act gat aac aac aag gct gtc ctg cac tac ccc ggt ggc    102
Ile Val Ala Thr Asp Asn Asn Lys Ala Val Leu His Tyr Pro Gly Gly
             10                  15                  20 gag                                                                 105
Glu
```

<210> SEQ ID NO 12
<211> LENGTH: 22
<212> TYPE: PRT
<213> ORGANISM: Corynebacterium glutamicum
<220> FEATURE:
<221> NAME/KEY: misc_feature
<222> LOCATION: (5)..(5)
<223> OTHER INFORMATION: The 'Xaa' at location 5 stands for Lys, Asn,
      Arg, Ser, Thr, Ile, Met, Glu, Asp, Gly, Ala, Val, Gln, His, Pro,
      Leu, Tyr, Trp, Cys, or Phe.

<400> SEQUENCE: 12

Met Phe Glu Arg Xaa Ile Val Ala Thr Asp Asn Asn Lys Ala Val Leu
1               5                   10                  15

His Tyr Pro Gly Gly Glu
            20

<210> SEQ ID NO 13
<211> LENGTH: 206
<212> TYPE: DNA
<213> ORGANISM: Corynebacterium glutamicum
<220> FEATURE:
<221> NAME/KEY: CDS
<222> LOCATION: (90)..(206)
<220> FEATURE:
<221> NAME/KEY: misc_feature
<222> LOCATION: (102)..(104)
<223> OTHER INFORMATION: n is a, c, g, or t

<400> SEQUENCE: 13
caaaaactga catgcgcttg gcgcatccca gttggtaaga ataaacggga ctacttccgt      60
aatccggaag agttttttc cgaacaaat atg ttt gaa agg nnn atc gtg gct        113
                                Met Phe Glu Arg Xaa Ile Val Ala
                                1               5 act gat aac aac aag gct gtc ctg cac tac ccc ggt ggc gag ttc gaa       161
Thr Asp Asn Asn Lys Ala Val Leu His Tyr Pro Gly Gly Glu Phe Glu
    10                  15                  20 atg gac atc atc gag gct tct gag ggt aac aac ggt gtt gtc ctg           206
Met Asp Ile Ile Glu Ala Ser Glu Gly Asn Asn Gly Val Val Leu
25                  30                  35

<210> SEQ ID NO 14
<211> LENGTH: 39
<212> TYPE: PRT
<213> ORGANISM: Corynebacterium glutamicum
<220> FEATURE:
<221> NAME/KEY: misc_feature
<222> LOCATION: (5)..(5)
<223> OTHER INFORMATION: The 'Xaa' at location 5 stands for Lys, Asn,
      Arg, Ser, Thr, Ile, Met, Glu, Asp, Gly, Ala, Val, Gln, His, Pro,
      Leu, Tyr, Trp, Cys, or Phe.

<400> SEQUENCE: 14

Met Phe Glu Arg Xaa Ile Val Ala Thr Asp Asn Asn Lys Ala Val Leu
1               5                   10                  15

His Tyr Pro Gly Gly Glu Phe Glu Met Asp Ile Ile Glu Ala Ser Glu
            20                  25                  30

Gly Asn Asn Gly Val Val Leu
        35

<210> SEQ ID NO 15
<211> LENGTH: 405
<212> TYPE: DNA
<213> ORGANISM: Corynebacterium glutamicum
<220> FEATURE:

```
<221> NAME/KEY: CDS
<222> LOCATION: (190)..(405)
<220> FEATURE:
<221> NAME/KEY: misc_feature
<222> LOCATION: (202)..(204)
<223> OTHER INFORMATION: n is a, c, g, or t

<400> SEQUENCE: 15
gattgtgggg gaattggctc tcacttcgga tatggctaaa ccgcatttat cggtatagcg      60
tgttaaccgg accagattgg gaaagaaatg tgtcgagtaa caaaaactga catgcgcttg     120
gcgcatccca gttggtaaga ataaacggga ctacttccgt aatccggaag agtttttttc    180 cgaacaaat atg ttt gaa agg nnn atc gtg gct act gat aac aac aag gct    231
          Met Phe Glu Arg Xaa Ile Val Ala Thr Asp Asn Asn Lys Ala
            1               5                  10 gtc ctg cac tac ccc ggt ggc gag ttc gaa atg gac atc atc gag gct      279
Val Leu His Tyr Pro Gly Gly Glu Phe Glu Met Asp Ile Ile Glu Ala
 15              20                  25                  30 tct gag ggt aac aac ggt gtt gtc ctg ggc aag atg ctg tct gag act      327
Ser Glu Gly Asn Asn Gly Val Val Leu Gly Lys Met Leu Ser Glu Thr
                 35                  40                  45 gga ctg atc act ttt gac cca ggt tat gtg agc act ggc tcc acc gag      375
Gly Leu Ile Thr Phe Asp Pro Gly Tyr Val Ser Thr Gly Ser Thr Glu
             50                  55                  60 tcg aag atc acc tac atc gat ggc gat gcg                               405
Ser Lys Ile Thr Tyr Ile Asp Gly Asp Ala
         65                  70

<210> SEQ ID NO 16
<211> LENGTH: 72
<212> TYPE: PRT
<213> ORGANISM: Corynebacterium glutamicum
<220> FEATURE:
<221> NAME/KEY: misc_feature
<222> LOCATION: (5)..(5)
<223> OTHER INFORMATION: The 'Xaa' at location 5 stands for Lys, Asn,
      Arg, Ser, Thr, Ile, Met, Glu, Asp, Gly, Ala, Val, Gln, His, Pro,
      Leu, Tyr, Trp, Cys, or Phe.

<400> SEQUENCE: 16

Met Phe Glu Arg Xaa Ile Val Ala Thr Asp Asn Asn Lys Ala Val Leu
1               5                   10                  15

His Tyr Pro Gly Gly Glu Phe Glu Met Asp Ile Ile Glu Ala Ser Glu
            20                  25                  30

Gly Asn Asn Gly Val Val Leu Gly Lys Met Leu Ser Glu Thr Gly Leu
        35                  40                  45

Ile Thr Phe Asp Pro Gly Tyr Val Ser Thr Gly Ser Thr Glu Ser Lys
    50                  55                  60

Ile Thr Tyr Ile Asp Gly Asp Ala
65                  70

<210> SEQ ID NO 17
<211> LENGTH: 1001
<212> TYPE: DNA
<213> ORGANISM: Corynebacterium glutamicum
<220> FEATURE:
<221> NAME/KEY: CDS
<222> LOCATION: (489)..(1001)
<220> FEATURE:
<221> NAME/KEY: misc_feature
<222> LOCATION: (501)..(503)
<223> OTHER INFORMATION: n is a, c, g, or t

<400> SEQUENCE: 17
```

```
gttgttaata tccctgagg ttgcgttata gggtggcgaa ttgcatgggg aaagctactc      60
ggcacccatc cttgtcgcgt gcatcacaaa ctttgctaaa ctgtgcacca gtccacttat    120
tgtgggattt ttaatgcctt aaaggccagc attttcaccc tctagcgggg ttgaatgctg    180
gccttgaggg tgcagaacta aatagcagca catcggcaca attgatctga gttctattgg    240
cgtgaccgtg gctactgatt acggtggctg tgggtggtcg ggaatgatgt aaccaacgtg    300
attgtggggg aattggctct cacttcggat atggctaaac cgcatttatc ggtatagcgt    360
gttaaccgga ccagattggg aagaaatgt gtcgagtaac aaaaactgac atgcgcttgg    420
cgcatcccag ttggtaagaa taacggac tacttccgta atccggaaga gttttttcc      480 gaacaaat atg ttt gaa agg nnn atc gtg gct act gat aac aac aag gct     530
         Met Phe Glu Arg Xaa Ile Val Ala Thr Asp Asn Asn Lys Ala
          1               5                  10 gtc ctg cac tac ccc ggt ggc gag ttc gaa atg gac atc atc gag gct      578
Val Leu His Tyr Pro Gly Gly Glu Phe Glu Met Asp Ile Ile Glu Ala
15              20                  25                  30 tct gag ggt aac aac ggt gtt gtc ctg ggc aag atg ctg tct gag act      626
Ser Glu Gly Asn Asn Gly Val Val Leu Gly Lys Met Leu Ser Glu Thr
                35                  40                  45 gga ctg atc act ttt gac cca ggt tat gtg agc act ggc tcc acc gag      674
Gly Leu Ile Thr Phe Asp Pro Gly Tyr Val Ser Thr Gly Ser Thr Glu
            50                  55                  60 tcg aag atc acc tac atc gat ggc gat gcg gga atc ctg cgt tac cgc      722
Ser Lys Ile Thr Tyr Ile Asp Gly Asp Ala Gly Ile Leu Arg Tyr Arg
        65                  70                  75 ggc tat gac atc gct gat ctg gct gag aat gcc acc ttc aac gag gtt      770
Gly Tyr Asp Ile Ala Asp Leu Ala Glu Asn Ala Thr Phe Asn Glu Val
    80                  85                  90 tct tac cta ctt atc aac ggt gag cta cca acc cca gat gag ctt cac      818
Ser Tyr Leu Leu Ile Asn Gly Glu Leu Pro Thr Pro Asp Glu Leu His
95                  100                 105                 110 aag ttt aac gac gag att cgc cac cac acc ctt ctg gac gag gac ttc      866
Lys Phe Asn Asp Glu Ile Arg His His Thr Leu Leu Asp Glu Asp Phe
                115                 120                 125 aag tcc cag ttc aac gtg ttc cca cgc gac gct cac cca atg gca acc      914
Lys Ser Gln Phe Asn Val Phe Pro Arg Asp Ala His Pro Met Ala Thr
            130                 135                 140 ttg gct tcc tcg gtt aac att ttg tct acc tac tac cag gac cag ctg      962
Leu Ala Ser Ser Val Asn Ile Leu Ser Thr Tyr Tyr Gln Asp Gln Leu
        145                 150                 155 aac cca ctc gat gag gca cag ctt gat aag gca acc gtt                 1001
Asn Pro Leu Asp Glu Ala Gln Leu Asp Lys Ala Thr Val
    160                 165                 170

<210> SEQ ID NO 18
<211> LENGTH: 171
<212> TYPE: PRT
<213> ORGANISM: Corynebacterium glutamicum
<220> FEATURE:
<221> NAME/KEY: misc_feature
<222> LOCATION: (5)..(5)
<223> OTHER INFORMATION: The 'Xaa' at location 5 stands for Lys, Asn,
      Arg, Ser, Thr, Ile, Met, Glu, Asp, Gly, Ala, Val, Gln, His, Pro,
      Leu, Tyr, Trp, Cys, or Phe.

<400> SEQUENCE: 18

Met Phe Glu Arg Xaa Ile Val Ala Thr Asp Asn Asn Lys Ala Val Leu
1               5                   10                  15

His Tyr Pro Gly Gly Glu Phe Glu Met Asp Ile Ile Glu Ala Ser Glu
            20                  25                  30
```

-continued

```
Gly Asn Asn Gly Val Val Leu Gly Lys Met Leu Ser Glu Thr Gly Leu
            35                  40                  45

Ile Thr Phe Asp Pro Gly Tyr Val Ser Thr Gly Ser Thr Glu Ser Lys
 50                  55                  60

Ile Thr Tyr Ile Asp Gly Asp Ala Gly Ile Leu Arg Tyr Arg Gly Tyr
65                  70                  75                  80

Asp Ile Ala Asp Leu Ala Glu Asn Ala Thr Phe Asn Glu Val Ser Tyr
                85                  90                  95

Leu Leu Ile Asn Gly Glu Leu Pro Thr Pro Asp Glu Leu His Lys Phe
            100                 105                 110

Asn Asp Glu Ile Arg His His Thr Leu Leu Asp Glu Asp Phe Lys Ser
        115                 120                 125

Gln Phe Asn Val Phe Pro Arg Asp Ala His Pro Met Ala Thr Leu Ala
130                 135                 140

Ser Ser Val Asn Ile Leu Ser Thr Tyr Tyr Gln Asp Gln Leu Asn Pro
145                 150                 155                 160

Leu Asp Glu Ala Gln Leu Asp Lys Ala Thr Val
            165                 170

<210> SEQ ID NO 19
<211> LENGTH: 1263
<212> TYPE: DNA
<213> ORGANISM: Corynebacterium glutamicum
<220> FEATURE:
<221> NAME/KEY: CDS
<222> LOCATION: (1)..(1263)
<223> OTHER INFORMATION: lysC-Wild-Type-Gene

<400> SEQUENCE: 19 gtg gcc ctg gtc gta cag aaa tat ggc ggt tcc tcg ctt gag agt gcg        48
Val Ala Leu Val Val Gln Lys Tyr Gly Gly Ser Ser Leu Glu Ser Ala
 1               5                   10                  15 gaa cgc att aga aac gtc gct gaa cgg atc gtt gcc acc aag aag gct        96
Glu Arg Ile Arg Asn Val Ala Glu Arg Ile Val Ala Thr Lys Lys Ala
            20                  25                  30 gga aat gat gtc gtg gtt gtc tgc tcc gca atg gga gac acc acg gat       144
Gly Asn Asp Val Val Val Val Cys Ser Ala Met Gly Asp Thr Thr Asp
        35                  40                  45 gaa ctt cta gaa ctt gca gcg gca gtg aat ccc gtt ccg cca gct cgt       192
Glu Leu Leu Glu Leu Ala Ala Ala Val Asn Pro Val Pro Pro Ala Arg
 50                  55                  60 gaa atg gat atg ctc ctg act gct ggt gag cgt att tct aac gct ctc       240
Glu Met Asp Met Leu Leu Thr Ala Gly Glu Arg Ile Ser Asn Ala Leu
65                  70                  75                  80 gtc gcc atg gct att gag tcc ctt ggc gca gaa gcc caa tct ttc acg       288
Val Ala Met Ala Ile Glu Ser Leu Gly Ala Glu Ala Gln Ser Phe Thr
                85                  90                  95 ggc tct cag gct ggt gtg ctc acc acc gag cgc cac gga aac gca cgc       336
Gly Ser Gln Ala Gly Val Leu Thr Thr Glu Arg His Gly Asn Ala Arg
            100                 105                 110 att gtt gat gtc act cca ggt cgt gtg cgt gaa gca ctc gat gag ggc       384
Ile Val Asp Val Thr Pro Gly Arg Val Arg Glu Ala Leu Asp Glu Gly
        115                 120                 125 aag atc tgc att gtt gct ggt ttc cag ggt gtt aat aaa gaa acc cgc       432
Lys Ile Cys Ile Val Ala Gly Phe Gln Gly Val Asn Lys Glu Thr Arg
130                 135                 140 gat gtc acc acg ttg ggt cgt ggt ggt tct gac acc act gca gtt gcg       480
Asp Val Thr Thr Leu Gly Arg Gly Gly Ser Asp Thr Thr Ala Val Ala
145                 150                 155                 160
```

```
ttg gca gct gct ttg aac gct gat gtg tgt gag att tac tcg gac gtt      528
Leu Ala Ala Ala Leu Asn Ala Asp Val Cys Glu Ile Tyr Ser Asp Val
            165                 170                 175 gac ggt gtg tat acc gct gac ccg cgc atc gtt cct aat gca cag aag      576
Asp Gly Val Tyr Thr Ala Asp Pro Arg Ile Val Pro Asn Ala Gln Lys
        180                 185                 190 ctg gaa aag ctc agc ttc gaa gaa atg ctg gaa ctt gct gct gtt ggc      624
Leu Glu Lys Leu Ser Phe Glu Glu Met Leu Glu Leu Ala Ala Val Gly
    195                 200                 205 tcc aag att ttg gtg ctg cgc agt gtt gaa tac gct cgt gca ttc aat      672
Ser Lys Ile Leu Val Leu Arg Ser Val Glu Tyr Ala Arg Ala Phe Asn
210                 215                 220 gtg cca ctt cgc gta cgc tcg tct tat agt aat gat ccc ggc act ttg      720
Val Pro Leu Arg Val Arg Ser Ser Tyr Ser Asn Asp Pro Gly Thr Leu
225                 230                 235                 240 att gcc ggc tct atg gag gat att cct gtg gaa gaa gca gtc ctt acc      768
Ile Ala Gly Ser Met Glu Asp Ile Pro Val Glu Glu Ala Val Leu Thr
                245                 250                 255 ggt gtc gca acc gac aag tcc gaa gcc aaa gta acc gtt ctg ggt att      816
Gly Val Ala Thr Asp Lys Ser Glu Ala Lys Val Thr Val Leu Gly Ile
            260                 265                 270 tcc gat aag cca ggc gag gct gcg aag gtt ttc cgt gcg ttg gct gat      864
Ser Asp Lys Pro Gly Glu Ala Ala Lys Val Phe Arg Ala Leu Ala Asp
        275                 280                 285 gca gaa atc aac att gac atg gtt ctg cag aac gtc tct tct gta gaa      912
Ala Glu Ile Asn Ile Asp Met Val Leu Gln Asn Val Ser Ser Val Glu
    290                 295                 300 gac ggc acc acc gac atc acc ttc acc tgc cct cgt tcc gac ggc cgc      960
Asp Gly Thr Thr Asp Ile Thr Phe Thr Cys Pro Arg Ser Asp Gly Arg
305                 310                 315                 320 cgc gcg atg gag atc ttg aag aag ctt cag gtt cag ggc aac tgg acc     1008
Arg Ala Met Glu Ile Leu Lys Lys Leu Gln Val Gln Gly Asn Trp Thr
                325                 330                 335 aat gtg ctt tac gac gac cag gtc ggc aaa gtc tcc ctc gtg ggt gct     1056
Asn Val Leu Tyr Asp Asp Gln Val Gly Lys Val Ser Leu Val Gly Ala
            340                 345                 350 ggc atg aag tct cac cca ggt gtt acc gca gag ttc atg gaa gct ctg     1104
Gly Met Lys Ser His Pro Gly Val Thr Ala Glu Phe Met Glu Ala Leu
        355                 360                 365 cgc gat gtc aac gtg aac atc gaa ttg att tcc acc tct gag att cgt     1152
Arg Asp Val Asn Val Asn Ile Glu Leu Ile Ser Thr Ser Glu Ile Arg
    370                 375                 380 att tcc gtg ctg atc cgt gaa gat gat ctg gat gct gct gca cgt gca     1200
Ile Ser Val Leu Ile Arg Glu Asp Asp Leu Asp Ala Ala Ala Arg Ala
385                 390                 395                 400 ttg cat gag cag ttc cag ctg ggc ggc gaa gac gaa gcc gtc gtt tat     1248
Leu His Glu Gln Phe Gln Leu Gly Gly Glu Asp Glu Ala Val Val Tyr
                405                 410                 415 gca ggc acc gga cgc                                                  1263
Ala Gly Thr Gly Arg
            420

<210> SEQ ID NO 20
<211> LENGTH: 421
<212> TYPE: PRT
<213> ORGANISM: Corynebacterium glutamicum

<400> SEQUENCE: 20

Val Ala Leu Val Val Gln Lys Tyr Gly Gly Ser Ser Leu Glu Ser Ala
1               5                   10                  15
```

-continued

Glu Arg Ile Arg Asn Val Ala Glu Arg Ile Val Ala Thr Lys Lys Ala
            20                  25                  30

Gly Asn Asp Val Val Val Cys Ser Ala Met Gly Asp Thr Thr Asp
        35                  40                  45

Glu Leu Leu Glu Leu Ala Ala Ala Val Asn Pro Val Pro Pro Ala Arg
            50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
            115                 120                 125

Lys Ile Cys Ile Val Ala Gly Phe Gln Gly Val Asn Lys Glu Thr Arg
            130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
            195                 200                 205

Ser Lys Ile Leu Val Leu Arg Ser Val Glu Tyr Ala Arg Ala Phe Asn
            210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
            245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
            275                 280                 285

Ala Glu Ile Asn Ile Asp Met Val Leu Gln Asn Val Ser Ser Val Glu
            290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
            325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
            355                 360                 365

Arg Asp Val Asn Val Asn Ile Glu Leu Ile Ser Thr Ser Glu Ile Arg
            370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
            405                 410                 415

Ala Gly Thr Gly Arg
            420

-continued

```
<210> SEQ ID NO 21
<211> LENGTH: 2266
<212> TYPE: DNA
<213> ORGANISM: Corynebacterium glutamicum
<220> FEATURE:
<221> NAME/KEY: misc_feature
<222> LOCATION: (1)..(500)
<223> OTHER INFORMATION: sequence upstream of the coding region
<220> FEATURE:
<221> NAME/KEY: CDS
<222> LOCATION: (501)..(1763)
<223> OTHER INFORMATION: coding region of lysC-Wild-Type-Gene
<220> FEATURE:
<221> NAME/KEY: misc_feature
<222> LOCATION: (1764)..(2266)
<223> OTHER INFORMATION: sequence dowstream of the coding region

<400> SEQUENCE: 21
cgacaggaca agcactggtt gcactaccaa gagggtgccg aaaccaagtg ctactgtttg        60
taagaaatat gccagcatcg cgtactcatg cctgcccacc acatcggtgt catcagagca       120
ttgagtaaag gtgagctcct tagggagcca tcttttgggg tgcggagcgc gatccggtgt       180
ctgaccacgg tgccccatgc gattgttaat gccgatgcta gggcgaaaag cacggcgagc       240
agattgcttt gcacttgatt cagggtagtt gactaaagag ttgctcgcga agtagcacct       300
gtcacttttg tctcaaatat taaatcgaat atcaatatat ggtctgttta ttggaacgcg       360
tcccagtggc tgagacgcat ccgctaaagc cccaggaacc ctgtgcagaa agaaaacact       420
cctctggcta ggtagacaca gtttataaag gtagagttga gcgggtaact gtcagcacgt       480
agatcgaaag gtgcacaaag gtg gcc ctg gtc gta cag aaa tat ggc ggt tcc       533
                        Val Ala Leu Val Val Gln Lys Tyr Gly Gly Ser
                         1               5                  10 tcg ctt gag agt gcg gaa cgc att aga aac gtc gct gaa cgg atc gtt       581
Ser Leu Glu Ser Ala Glu Arg Ile Arg Asn Val Ala Glu Arg Ile Val
            15                  20                  25 gcc acc aag aag gct gga aat gat gtc gtg gtt gtc tgc tcc gca atg       629
Ala Thr Lys Lys Ala Gly Asn Asp Val Val Val Val Cys Ser Ala Met
        30                  35                  40 gga gac acc acg gat gaa ctt cta gaa ctt gca gcg gca gtg aat ccc       677
Gly Asp Thr Thr Asp Glu Leu Leu Glu Leu Ala Ala Ala Val Asn Pro
 45                  50                  55 gtt ccg cca gct cgt gaa atg gat atg ctc ctg act gct ggt gag cgt       725
Val Pro Pro Ala Arg Glu Met Asp Met Leu Leu Thr Ala Gly Glu Arg
 60                  65                  70                  75 att tct aac gct ctc gtc gcc atg gct att gag tcc ctt ggc gca gaa       773
Ile Ser Asn Ala Leu Val Ala Met Ala Ile Glu Ser Leu Gly Ala Glu
                80                  85                  90 gcc caa tct ttc acg ggc tct cag gct ggt gtg ctc acc acc gag cgc       821
Ala Gln Ser Phe Thr Gly Ser Gln Ala Gly Val Leu Thr Thr Glu Arg
            95                 100                 105 cac gga aac gca cgc att gtt gat gtc act cca ggt cgt gtg cgt gaa       869
His Gly Asn Ala Arg Ile Val Asp Val Thr Pro Gly Arg Val Arg Glu
        110                 115                 120 gca ctc gat gag ggc aag atc tgc att gtt gct ggt ttc cag ggt gtt       917
Ala Leu Asp Glu Gly Lys Ile Cys Ile Val Ala Gly Phe Gln Gly Val
125                 130                 135 aat aaa gaa acc cgc gat gtc acc acg ttg ggt cgt ggt ggt tct gac       965
Asn Lys Glu Thr Arg Asp Val Thr Thr Leu Gly Arg Gly Gly Ser Asp
140                 145                 150                 155 acc act gca gtt gcg ttg gca gct gct ttg aac gct gat gtg tgt gag      1013
Thr Thr Ala Val Ala Leu Ala Ala Ala Leu Asn Ala Asp Val Cys Glu
                160                 165                 170
```

```
att tac tcg gac gtt gac ggt gtg tat acc gct gac ccg cgc atc gtt      1061
Ile Tyr Ser Asp Val Asp Gly Val Tyr Thr Ala Asp Pro Arg Ile Val
            175                 180                 185 cct aat gca cag aag ctg gaa aag ctc agc ttc gaa gaa atg ctg gaa      1109
Pro Asn Ala Gln Lys Leu Glu Lys Leu Ser Phe Glu Glu Met Leu Glu
        190                 195                 200 ctt gct gct gtt ggc tcc aag att ttg gtg ctg cgc agt gtt gaa tac      1157
Leu Ala Ala Val Gly Ser Lys Ile Leu Val Leu Arg Ser Val Glu Tyr
    205                 210                 215 gct cgt gca ttc aat gtg cca ctt cgc gta cgc tcg tct tat agt aat      1205
Ala Arg Ala Phe Asn Val Pro Leu Arg Val Arg Ser Ser Tyr Ser Asn
220                 225                 230                 235 gat ccc ggc act ttg att gcc ggc tct atg gag gat att cct gtg gaa      1253
Asp Pro Gly Thr Leu Ile Ala Gly Ser Met Glu Asp Ile Pro Val Glu
            240                 245                 250 gaa gca gtc ctt acc ggt gtc gca acc gac aag tcc gaa gcc aaa gta      1301
Glu Ala Val Leu Thr Gly Val Ala Thr Asp Lys Ser Glu Ala Lys Val
        255                 260                 265 acc gtt ctg ggt att tcc gat aag cca ggc gag gct gcg aag gtt ttc      1349
Thr Val Leu Gly Ile Ser Asp Lys Pro Gly Glu Ala Ala Lys Val Phe
    270                 275                 280 cgt gcg ttg gct gat gca gaa atc aac att gac atg gtt ctg cag aac      1397
Arg Ala Leu Ala Asp Ala Glu Ile Asn Ile Asp Met Val Leu Gln Asn
285                 290                 295 gtc tct tct gta gaa gac ggc acc acc gac atc acc ttc acc tgc cct      1445
Val Ser Ser Val Glu Asp Gly Thr Thr Asp Ile Thr Phe Thr Cys Pro
300                 305                 310                 315 cgt tcc gac ggc cgc cgc gcg atg gag atc ttg aag aag ctt cag gtt      1493
Arg Ser Asp Gly Arg Arg Ala Met Glu Ile Leu Lys Lys Leu Gln Val
            320                 325                 330 cag ggc aac tgg acc aat gtg ctt tac gac gac cag gtc ggc aaa gtc      1541
Gln Gly Asn Trp Thr Asn Val Leu Tyr Asp Asp Gln Val Gly Lys Val
        335                 340                 345 tcc ctc gtg ggt gct ggc atg aag tct cac cca ggt gtt acc gca gag      1589
Ser Leu Val Gly Ala Gly Met Lys Ser His Pro Gly Val Thr Ala Glu
    350                 355                 360 ttc atg gaa gct ctg cgc gat gtc aac gtg aac atc gaa ttg att tcc      1637
Phe Met Glu Ala Leu Arg Asp Val Asn Val Asn Ile Glu Leu Ile Ser
365                 370                 375 acc tct gag att cgt att tcc gtg ctg atc cgt gaa gat gat ctg gat      1685
Thr Ser Glu Ile Arg Ile Ser Val Leu Ile Arg Glu Asp Asp Leu Asp
380                 385                 390                 395 gct gct gca cgt gca ttg cat gag cag ttc cag ctg ggc ggc gaa gac      1733
Ala Ala Ala Arg Ala Leu His Glu Gln Phe Gln Leu Gly Gly Glu Asp
            400                 405                 410 gaa gcc gtc gtt tat gca ggc acc gga cgc taaagtttta aggagtagt        1783
Glu Ala Val Val Tyr Ala Gly Thr Gly Arg
        415                 420 tttacaatga ccaccatcgc agttgttggt gcaaccggcc aggtcggcca ggttatgcgc   1843
acccttttgg aagagcgcaa tttcccagct gacactgttc gtttctttgc ttccccacgt   1903
tccgcaggcc gtaagattga attccgtggc acggaaatcg aggtagaaga cattactcag   1963
gcaaccgagg agtccctcaa ggacatcgac gttgcgttgt ctccgctgg aggcaccgct   2023 tccaagcagt acgctccact gttcgctgct gcaggcgcga ctgttgtgga taactcttct   2083
gcttggcgca aggacgacga ggttccacta atcgtctctg aggtgaaccc ttccgacaag   2143
gattccctgg tcaagggcat tattgcgaac cctaactgca ccaccatggc tgcgatgcca   2203
```

-continued

```
gtgctgaagc cacttcacga tgccgctggt cttgtaaagc ttcacgtttc ctcttaccag    2263
gct                                                                  2266
```

<210> SEQ ID NO 22
<211> LENGTH: 421
<212> TYPE: PRT
<213> ORGANISM: Corynebacterium glutamicum

<400> SEQUENCE: 22

| | | | | | | | | | | | | | | |
|---|---|---|---|---|---|---|---|---|---|---|---|---|---|---|
| Val | Ala | Leu | Val | Val | Gln | Lys | Tyr | Gly | Gly | Ser | Ser | Leu | Glu | Ser | Ala |
| 1 | | | | 5 | | | | | 10 | | | | | 15 | |
| Glu | Arg | Ile | Arg | Asn | Val | Ala | Glu | Arg | Ile | Val | Ala | Thr | Lys | Lys | Ala |
| | | | 20 | | | | | 25 | | | | | 30 | | |
| Gly | Asn | Asp | Val | Val | Val | Cys | Ser | Ala | Met | Gly | Asp | Thr | Thr | Asp |
| | | 35 | | | | | 40 | | | | | 45 | | |
| Glu | Leu | Leu | Glu | Leu | Ala | Ala | Ala | Val | Asn | Pro | Val | Pro | Pro | Ala | Arg |
| 50 | | | | | 55 | | | | | 60 | | | | | |
| Glu | Met | Asp | Met | Leu | Leu | Thr | Ala | Gly | Glu | Arg | Ile | Ser | Asn | Ala | Leu |
| 65 | | | | 70 | | | | | 75 | | | | | 80 | |
| Val | Ala | Met | Ala | Ile | Glu | Ser | Leu | Gly | Ala | Glu | Ala | Gln | Ser | Phe | Thr |
| | | | | 85 | | | | | 90 | | | | | 95 | |
| Gly | Ser | Gln | Ala | Gly | Val | Leu | Thr | Thr | Glu | Arg | His | Gly | Asn | Ala | Arg |
| | | | 100 | | | | | 105 | | | | | 110 | | |
| Ile | Val | Asp | Val | Thr | Pro | Gly | Arg | Val | Arg | Glu | Ala | Leu | Asp | Glu | Gly |
| | | 115 | | | | | 120 | | | | | 125 | | | |
| Lys | Ile | Cys | Ile | Val | Ala | Gly | Phe | Gln | Gly | Val | Asn | Lys | Glu | Thr | Arg |
| 130 | | | | | 135 | | | | | 140 | | | | | |
| Asp | Val | Thr | Thr | Leu | Gly | Arg | Gly | Gly | Ser | Asp | Thr | Thr | Ala | Val | Ala |
| 145 | | | | | 150 | | | | | 155 | | | | | 160 |
| Leu | Ala | Ala | Ala | Leu | Asn | Ala | Asp | Val | Cys | Glu | Ile | Tyr | Ser | Asp | Val |
| | | | | 165 | | | | | 170 | | | | | 175 | |
| Asp | Gly | Val | Tyr | Thr | Ala | Asp | Pro | Arg | Ile | Val | Pro | Asn | Ala | Gln | Lys |
| | | | 180 | | | | | 185 | | | | | 190 | | |
| Leu | Glu | Lys | Leu | Ser | Phe | Glu | Glu | Met | Leu | Glu | Leu | Ala | Ala | Val | Gly |
| | | 195 | | | | | 200 | | | | | 205 | | | |
| Ser | Lys | Ile | Leu | Val | Leu | Arg | Ser | Val | Glu | Tyr | Ala | Arg | Ala | Phe | Asn |
| 210 | | | | | 215 | | | | | 220 | | | | | |
| Val | Pro | Leu | Arg | Val | Arg | Ser | Ser | Tyr | Ser | Asn | Asp | Pro | Gly | Thr | Leu |
| 225 | | | | | 230 | | | | | 235 | | | | | 240 |
| Ile | Ala | Gly | Ser | Met | Glu | Asp | Ile | Pro | Val | Glu | Glu | Ala | Val | Leu | Thr |
| | | | | 245 | | | | | 250 | | | | | 255 | |
| Gly | Val | Ala | Thr | Asp | Lys | Ser | Glu | Ala | Lys | Val | Thr | Val | Leu | Gly | Ile |
| | | | 260 | | | | | 265 | | | | | 270 | | |
| Ser | Asp | Lys | Pro | Gly | Glu | Ala | Ala | Lys | Val | Phe | Arg | Ala | Leu | Ala | Asp |
| | | 275 | | | | | 280 | | | | | 285 | | | |
| Ala | Glu | Ile | Asn | Ile | Asp | Met | Val | Leu | Gln | Asn | Val | Ser | Ser | Val | Glu |
| | 290 | | | | | 295 | | | | | 300 | | | | |
| Asp | Gly | Thr | Thr | Asp | Ile | Thr | Phe | Thr | Cys | Pro | Arg | Ser | Asp | Gly | Arg |
| 305 | | | | | 310 | | | | | 315 | | | | | 320 |
| Arg | Ala | Met | Glu | Ile | Leu | Lys | Lys | Leu | Gln | Val | Gln | Gly | Asn | Trp | Thr |
| | | | | 325 | | | | | 330 | | | | | 335 | |
| Asn | Val | Leu | Tyr | Asp | Asp | Gln | Val | Gly | Lys | Val | Ser | Leu | Val | Gly | Ala |
| | | | 340 | | | | | 345 | | | | | 350 | | |
| Gly | Met | Lys | Ser | His | Pro | Gly | Val | Thr | Ala | Glu | Phe | Met | Glu | Ala | Leu |

-continued

```
                355                 360                 365
Arg Asp Val Asn Val Asn Ile Glu Leu Ile Ser Thr Ser Glu Ile Arg
        370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420

<210> SEQ ID NO 23
<211> LENGTH: 1503
<212> TYPE: DNA
<213> ORGANISM: Corynebacterium glutamicum
<220> FEATURE:
<221> NAME/KEY: CDS
<222> LOCATION: (1)..(1500)
<223> OTHER INFORMATION: mqo-Wild-Type-Gene

<400> SEQUENCE: 23 atg tca gat tcc ccg aag aac gca ccg agg att acc gat gag gca gat      48
Met Ser Asp Ser Pro Lys Asn Ala Pro Arg Ile Thr Asp Glu Ala Asp
1               5                   10                  15 gta gtt ctc att ggt gcc ggt atc atg agc tcc acg ctg ggt gca atg      96
Val Val Leu Ile Gly Ala Gly Ile Met Ser Ser Thr Leu Gly Ala Met
                20                  25                  30 ctg cgt cag ctg gag cca agc tgg act cag atc gtc ttc gag cgt ttg      144
Leu Arg Gln Leu Glu Pro Ser Trp Thr Gln Ile Val Phe Glu Arg Leu
            35                  40                  45 gat gga ccg gca caa gag tcg tcc tcc ccg tgg aac aat gca gga acc      192
Asp Gly Pro Ala Gln Glu Ser Ser Ser Pro Trp Asn Asn Ala Gly Thr
        50                  55                  60 ggc cac tct gct cta tgc gag ctg aac tac acc cca gag gtt aag ggc      240
Gly His Ser Ala Leu Cys Glu Leu Asn Tyr Thr Pro Glu Val Lys Gly
65                  70                  75                  80 aag gtt gaa att gcc aag gct gta gga atc aac gag aag ttc cag gtt      288
Lys Val Glu Ile Ala Lys Ala Val Gly Ile Asn Glu Lys Phe Gln Val
                85                  90                  95 tcc cgt cag ttc tgg tct cac ctc gtt gaa gag gga gtg ctg tct gat      336
Ser Arg Gln Phe Trp Ser His Leu Val Glu Glu Gly Val Leu Ser Asp
            100                 105                 110 cct aag gaa ttc atc aac cct gtt cct cac gta tct ttc ggc cag ggc      384
Pro Lys Glu Phe Ile Asn Pro Val Pro His Val Ser Phe Gly Gln Gly
        115                 120                 125 gca gat cag gtt gca tac atc aag gct cgc tac gaa gct ttg aag gat      432
Ala Asp Gln Val Ala Tyr Ile Lys Ala Arg Tyr Glu Ala Leu Lys Asp
130                 135                 140 cac cca ctc ttc cag ggc atg acc tac gct gac gat gaa gct acc ttc      480
His Pro Leu Phe Gln Gly Met Thr Tyr Ala Asp Asp Glu Ala Thr Phe
145                 150                 155                 160 acc gag aag ctg cct ttg atg gca aag ggc cgt gac ttc tct gat cca      528
Thr Glu Lys Leu Pro Leu Met Ala Lys Gly Arg Asp Phe Ser Asp Pro
                165                 170                 175 gta gca atc tct tgg atc gat gaa ggc acc gac atc aac tac ggt gct      576
Val Ala Ile Ser Trp Ile Asp Glu Gly Thr Asp Ile Asn Tyr Gly Ala
            180                 185                 190 cag acc aag cag tac ctg gat gca gct gaa gtt gaa ggc act gaa atc      624
Gln Thr Lys Gln Tyr Leu Asp Ala Ala Glu Val Glu Gly Thr Glu Ile
        195                 200                 205 cgc tat ggc cac gaa gtc aag agc atc aag gct gat ggc gca aag tgg      672
```

```
                Arg Tyr Gly His Glu Val Lys Ser Ile Lys Ala Asp Gly Ala Lys Trp
                    210                 215                 220 atc gtg acc gtc aag aac gta cac act ggc gac acc aag acc atc aag      720
Ile Val Thr Val Lys Asn Val His Thr Gly Asp Thr Lys Thr Ile Lys
225                 230                 235                 240 gca aac ttc gtg ttc gtc ggc gca ggc gga tac gca ctg gat ctg ctt      768
Ala Asn Phe Val Phe Val Gly Ala Gly Gly Tyr Ala Leu Asp Leu Leu
                245                 250                 255 cgc agc gca ggc atc cca cag gtc aag ggc ttc gct gga ttc cca gta      816
Arg Ser Ala Gly Ile Pro Gln Val Lys Gly Phe Ala Gly Phe Pro Val
            260                 265                 270 tcc ggc ctg tgg ctt cgt tgc acc aac gag gaa ctg atc gag cag cac      864
Ser Gly Leu Trp Leu Arg Cys Thr Asn Glu Glu Leu Ile Glu Gln His
        275                 280                 285 gca gcc aag gta tat ggc aag gca tct gtt ggc gct cct cca atg tct      912
Ala Ala Lys Val Tyr Gly Lys Ala Ser Val Gly Ala Pro Pro Met Ser
    290                 295                 300 gtt cct cac ctt gac acc cgc gtt atc gag ggt gaa aag ggt ctg ctc      960
Val Pro His Leu Asp Thr Arg Val Ile Glu Gly Glu Lys Gly Leu Leu
305                 310                 315                 320 ttt gga cct tac ggt ggc tgg acc cct aag ttc ttg aag gaa ggc tcc     1008
Phe Gly Pro Tyr Gly Gly Trp Thr Pro Lys Phe Leu Lys Glu Gly Ser
                325                 330                 335 tac ctg gac ctg ttc aag tcc atc cgc cca gac aac att cct tcc tac     1056
Tyr Leu Asp Leu Phe Lys Ser Ile Arg Pro Asp Asn Ile Pro Ser Tyr
                340                 345                 350 ctt ggc gtt gct gct cag gaa ttt gat ctg acc aag tac ctt gtc act     1104
Leu Gly Val Ala Ala Gln Glu Phe Asp Leu Thr Lys Tyr Leu Val Thr
            355                 360                 365 gaa gtt ctc aag gac cag gac aag cgt atg gat gct ctt cgc gag tac     1152
Glu Val Leu Lys Asp Gln Asp Lys Arg Met Asp Ala Leu Arg Glu Tyr
        370                 375                 380 atg cca gag gca caa aac ggc gat tgg gag acc atc gtt gcc gga cag     1200
Met Pro Glu Ala Gln Asn Gly Asp Trp Glu Thr Ile Val Ala Gly Gln
385                 390                 395                 400 cgt gtt cag gtt att aag cct gca gga ttc cct aag ttc ggt tcc ctg     1248
Arg Val Gln Val Ile Lys Pro Ala Gly Phe Pro Lys Phe Gly Ser Leu
                405                 410                 415 gaa ttc ggc acc acc ttg atc aac aac tcc gaa ggc acc atc gcc gga     1296
Glu Phe Gly Thr Thr Leu Ile Asn Asn Ser Glu Gly Thr Ile Ala Gly
                420                 425                 430 ttg ctc ggt gct tcc cct gga gca tcc atc gca cct tcc gca atg atc     1344
Leu Leu Gly Ala Ser Pro Gly Ala Ser Ile Ala Pro Ser Ala Met Ile
            435                 440                 445 gag ctg ctt gag cgt tgc ttc ggt gac cgc atg atc gag tgg ggc gac     1392
Glu Leu Leu Glu Arg Cys Phe Gly Asp Arg Met Ile Glu Trp Gly Asp
        450                 455                 460 aag ctg aag gac atg atc cct tcc tac ggc aag aag ctt gct tcc gag     1440
Lys Leu Lys Asp Met Ile Pro Ser Tyr Gly Lys Lys Leu Ala Ser Glu
465                 470                 475                 480 cca gca ctg ttt gag cag cag tgg gca cgc acc cag aag acc ctg aag     1488
Pro Ala Leu Phe Glu Gln Gln Trp Ala Arg Thr Gln Lys Thr Leu Lys
                485                 490                 495 ctt gag gaa gcc taa                                                  1503
Leu Glu Glu Ala
            500

<210> SEQ ID NO 24
<211> LENGTH: 500
<212> TYPE: PRT
```

<213> ORGANISM: Corynebacterium glutamicum

<400> SEQUENCE: 24

```
Met Ser Asp Ser Pro Lys Asn Ala Pro Arg Ile Thr Asp Glu Ala Asp
1               5                   10                  15

Val Val Leu Ile Gly Ala Gly Ile Met Ser Ser Thr Leu Gly Ala Met
            20                  25                  30

Leu Arg Gln Leu Glu Pro Ser Trp Thr Gln Ile Val Phe Glu Arg Leu
        35                  40                  45

Asp Gly Pro Ala Gln Glu Ser Ser Pro Trp Asn Asn Ala Gly Thr
    50                  55                  60

Gly His Ser Ala Leu Cys Glu Leu Asn Tyr Thr Pro Glu Val Lys Gly
65                  70                  75                  80

Lys Val Glu Ile Ala Lys Ala Val Gly Ile Asn Glu Lys Phe Gln Val
                85                  90                  95

Ser Arg Gln Phe Trp Ser His Leu Val Glu Glu Gly Val Leu Ser Asp
            100                 105                 110

Pro Lys Glu Phe Ile Asn Pro Val Pro His Val Ser Phe Gly Gln Gly
        115                 120                 125

Ala Asp Gln Val Ala Tyr Ile Lys Ala Arg Tyr Glu Ala Leu Lys Asp
    130                 135                 140

His Pro Leu Phe Gln Gly Met Thr Tyr Ala Asp Asp Glu Ala Thr Phe
145                 150                 155                 160

Thr Glu Lys Leu Pro Leu Met Ala Lys Gly Arg Asp Phe Ser Asp Pro
                165                 170                 175

Val Ala Ile Ser Trp Ile Asp Glu Gly Thr Asp Ile Asn Tyr Gly Ala
            180                 185                 190

Gln Thr Lys Gln Tyr Leu Asp Ala Ala Glu Val Glu Gly Thr Glu Ile
        195                 200                 205

Arg Tyr Gly His Glu Val Lys Ser Ile Lys Ala Asp Gly Ala Lys Trp
    210                 215                 220

Ile Val Thr Val Lys Asn Val His Thr Gly Asp Thr Lys Thr Ile Lys
225                 230                 235                 240

Ala Asn Phe Val Phe Val Gly Ala Gly Gly Tyr Ala Leu Asp Leu Leu
                245                 250                 255

Arg Ser Ala Gly Ile Pro Gln Val Lys Gly Phe Ala Gly Phe Pro Val
            260                 265                 270

Ser Gly Leu Trp Leu Arg Cys Thr Asn Glu Glu Leu Ile Glu Gln His
        275                 280                 285

Ala Ala Lys Val Tyr Gly Lys Ala Ser Val Gly Ala Pro Pro Met Ser
    290                 295                 300

Val Pro His Leu Asp Thr Arg Val Ile Glu Gly Lys Gly Leu Leu
305                 310                 315                 320

Phe Gly Pro Tyr Gly Gly Trp Thr Pro Lys Phe Leu Lys Glu Gly Ser
                325                 330                 335

Tyr Leu Asp Leu Phe Lys Ser Ile Arg Pro Asp Asn Ile Pro Ser Tyr
            340                 345                 350

Leu Gly Val Ala Ala Gln Glu Phe Asp Leu Thr Lys Tyr Leu Val Thr
        355                 360                 365

Glu Val Leu Lys Asp Gln Asp Lys Arg Met Asp Ala Leu Arg Glu Tyr
    370                 375                 380

Met Pro Glu Ala Gln Asn Gly Asp Trp Glu Thr Ile Val Ala Gly Gln
385                 390                 395                 400
```

-continued

```
Arg Val Gln Val Ile Lys Pro Ala Gly Phe Pro Lys Phe Gly Ser Leu
                405                 410                 415

Glu Phe Gly Thr Thr Leu Ile Asn Asn Ser Glu Gly Thr Ile Ala Gly
            420                 425                 430

Leu Leu Gly Ala Ser Pro Gly Ala Ser Ile Ala Pro Ser Ala Met Ile
            435                 440                 445

Glu Leu Leu Glu Arg Cys Phe Gly Asp Arg Met Ile Glu Trp Gly Asp
450                 455                 460

Lys Leu Lys Asp Met Ile Pro Ser Tyr Gly Lys Lys Leu Ala Ser Glu
465                 470                 475                 480

Pro Ala Leu Phe Glu Gln Gln Trp Ala Arg Thr Gln Lys Thr Leu Lys
                485                 490                 495

Leu Glu Glu Ala
            500

<210> SEQ ID NO 25
<211> LENGTH: 3314
<212> TYPE: DNA
<213> ORGANISM: Corynebacterium glutamicum
<220> FEATURE:
<221> NAME/KEY: misc_feature
<222> LOCATION: (1)..(1000)
<223> OTHER INFORMATION: sequence upstream of the coding region
<220> FEATURE:
<221> NAME/KEY: CDS
<222> LOCATION: (1001)..(2311)
<223> OTHER INFORMATION: gltA-Wildtype-Gene
<220> FEATURE:
<221> NAME/KEY: misc_feature
<222> LOCATION: (1013)..(1015)
<220> FEATURE:
<221> NAME/KEY: misc_feature
<222> LOCATION: (2312)..(3314)
<223> OTHER INFORMATION: sequence downstream of the coding region

<400> SEQUENCE: 25
atgagtccga aggttgctgc atcccagaat gcggtcgcac cacctaggga aaggatgatc      60
tcgtagcctt ctggaaggga gaagaggtcg gagagtccct cgcggattga acccacgacg     120 tttttactg ccggctgacg gtgtgaggta ccgatgacgg atgcggatcc gtcgacaata      180
gcctgaatct gttctggtcg aaccttggaa ggtccgcagc cgaaacggcc gtcgccaggg     240
atgaactcag agggcagggt ggggaagtcg gtcatgtctt cgggcaactt tctgcgcttg     300
gaagtaaaag ggccagggat cgttaacgat ctgacccaac aactataacc ctgaagctgt     360
cagttcctag cacccctagat tcttcacgca gtctcccaaa cgatgaaaaa cgcccaaaac    420
tggcgacacc gaactattga aaacgcgggg attagttgac cagccaccaa tttgggggta    480
gctcaaagtt ttgcaaagtt ttcaatttct aggttgttaa tatccctga ggttgcgtta     540 tagggtggcg aattgcatgg ggaaagctac tcggcaccca tccttgtcgc gtgcatcaca    600
aactttgcta actgtgcac cagtccactt attgtggat ttttaatgcc ttaaaggcca      660
gcattttcac cctctagcgg ggttgaatgc tggccttgag ggtgcagaac taaatagcag    720
cacatcggca caattgatct gagttctatt ggcgtgaccg tggctactga ttacggtggc    780
tgtgggtggt cgggaatgat gtaaccaacg tgattgtggg ggaattggct ctcacttcgg    840
atatggctaa accgcatta tcggtatagc gtgttaaccg gaccagattg ggaaagaaat    900
gtgtcgagta acaaaaactg acatgcgctt ggcgcatccc agttggtaag aataaacggg    960
actacttccg taatccggaa gagttttttt ccgaacaaat atg ttt gaa agg gat    1015
                                                Met Phe Glu Arg Asp
                                                 1               5
```

```
atc gtg gct act gat aac aac aag gct gtc ctg cac tac ccc ggt ggc    1063
Ile Val Ala Thr Asp Asn Asn Lys Ala Val Leu His Tyr Pro Gly Gly
             10                  15                  20 gag ttc gaa atg gac atc atc gag gct tct gag ggt aac aac ggt gtt    1111
Glu Phe Glu Met Asp Ile Ile Glu Ala Ser Glu Gly Asn Asn Gly Val
         25                  30                  35 gtc ctg ggc aag atg ctg tct gag act gga ctg atc act ttt gac cca    1159
Val Leu Gly Lys Met Leu Ser Glu Thr Gly Leu Ile Thr Phe Asp Pro
                 40                  45                  50 ggt tat gtg agc act ggc tcc acc gag tcg aag atc acc tac atc gat    1207
Gly Tyr Val Ser Thr Gly Ser Thr Glu Ser Lys Ile Thr Tyr Ile Asp
             55                  60                  65 ggc gat gcg gga atc ctg cgt tac cgc ggc tat gac atc gct gat ctg    1255
Gly Asp Ala Gly Ile Leu Arg Tyr Arg Gly Tyr Asp Ile Ala Asp Leu
 70                  75                  80                  85 gct gag aat gcc acc ttc aac gag gtt tct tac cta ctt atc aac ggt    1303
Ala Glu Asn Ala Thr Phe Asn Glu Val Ser Tyr Leu Leu Ile Asn Gly
                 90                  95                 100 gag cta cca acc cca gat gag ctt cac aag ttt aac gac gag att cgc    1351
Glu Leu Pro Thr Pro Asp Glu Leu His Lys Phe Asn Asp Glu Ile Arg
             105                 110                 115 cac cac acc ctt ctg gac gag gac ttc aag tcc cag ttc aac gtg ttc    1399
His His Thr Leu Leu Asp Glu Asp Phe Lys Ser Gln Phe Asn Val Phe
         120                 125                 130 cca cgc gac gct cac cca atg gca acc ttg gct tcc tcg gtt aac att    1447
Pro Arg Asp Ala His Pro Met Ala Thr Leu Ala Ser Ser Val Asn Ile
             135                 140                 145 ttg tct acc tac tac cag gac cag ctg aac cca ctc gat gag gca cag    1495
Leu Ser Thr Tyr Tyr Gln Asp Gln Leu Asn Pro Leu Asp Glu Ala Gln
150                 155                 160                 165 ctt gat aag gca acc gtt cgc ctc atg gca aag gtt cca atg ctg gct    1543
Leu Asp Lys Ala Thr Val Arg Leu Met Ala Lys Val Pro Met Leu Ala
                 170                 175                 180 gcg tac gca cac cgc gca cgc aag ggt gct cct tac atg tac cca gac    1591
Ala Tyr Ala His Arg Ala Arg Lys Gly Ala Pro Tyr Met Tyr Pro Asp
             185                 190                 195 aac tcc ctc aat gcg cgt gag aac ttc ctg cgc atg atg ttc ggt tac    1639
Asn Ser Leu Asn Ala Arg Glu Asn Phe Leu Arg Met Met Phe Gly Tyr
         200                 205                 210 cca acc gag cca tac gag atc gac cca atc atg gtc aag gct ctg gac    1687
Pro Thr Glu Pro Tyr Glu Ile Asp Pro Ile Met Val Lys Ala Leu Asp
             215                 220                 225 aag ctg ctc atc ctg cac gct gac cac gag cag aac tgc tcc acc tcc    1735
Lys Leu Leu Ile Leu His Ala Asp His Glu Gln Asn Cys Ser Thr Ser
230                 235                 240                 245 acc gtt cgt atg atc ggt tcc gca cag gcc aac atg ttt gtc tcc atc    1783
Thr Val Arg Met Ile Gly Ser Ala Gln Ala Asn Met Phe Val Ser Ile
                 250                 255                 260 gct ggt ggc atc aac gct ctg tcc ggc cca ctg cac ggt ggc gca aac    1831
Ala Gly Gly Ile Asn Ala Leu Ser Gly Pro Leu His Gly Gly Ala Asn
             265                 270                 275 cag gct gtt ctg gag atg ctc gaa gac atc aag agc aac cac ggt ggc    1879
Gln Ala Val Leu Glu Met Leu Glu Asp Ile Lys Ser Asn His Gly Gly
         280                 285                 290 gac gca acc gag ttc atg aac aag gtc aag aac aag gaa gac ggc gtc    1927
Asp Ala Thr Glu Phe Met Asn Lys Val Lys Asn Lys Glu Asp Gly Val
295                 300                 305 cgc ctc atg ggc ttc gga cac cgc gtt tac aag aac tac gat cca cgt    1975
Arg Leu Met Gly Phe Gly His Arg Val Tyr Lys Asn Tyr Asp Pro Arg
```

-continued

| | | | | | | | | | | | | | |
|---|---|---|---|---|---|---|---|---|---|---|---|---|---|
| 310 | | | | 315 | | | | 320 | | | | 325 | |
| gca | gca | atc | gtc | aag | gag | acc | gca | cac | gag | atc | ctc | gag | cac ctc ggt | 2023 |
| Ala | Ala | Ile | Val | Lys | Glu | Thr | Ala | His | Glu | Ile | Leu | Glu | His Leu Gly |
| | | | 330 | | | | | 335 | | | | 340 | |
| ggc | gac | gat | ctt | ctg | gat | ctg | gca | atc | aag | ctg | gaa | gaa | att gca ctg | 2071 |
| Gly | Asp | Asp | Leu | Leu | Asp | Leu | Ala | Ile | Lys | Leu | Glu | Glu | Ile Ala Leu |
| | | | 345 | | | | | 350 | | | | 355 | |
| gct | gat | gat | tac | ttc | atc | tcc | cgc | aag | ctc | tac | ccg | aac | gta gac ttc | 2119 |
| Ala | Asp | Asp | Tyr | Phe | Ile | Ser | Arg | Lys | Leu | Tyr | Pro | Asn | Val Asp Phe |
| | | | 360 | | | | | 365 | | | | 370 | |
| tac | acc | ggc | ctg | atc | tac | cgc | gca | atg | ggc | ttc | cca | act | gac ttc ttc | 2167 |
| Tyr | Thr | Gly | Leu | Ile | Tyr | Arg | Ala | Met | Gly | Phe | Pro | Thr | Asp Phe Phe |
| | 375 | | | | | 380 | | | | | 385 | | |
| acc | gta | ttg | ttc | gca | atc | ggt | cgt | ctg | cca | gga | tgg | atc | gct cac tac | 2215 |
| Thr | Val | Leu | Phe | Ala | Ile | Gly | Arg | Leu | Pro | Gly | Trp | Ile | Ala His Tyr |
| 390 | | | | | 395 | | | | | 400 | | | | 405 |
| cgc | gag | cag | ctc | ggt | gca | gca | ggc | aac | aag | atc | aac | cgc | cca cgc cag | 2263 |
| Arg | Glu | Gln | Leu | Gly | Ala | Ala | Gly | Asn | Lys | Ile | Asn | Arg | Pro Arg Gln |
| | | | | 410 | | | | | 415 | | | | 420 |
| gtc | tac | acc | ggc | aac | gaa | tcc | cgc | aag | ttg | gtt | cct | cgc | gag gag cgc | 2311 |
| Val | Tyr | Thr | Gly | Asn | Glu | Ser | Arg | Lys | Leu | Val | Pro | Arg | Glu Glu Arg |
| | | | 425 | | | | | 430 | | | | 435 | |

```
taaatttagc ggatgattct cgttcaactt cggccgaagc cacttcgtct gtcataatga   2371
cagggatggt ttcggccgtt tttgcatgaa accaaaaaat acgattttca aggagcatgt   2431
acagcacatg gaaaagccac agattgagct accggtcggt ccagcaccgg aagatctcgt   2491
aatctctgac atcatcgttg gcgaaggagc agaagcccgc ccaggtggag aagttgaggt   2551
ccactatgtg ggcgttgact ttgaaaccgg cgaggagttt gactcttcct gggatcgtgg   2611
acagaccagc cagttcccac tcaacggcct cattgcaggt tggcaagagg gaattccagg   2671
catgaaggtc ggcggacgtc gtcagctgac cattccgcca gaggctgctt acggccctga   2731
gggttccggc cacccactgt ctggccgtac cctggtgttc atcatcgatt tgatcagcgc   2791
ataatttct ttactgcgct aaacgctcaa atcgtgtgaa gcgactgtcg cgtcccgccc   2851
tctccggatt gttatccaat tcggagaggg cgttgctgat tgtgccgaga atttcttcaa   2911
caaagtgctc ggtttcggcg acgatcccgt cgataagccc ttggcttaaa agtgcgtgcg   2971
cctgcacgcc ttgtcgctct atgatttccg cggcgtggtt ggtgtcgcgg aagaggatgg   3031
ccgaggcgcc ctctggtggc aatgcggaca gccacgcgtt ttcggccgcg tagaccagat   3091
cggcgggcag catggccagc gcgccaccgc caacgccctg accaataatg accgaaacgg   3151
tggggagggg agcgtcgata agcttggaca aggtgcgcgc aatcgagctt gcgatgccga   3211
gctcctcagc cgcctgcgac aattcggcgc cggaggtgtc gatgatggac acgatcggca   3271
ggtttagctc gcgcgccagc gaaatgccac gacgcgcaaa acg                     3314
```

<210> SEQ ID NO 26
<211> LENGTH: 437
<212> TYPE: PRT
<213> ORGANISM: Corynebacterium glutamicum

<400> SEQUENCE: 26

Met Phe Glu Arg Asp Ile Val Ala Thr Asp Asn Asn Lys Ala Val Leu
1               5                   10                  15

His Tyr Pro Gly Gly Glu Phe Glu Met Asp Ile Ile Glu Ala Ser Glu
            20                  25                  30

Gly Asn Asn Gly Val Val Leu Gly Lys Met Leu Ser Glu Thr Gly Leu

-continued

```
            35                  40                  45
Ile Thr Phe Asp Pro Gly Tyr Val Ser Thr Gly Ser Thr Glu Ser Lys
 50                  55                  60
Ile Thr Tyr Ile Asp Gly Asp Ala Gly Ile Leu Arg Tyr Arg Gly Tyr
 65                  70                  75                  80
Asp Ile Ala Asp Leu Ala Glu Asn Ala Thr Phe Asn Glu Val Ser Tyr
                 85                  90                  95
Leu Leu Ile Asn Gly Glu Leu Pro Thr Pro Asp Glu Leu His Lys Phe
                100                 105                 110
Asn Asp Glu Ile Arg His His Thr Leu Leu Asp Glu Asp Phe Lys Ser
                115                 120                 125
Gln Phe Asn Val Phe Pro Arg Asp Ala His Pro Met Ala Thr Leu Ala
                130                 135                 140
Ser Ser Val Asn Ile Leu Ser Thr Tyr Tyr Gln Asp Gln Leu Asn Pro
145                 150                 155                 160
Leu Asp Glu Ala Gln Leu Asp Lys Ala Thr Val Arg Leu Met Ala Lys
                165                 170                 175
Val Pro Met Leu Ala Ala Tyr Ala His Arg Ala Arg Lys Gly Ala Pro
                180                 185                 190
Tyr Met Tyr Pro Asp Asn Ser Leu Asn Ala Arg Glu Asn Phe Leu Arg
                195                 200                 205
Met Met Phe Gly Tyr Pro Thr Glu Pro Tyr Glu Ile Asp Pro Ile Met
                210                 215                 220
Val Lys Ala Leu Asp Lys Leu Leu Ile Leu His Ala Asp His Glu Gln
225                 230                 235                 240
Asn Cys Ser Thr Ser Thr Val Arg Met Ile Gly Ser Ala Gln Ala Asn
                245                 250                 255
Met Phe Val Ser Ile Ala Gly Gly Ile Asn Ala Leu Ser Gly Pro Leu
                260                 265                 270
His Gly Gly Ala Asn Gln Ala Val Leu Glu Met Leu Glu Asp Ile Lys
                275                 280                 285
Ser Asn His Gly Gly Asp Ala Thr Glu Phe Met Asn Lys Val Lys Asn
290                 295                 300
Lys Glu Asp Gly Val Arg Leu Met Gly Phe Gly His Arg Val Tyr Lys
305                 310                 315                 320
Asn Tyr Asp Pro Arg Ala Ala Ile Val Lys Glu Thr Ala His Glu Ile
                325                 330                 335
Leu Glu His Leu Gly Gly Asp Asp Leu Leu Asp Leu Ala Ile Lys Leu
                340                 345                 350
Glu Glu Ile Ala Leu Ala Asp Asp Tyr Phe Ile Ser Arg Lys Leu Tyr
                355                 360                 365
Pro Asn Val Asp Phe Tyr Thr Gly Leu Ile Tyr Arg Ala Met Gly Phe
                370                 375                 380
Pro Thr Asp Phe Phe Thr Val Leu Phe Ala Ile Gly Arg Leu Pro Gly
385                 390                 395                 400
Trp Ile Ala His Tyr Arg Glu Gln Leu Gly Ala Ala Gly Asn Lys Ile
                405                 410                 415
Asn Arg Pro Arg Gln Val Tyr Thr Gly Asn Glu Ser Arg Lys Leu Val
                420                 425                 430
Pro Arg Glu Glu Arg
                435

<210> SEQ ID NO 27
```

```
<211> LENGTH: 20
<212> TYPE: DNA
<213> ORGANISM: Artificial Sequence
<220> FEATURE:
<223> OTHER INFORMATION: Primer gltA_XL-A1

<400> SEQUENCE: 27
tgagttctat tggcgtgacc                                              20

<210> SEQ ID NO 28
<211> LENGTH: 20
<212> TYPE: DNA
<213> ORGANISM: Artificial Sequence
<220> FEATURE:
<223> OTHER INFORMATION: Primer gltA_XL-E1

<400> SEQUENCE: 28
ttcgccaacg atgatgtcag                                              20

<210> SEQ ID NO 29
<211> LENGTH: 19
<212> TYPE: DNA
<213> ORGANISM: Artificial Sequence
<220> FEATURE:
<223> OTHER INFORMATION: Primer gltA_1.p

<400> SEQUENCE: 29
ccgtcgacaa tagcctgaa                                               19

<210> SEQ ID NO 30
<211> LENGTH: 26
<212> TYPE: DNA
<213> ORGANISM: Artificial Sequence
<220> FEATURE:
<223> OTHER INFORMATION: Primer gltA_2.p

<400> SEQUENCE: 30
ccgaattctt cgagcatctc cagaac                                       26

<210> SEQ ID NO 31
<211> LENGTH: 1695
<212> TYPE: DNA
<213> ORGANISM: Corynebacterium glutamicum
<220> FEATURE:
<221> NAME/KEY: misc_feature
<222> LOCATION: (1)..(2)
<223> OTHER INFORMATION: sequence CC
<220> FEATURE:
<221> NAME/KEY: misc_feature
<222> LOCATION: (3)..(8)
<223> OTHER INFORMATION: SalI restriction sequence
<220> FEATURE:
<221> NAME/KEY: misc_feature
<222> LOCATION: (9)..(832)
<223> OTHER INFORMATION: sequence usptream of the coding region
<220> FEATURE:
<221> NAME/KEY: CDS
<222> LOCATION: (833)..(1687)
<223> OTHER INFORMATION: N terminal portion of the coding region
<220> FEATURE:
<221> NAME/KEY: misc_feature
<222> LOCATION: (847)..(847)
<223> OTHER INFORMATION: Transversion A > T
<220> FEATURE:
<221> NAME/KEY: misc_feature
<222> LOCATION: (1688)..(1693)
<223> OTHER INFORMATION: RcoRI restriction sequence
<220> FEATURE:
<221> NAME/KEY: misc_feature
<222> LOCATION: (1694)..(1695)
<223> OTHER INFORMATION: Sequence GG
```

<400> SEQUENCE: 31

```
ccgtcgacaa tagcctgaat ctgttctggt cgaaccttgg aaggtccgca gccgaaacgg      60
ccgtcgccag ggatgaactc agagggcagg gtggggaagt cggtcatgtc ttcgggcaac     120
tttctgcgct tggaagtaaa agggccaggg atcgttaacg atctgaccca caactataa     180
ccctgaagct gtcagttcct agcaccctag attcttcacg cagtctccca aacgatgaaa     240
aacgcccaaa actggcgaca ccgaactatt gaaaacgcgg ggattagttg accagccacc     300
aatttggggg tagctcaaag ttttgcaaag ttttcaattt ctaggttgtt aatatcccct     360
gaggttgcgt tatagggtgg cgaattgcat ggggaaagct actcggcacc catccttgtc     420
gcgtgcatca caaactttgc taaactgtgc accagtccac ttattgtggg atttttaatg     480
ccttaaaggc cagcattttc accctctagc ggggttgaat gctggccttg agggtgcaga     540
actaaatagc agcacatcgg cacaattgat ctgagttcta ttggcgtgac cgtggctact     600
gattacggtg gctgtgggtg gtcgggaatg atgtaaccaa cgtgattgtg ggggaattgg     660
ctctcacttc ggatatggct aaaccgcatt tatcggtata gcgtgttaac cggaccagat     720
tgggaaagaa atgtgtcgag taacaaaaac tgacatgcgc ttggcgcatc ccagttggta     780
agaataaacg ggactacttc cgtaatccgg aagagttttt ttccgaacaa at atg ttt    838
                                                          Met Phe
                                                            1 gaa agg gtt atc gtg gct act gat aac aac aag gct gtc ctg cac tac    886
Glu Arg Val Ile Val Ala Thr Asp Asn Asn Lys Ala Val Leu His Tyr
          5                   10                  15 ccc ggt ggc gag ttc gaa atg gac atc atc gag gct tct gag ggt aac    934
Pro Gly Gly Glu Phe Glu Met Asp Ile Ile Glu Ala Ser Glu Gly Asn
     20                  25                  30 aac ggt gtt gtc ctg ggc aag atg ctg tct gag act gga ctg atc act    982
Asn Gly Val Val Leu Gly Lys Met Leu Ser Glu Thr Gly Leu Ile Thr
 35                  40                  45                  50 ttt gac cca ggt tat gtg agc act ggc tcc acc gag tcg aag atc acc   1030
Phe Asp Pro Gly Tyr Val Ser Thr Gly Ser Thr Glu Ser Lys Ile Thr
                 55                  60                  65 tac atc gat ggc gat gcg gga atc ctg cgt tac cgc ggc tat gac atc   1078
Tyr Ile Asp Gly Asp Ala Gly Ile Leu Arg Tyr Arg Gly Tyr Asp Ile
             70                  75                  80 gct gat ctg gct gag aat gcc acc ttc aac gag gtt tct tac cta ctt   1126
Ala Asp Leu Ala Glu Asn Ala Thr Phe Asn Glu Val Ser Tyr Leu Leu
         85                  90                  95 atc aac ggt gag cta cca acc cca gat gag ctt cac aag ttt aac gac   1174
Ile Asn Gly Glu Leu Pro Thr Pro Asp Glu Leu His Lys Phe Asn Asp
    100                 105                 110 gag att cgc cac cac acc ctt ctg gac gag gac ttc aag tcc cag ttc   1222
Glu Ile Arg His His Thr Leu Leu Asp Glu Asp Phe Lys Ser Gln Phe
115                 120                 125                 130 aac gtg ttc cca cgc gac gct cac cca atg gca acc ttg gct tcc tcg   1270
Asn Val Phe Pro Arg Asp Ala His Pro Met Ala Thr Leu Ala Ser Ser
                135                 140                 145 gtt aac att ttg tct acc tac tac cag gac cag ctg aac cca ctc gat   1318
Val Asn Ile Leu Ser Thr Tyr Tyr Gln Asp Gln Leu Asn Pro Leu Asp
            150                 155                 160 gag gca cag ctt gat aag gca acc gtt cgc ctc atg gca aag gtt cca   1366
Glu Ala Gln Leu Asp Lys Ala Thr Val Arg Leu Met Ala Lys Val Pro
        165                 170                 175 atg ctg gct gcg tac gca cac cgc gca cgc aag ggt gct cct tac atg   1414
Met Leu Ala Ala Tyr Ala His Arg Ala Arg Lys Gly Ala Pro Tyr Met
```

```
                180                 185                 190
tac cca gac aac tcc ctc aat gcg cgt gag aac ttc ctg cgc atg atg      1462
Tyr Pro Asp Asn Ser Leu Asn Ala Arg Glu Asn Phe Leu Arg Met Met
195                 200                 205                 210 ttc ggt tac cca acc gag cca tac gag atc gac cca atc atg gtc aag      1510
Phe Gly Tyr Pro Thr Glu Pro Tyr Glu Ile Asp Pro Ile Met Val Lys
            215                 220                 225 gct ctg gac aag ctg ctc atc ctg cac gct gac cac gag cag aac tgc      1558
Ala Leu Asp Lys Leu Leu Ile Leu His Ala Asp His Glu Gln Asn Cys
        230                 235                 240 tcc acc tcc acc gtt cgt atg atc ggt tcc gca cag gcc aac atg ttt      1606
Ser Thr Ser Thr Val Arg Met Ile Gly Ser Ala Gln Ala Asn Met Phe
    245                 250                 255 gtc tcc atc gct ggt ggc atc aac gct ctg tcc ggc cca ctg cac ggt      1654
Val Ser Ile Ala Gly Gly Ile Asn Ala Leu Ser Gly Pro Leu His Gly
260                 265                 270 ggc gca aac cag gct gtt ctg gag atg ctc gaa gaattcgg                 1695
Gly Ala Asn Gln Ala Val Leu Glu Met Leu Glu
275                 280                 285

<210> SEQ ID NO 32
<211> LENGTH: 285
<212> TYPE: PRT
<213> ORGANISM: Corynebacterium glutamicum

<400> SEQUENCE: 32

Met Phe Glu Arg Val Ile Val Ala Thr Asp Asn Asn Lys Ala Val Leu
1               5                   10                  15

His Tyr Pro Gly Gly Glu Phe Glu Met Asp Ile Ile Glu Ala Ser Glu
            20                  25                  30

Gly Asn Asn Gly Val Val Leu Gly Lys Met Leu Ser Glu Thr Gly Leu
        35                  40                  45

Ile Thr Phe Asp Pro Gly Tyr Val Ser Thr Gly Ser Thr Glu Ser Lys
    50                  55                  60

Ile Thr Tyr Ile Asp Gly Asp Ala Gly Ile Leu Arg Tyr Arg Gly Tyr
65                  70                  75                  80

Asp Ile Ala Asp Leu Ala Glu Asn Ala Thr Phe Asn Glu Val Ser Tyr
                85                  90                  95

Leu Leu Ile Asn Gly Glu Leu Pro Thr Pro Asp Glu Leu His Lys Phe
            100                 105                 110

Asn Asp Glu Ile Arg His His Thr Leu Leu Asp Glu Asp Phe Lys Ser
        115                 120                 125

Gln Phe Asn Val Phe Pro Arg Asp Ala His Pro Met Ala Thr Leu Ala
    130                 135                 140

Ser Ser Val Asn Ile Leu Ser Thr Tyr Tyr Gln Asp Gln Leu Asn Pro
145                 150                 155                 160

Leu Asp Glu Ala Gln Leu Asp Lys Ala Thr Val Arg Leu Met Ala Lys
                165                 170                 175

Val Pro Met Leu Ala Ala Tyr Ala His Arg Ala Arg Lys Gly Ala Pro
            180                 185                 190

Tyr Met Tyr Pro Asp Asn Ser Leu Asn Ala Arg Glu Asn Phe Leu Arg
        195                 200                 205

Met Met Phe Gly Tyr Pro Thr Glu Pro Tyr Glu Ile Asp Pro Ile Met
    210                 215                 220

Val Lys Ala Leu Asp Lys Leu Leu Ile Leu His Ala Asp His Glu Gln
225                 230                 235                 240
```

-continued

```
Asn Cys Ser Thr Ser Thr Val Arg Met Ile Gly Ser Ala Gln Ala Asn
                245                 250                 255

Met Phe Val Ser Ile Ala Gly Gly Ile Asn Ala Leu Ser Gly Pro Leu
            260                 265                 270

His Gly Gly Ala Asn Gln Ala Val Leu Glu Met Leu Glu
        275                 280                 285
```